(12) United States Patent
Wei et al.

(10) Patent No.: US 10,688,077 B2
(45) Date of Patent: Jun. 23, 2020

(54) INFLAMMASOME ACTIVATION IN MYELODYSPLASTIC SYNDROMES

(71) Applicant: H. Lee Moffitt Cancer Center and Research Institute, Inc., Tampa, FL (US)

(72) Inventors: Sheng Wei, Tampa, FL (US); Alan List, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 15/552,578

(22) PCT Filed: Feb. 26, 2016

(86) PCT No.: PCT/US2016/019925
§ 371 (c)(1),
(2) Date: Aug. 22, 2017

(87) PCT Pub. No.: WO2016/138473
PCT Pub. Date: Sep. 1, 2016

(65) Prior Publication Data
US 2018/0050011 A1    Feb. 22, 2018

Related U.S. Application Data

(60) Provisional application No. 62/121,369, filed on Feb. 26, 2015, provisional application No. 62/155,994, filed on May 1, 2015.

(51) Int. Cl.
| | | |
|---|---|---|
| *A61K 31/341* | (2006.01) | |
| *A61K 31/454* | (2006.01) | |
| *A61K 31/711* | (2006.01) | |
| *A61K 31/12* | (2006.01) | |
| *A61K 31/64* | (2006.01) | |
| *A61K 31/713* | (2006.01) | |
| *A61K 31/34* | (2006.01) | |
| *G01N 33/574* | (2006.01) | |
| *G01N 33/68* | (2006.01) | |
| *A61K 31/7088* | (2006.01) | |
| *C12N 15/113* | (2010.01) | |
| *A61P 35/00* | (2006.01) | |

(52) U.S. Cl.
CPC .......... *A61K 31/341* (2013.01); *A61K 31/12* (2013.01); *A61K 31/34* (2013.01); *A61K 31/454* (2013.01); *A61K 31/64* (2013.01); *A61K 31/7088* (2013.01); *A61K 31/711* (2013.01); *A61K 31/713* (2013.01); *C12N 15/1137* (2013.01); *G01N 33/57426* (2013.01); *G01N 33/6872* (2013.01); *A61P 35/00* (2018.01); *C12N 2310/14* (2013.01); *G01N 2333/4727* (2013.01); *G01N 2333/96466* (2013.01); *G01N 2800/7095* (2013.01)

(58) Field of Classification Search
CPC .............................. A61K 31/341; A61P 35/00
USPC ......................................... 514/452, 418, 602
See application file for complete search history.

(56) References Cited

U.S. PATENT DOCUMENTS 6,166,064 A * 12/2000 Dombroski .......... C07C 311/60
514/452
8,759,303 B2    6/2014 Brown et al.

FOREIGN PATENT DOCUMENTS

| WO | 2014087408 A1 | 6/2014 |
|---|---|---|
| WO | 2014113802 A1 | 7/2014 |
| WO | 2015003149 A2 | 1/2015 |
| WO | 2015003246 A1 | 1/2015 |

OTHER PUBLICATIONS

Sorbera et al., "CC-5013", Drugs of the Future, vol. 28, No. 5, pp. 425-431 (2003).*
International Search Report for PCT/US2016/019925 dated May 19, 2016.
Coll, et al., "A small molecule inhibitior of the NLRP3 inflammasome is a potential therapeutic for inflammatory diseases", Nat. Med., vol. 21, No. 3, Feb. 16, 2015 (Feb. 16, 2015), pp. 248-255.

* cited by examiner

*Primary Examiner* — Kevin E Weddington
(74) *Attorney, Agent, or Firm* — Thomas|Horstemeyer, LLP

(57) ABSTRACT

Disclosed are methods for treating a meylodysplastic syndrome (MDS) in a subject that involves administering to the subject a therapeutically effective amount of an inflammasome inhibitor. Also disclosed are methods for diagnosing a myelodysplastic syndrome (MDS) in a subject. In some embodiments, the method involves assaying a sample from the subject to detect inflammasome activation, wherein an increase in inflammasome activation in the sample compared to a control is an indication of MDS in the subject. In some embodiments, the method involves assaying a sample from the subject to detect s100A9 protein levels, wherein an increase in s100A9 protein levels in the sample compared to a control is an indication of MDS in the subject. The disclosed methods can further involve treating the subject for MDS if an increase in inflammasome activation and/or s100A9 levels are detected.

11 Claims, 74 Drawing Sheets
Specification includes a Sequence Listing.

| A | a-Caspase-1 MFI | % a-Caspase-1+ |
|---|---|---|
| Control | 57.2 | 2.99 |
| 1ug S100A9 | 88.9 | 15.4 |
| 5ug S100A9 | 126 | 28.4 |
| 10ug S100A9 | 608 | 79 |
| 25ug S100A9 | 1192 | 95.4 |

| B | a-Caspase-1 MFI | % a-Caspase-1+ |
|---|---|---|
| Control | 95.7 | 20.3 |
| LPS | 128 | 41.4 |
| 24h S100A9 | 327 | 56.1 |
| 48h S100A9 | 330 | 58.5 |
| 72h S100A9 | 588 | 76.5 |

INFLAMMASOME ACTIVATION IN MYELODYSPLASTIC SYNDROMES

CROSS REFERENCE TO RELATED APPLICATIONS

This application is the 35 U.S.C. § 371 national stage application of PCT Application No. PCT/US2016/019925, filed Feb. 26, 2016, which claims the benefit of U.S. Provisional Patent Application Ser. No. 62/121,369 filed Feb. 26, 2015 and U.S. Provisional Patent Application Ser. No. 62/155,994 filed May 1, 2015, the disclosures of which are expressly incorporated herein by reference.

STATEMENT REGARDING FEDERALLY SPONSORED RESEARCH OR DEVELOPMENT

This invention was made with Government Support under Grant No. CA115308 and Grant No. CA187020 awarded by the National Institutes of Health. The Government has certain rights in the invention.

BACKGROUND

Myelodysplastic syndromes (MDS) are hematopoietic stem cell malignancies characterized by dysplastic and ineffective hematopoiesis. MDS bone marrow precursors have a larger cell size, deregulated proliferation and maturation, and accelerated attrition by programmed cell death (List A, et al. N Engl J Med. 2005 352(6):549-57; Span L. F, et al. Leuk Res. 2007 31(12):1659-67; Garcia-Manero G. Am J Hematol. 2014 89(1):97-108). Despite these shared phenotypes, MDS harbor a spectrum of clonal chromosome abnormalities and somatic gene mutations, the latter most commonly involving genes encoding RNA splicing and epigenetic regulatory proteins (Bejar R, et al. J Clin Oncol. 2011 29(5):504-15; Yoshida K, et al. Nature. 2011 478 (7367):64-9). How such diverse genetic events initiate a common MDS phenotype is unexplained.

Apoptosis, a non-inflammatory form of programmed cell death, has been implicated in the ineffective hematopoiesis in MDS based upon membrane phosphatidylserine externalization, mitochondrial depolarization, and DNA fragmentation. Nevertheless, the inflammatory cytokine and cellular milieu instead support innate immune activation (Takizawa, H., et al. Blood 2012 119:2991-3002). Inflammatory cytokines such as interleukin-1β (IL-1β), tumor necrosis factor-α, transforming growth factor-β, IL-6 and others are generated in excess in MDS accompanied by marked bone marrow expansion of hematopoietic-inhibitory, myeloid derived suppressor cells (MDSC) driven by the danger associated molecular pattern (DAMP) and Toll-like receptor (TLR)-4 and CD33 ligand, S100A9 (Mundle, S D. et al. Blood 199688:2640-2647; Chen, X. et al. J Clin Invest 2013 123:4595-4611; Vogl, T. et al. Nat Med 2007 13:1042-1049; Ehrchen, J M., et al. J Leukoc Biol 2009 86:557-566). MDS hematopoietic stem and progenitor cells (HSPC) over-express TLRs and their signaling intermediates, whose activation has been implicated in the proliferation of MDS progenitors and the pathogenesis of peripheral blood cytopenias (Maratheftis, C I., et al. Clin Cancer Res 2007 13:1154-1160; Rhyasen, G W. et al. Cancer Cell 2013 24:90-104; Hofmann, W K. et al. Blood 2002 100:3553-3560).

Recent studies have shown that activation of TLRs by select DAMPs can trigger pyroptosis, a novel caspase-1-dependent pro-inflammatory cell death (Brennan, M. A., and Cookson, B. T. Molecular microbiology 2000 38:31-40; Cookson, B. T., and Brennan, M. A. Trends in microbiology 2001 9:113-114; Masters, S. L., et. Al. Immunity 2012 37:1009-1023) that involves the activation of ion gradients, cell swelling and the release of IL-1β and IL-18, intracellular DAMPs and other pro-inflammatory cytokines (Bergsbaken, T., et. al. Nature Reviews Microbiology 2009 7:99-109). Pyroptosis is mediated by the formation of inflammasome complexes, which are cytosolic heptameric oligomers composed of nucleotide-binding domain and leucine-rich repeat pattern recognition receptors (NLRs). The best characterized NLR, NLRP3, undergoes a conformational change in response to DAMP interaction to recruit the adapter protein, apoptosis-associated speck-like protein containing a caspase-recruitment domain (ASC), and pro-caspase-1, which in turn cleaves pro-IL-1β & pro-IL-18 to generate their active forms. Inflammasome activation involves NFκB-induced transcriptional priming of inflammasome components, followed by cation channel activation with cell volume expansion and inflammasome component assembly (Bergsbaken, T., et. al. Nature Reviews Microbiology 2009 7:99-109; Brennan, M. A., and Cookson, B. T. Molecular microbiology 2000 38:31-40; Cookson, B. T., and Brennan, M. A. Trends in microbiology 2001 9:113-114; Fantuzzi, G., and Dinarello, C. A. Journal of clinical immunology 1999 19:1-11). Inflammasome assembly is induced by S100A9 homodimers and S100A8/9 heterodimers, which function as alarmins that induce NADPH oxidase to generate reactive oxygen species (ROS), and which extracellularly direct paracrine inflammatory signals (Fantuzzi, G., and Dinarello, C. A. Journal of clinical immunology 1999 19:1-11; Kessel, C., et. al. Clinical immunology 2013 147: 229-241; Lim, S. Y., et. al. Journal of leukocyte biology 2009 86:577-587; Simard, J. C., et. al. PloS One 2013 8:e72138).

Accordingly, there is a need for new methods of treatment and methods of diagnosis for myelodysplastic syndromes (MDS).

SUMMARY

Disclosed herein are new methods of treatment and methods of diagnosis for myelodysplastic syndromes (MDS). The inventors have identified that MDS hematopoietic stem and progenitor cells (HSPC) activate NLRP3 inflammasomes that drive caspase-1-dependent pyroptotic cell death, inflammatory cytokine generation, and clonal expansion. Inflammasome components are induced by danger-associated molecular pattern (DAMP) engagement of membrane Toll-like receptors (TLR), whereas cytoplasmic complex assembly is triggered by DAMP interaction with NOD-like receptor proteins (NLRP). Once activated, inflammasomes serve as platforms for caspase-1 activation, IL-1β and IL-18 maturation, cation channel activation and pyroptosis. Additionally, knockdown of caspase-1, neutralization of S100A9, and/or pharmacologic inhibition of the NLRP3 inflammasome or NADPH oxidase suppressed pyroptosis, ROS generation and active β-catenin while restoring effective hematopoiesis.

Therefore, a method is disclosed for treating myeloid disorders, such as myelodysplastic syndrome (MDS), in a subject that involves administering to the subject a therapeutically effective amount of an inflammasome inhibitor. In some cases, the subject has del(5q) MDS. In other cases, the subject has non-del(5q) MDS.

In some cases, the method is used as a primary therapy. However, in some cases, the method is used to treat a subject that has become resistant to a current therapy, such as recombinant erythropoietin, lenalidomide, azacitidine, decitabine, dexamethasone, or pharmaceutically acceptable salt thereof. For example, the current therapy can be maintained and supplemented with the inflammasome inhibitor, or it can be replaced by inflammasome inhibitor treatment.

The inflammasome inhibitor can be administered alone or in combination with other treatments. In one embodiment, the inflammasome inhibitor can be administered to the subject in combination with a therapeutically effective dose of recombinant erythropoietin, lenalidomide, azacitidine, decitabine, or dexamethasone.

Also disclosed herein are new methods of diagnosing myelodysplastic syndromes (MDS). Despite remarkable genetic heterogeneity, myelodysplastic syndromes (MDS) share features of cytological dysplasia and ineffective hematopoiesis. Activation of the NLRP3 inflammasome that drives clonal expansion and pyroptotic cell death is shown herein to be a hallmark of MDS hematopoietic stem/progenitor cells (HSPC). Independent of genotype, MDS HSPC overexpress inflammasome proteins and manifest activated NLRP3 complexes with consequent caspase-1 activation, IL-1β and IL-18 generation, and pyroptotic cell death. Mechanistically, pyroptosis was triggered by the alarmin S100A9 found in excess in MDS HSPC and bone marrow plasma, which like founder gene mutations, induced reactive oxygen species (ROS) to initiate cation influx, cell swelling and β-catenin activation. Accordingly, knockdown of caspase-1, neutralization of S100A9 in BM plasma, and pharmacologic inhibition of the NLRP3 inflammasome or NADPH oxidase suppressed pyroptosis, ROS generation and nuclear β-catenin in MDS HSPC while restoring effective hematopoiesis. Thus, DAMP signals and oncogenic mutations in MDS HSPC license a common redox-sensitive inflammasome platform to induce pyroptosis and self-renewal, suggesting new avenues for therapeutic intervention that restore effective hematopoiesis in MDS patients.

Disclosed herein are methods for diagnosing a myelodysplastic syndrome (MDS) in a subject. For example, the subject can be a patient suspected of having a hematological disorder. The median age at diagnosis of a MDS is between 60 and 75 years, a few patients are younger than 50. Therefore, in some embodiments, the subject is at least 50, 55, or 60 years of age. Signs and symptoms of MDS include anemia, neutropenia, and thrombocytopenia.

In some embodiments, the method involves assaying a sample from the subject to detect inflammasome activation, wherein an increase in inflammasome activation in the sample compared to a control is an indication of MDS in the subject.

An inflammasome is a multiprotein oligomer of caspase 1, PYCARD/ASC, and a member of the NOD-like receptor (NLR) family. NLRP1, NLRP3 and NLRC4 are subsets of the NLR family and thus have two common features: the first is a nucleotide-binding domain (NBD) which is bound to by ribonucleotide-phosphates (rNTP) and is important for self-oligomerization. The second is a C-terminus leucine-rich repeat (LRR), which serves as a ligand-recognition domain for other receptors (e.g. TLR) or microbial ligands. In some embodiments, the inflammasome is an NLRP3 inflammasome.

Inflammasome activation can detected directly or indirectly. For example, inflammasome activation can be detected by assaying for gene expression of CASP-1 (caspase-1 gene), NLRP3, or a combination thereof. Inflammasome activation can be detected by assaying for protein expression of active caspase-1, NLRP3, or a combination thereof. Inflammasome activation can also be detected by assaying directly for NLRP3 inflammasome complexes. For example, inflammasome activation can be detected by detecting co-localization of active caspase-1 and NLRP3 protein.

The inflammasome promotes the maturation of the inflammatory cytokines Interleukin 1β (IL-1β) and Interleukin 18 (IL-18). Therefore, in some embodiments, the method involves detecting IL-1β levels, IL-18, levels, or a combination thereof.

As disclosed herein, S100A9 and ROS, generated in response to NLRP3 activation or somatic gene mutations, serve as DAMP signaling intermediates responsible for inflammasome-mediated pyroptosis and β-catenin activation in MDS. Therefore, in some embodiments, the method involves assaying a sample from the subject to detect s00A9 protein levels, wherein an increase in s100A9 protein levels in the sample compared to a control is an indication of MDS in the subject.

The sample of the disclosed methods preferably comprises hematopoietic stem/progenitor cells (HSPC). Therefore, in some embodiments, the sample is a bone marrow sample.

The disclosed methods can further involve treating the subject for MDS if an increase in inflammasome activation and/or s100A9 levels are detected. As disclosed herein, the disclosed indications of inflammasome activation and s100A9 levels can also be used to predict whether the subject has low-risk or high-risk MDS. Therefore, this can be used to select the appropriate therapy, dosage, or combination thereof. In some embodiments, the method involves treating the subject with a therapeutically effective amount of inflammasome inhibitor. In some embodiments, the method involves treating the subject with a therapeutically effective amount of lenalidomide.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 1. qPCR analyses shows markedly increased expression of pyroptosis-associated genes in mononuclear cells (MNC) isolated from patient MDS bone marrow (BM) specimens (n=10 total; n=5 lower and n=5 higher-risk disease), compared to normal controls (n=5), for (A) CASP1, (B) CASP3, (C) NLRP3, (D) IL-1β, and (E) IL-18.

FIG. 2. Representative confocal fluorescence micrograph (2520× magnification, 7.5 μm scale) of a-caspase-1 and NLRP3 expression in MDS versus normal BM-MNC. DAPI (first column), a-caspase-1 (second column), NLRP3 (third column); merged image shows inflammasome formation (fourth column).

FIG. 3. Quantitative analysis of a-caspase-1/NLRP3 confocal images of BM-MNC isolated from lower-risk (n=7) and higher-risk (n=3) MDS patients, and normal donors (n=6). MDS patient specimens have significantly increased expression of (A) a-caspase-1 and (B) NLRP3 proteins, accompanied by (C) co-localization, confirming inflammasome assembly.

FIG. 4. Representative scatter plots of pyroptotic cells (a-caspase-1$^+$/annexin-V$^+$) by flow cytometry in four phenotypically distinct hematopoietic lineages and cell types: stem cells (CD34$^+$CD38$^-$), progenitor cells (CD34$^+$CD38$^+$), immature myeloids (CD33$^+$), and erythroids (CD71).

FIG. 5. Quantitation of the mean percentage of pyroptotic cells by hematopoietic lineage in MDS (n=8) versus normal donors (n=5).

FIG. 6. Comparison of the mean percentage of pyroptotic versus apoptotic cells (a-caspase-3/7$^+$/annexin-V$^+$) by hematopoietic lineage in lower-risk MDS specimens (n=5).

FIG. 7. Lower-risk MDS BM-MNC (n=3) were transfected by lentivirus with shRNAs targeting (A) CASP1 or (B) CASP3. Suppression of caspase-1 resulted in a significant reduction in the percentage of pyroptotic cells, whereas suppression of caspase-3 had no significant effect, confirming caspase-1 dependence.

FIG. 8. ELISA assessment of (A) BM plasma concentration of S100A9 in normal donors (n=12) versus lower-risk (n=33) and higher-risk (n=27) MDS and (B) BM plasma concentration of HMGB1 assessed by ELISA in normal donors (n=11) and MDS (n=55).

FIG. 9. qPCR analysis of (A) S100A9 mRNA in normal (n=2) versus lower-risk MDS (n=8) and (B) HAMGB1 transcript levels in normal (n=6) versus MDS BM-MNC (n=10).

FIG. 10. Changes in pyroptosis-related gene expression assessed by qPCR in untreated normal BM-MNC (n=3), normal BM-MNC treated with 1 µg/mL rhS100A9 for 24 hours (n=2), and in MDS patient specimens (n=5), for (A) CASP1, (B) IL-fi, (C) IL-18, and (D) NLRP3.

FIG. 11. Representative micrograph (2520× magnification, 7.5 µm scale) depicting inflammasome formation in normal, untreated BM-MNC or normal BM-MNC treated with 5 µg/mL rhS100A9 for 24 hours. DAPI (first column) a-caspase-1 (second column), and NLRP3 (third column); merged images show formation of inflammasome complexes (fourth column).

FIG. 12. Quantitative analysis of (A) a-caspase-1, (B) NLRP3, or (C) colocalization of a-caspase-1 and NLRP3 from confocal images from normal donors (n=6), normal BM-MNC treated with 5 µg/mL rhS100A9 (n=2), and MDS patients (n=10).

FIG. 13. Mean cell area was quantified following analysis of a-caspase-1/NLRP3 confocal images of BM from normal donor (n=6), lower-risk (n=7), and higher-risk MDS patient specimens (n=3). Mean cell area is augmented in MDS irrespective of risk score.

FIG. 14. NLRP3 MFI and cell area are correlated in lower-risk MDS patients (r=0.49, n=7).

FIG. 15. U937 cells were incubated with 12.5 µg/mL ethidium bromide (EB), and treated with 5 µg/mL rhS100A9 or media alone. Uptake of EB is depicted in green (680× magnification, 25 µm scale).

FIG. 16. BM-MNC from normal donors (n=3) and MDS patients (n=3) were incubated with autologous BM plasma for 24 hours. 12.5 µg/mL EB was then added to the cells, and dye incorporation measured by flow cytometry at 5 minute intervals.

FIG. 17. Photomicrograph images from normal donors illustrating (A) normal red blood cell (RBC, 7.0 µm) followed by normal erythroid lineage maturation of nucleated BM precursors with corresponding cell diameter (Left to right). (B) Corresponding images from MDS BM aspirates, demonstrating an oval macrocyte (RBC, 9.1 µm) followed by dysplastic and megaloblastic erythroid lineage maturation. (C) Normal myelocyte. (D) Enlarged dysplastic myelocyte with mild hypogranulation in MDS.

FIG. 18. Comparison of mean cell diameter in normal (n=4) versus MDS (n=4) BM during erythroid lineage maturation. Left to right, maturation is depicted as most to least mature cell populations. Error bars: SE, *$p<0.05$, $p<0.01$, and *$p<0.001$.

FIG. 19. Comparison of mean cell diameter in normal (n=4) versus MDS (n=4) BM during myeloid lineage maturation. Left to right, maturation is depicted as most to least mature cell populations. Error bars: SE, *$p<0.05$, $p<0.01$, and *$p<0.001$.

FIG. 20. Reduction in the fraction of pyroptotic BM cells from a MDS patient following treatment with 0.5 µg CD33-IgG$_1$ or 0.1 µM IRAK4 inhibitor. Values are normalized to autologous BM plasma-incubated MDS BM-MNC.

FIG. 21. Quantitation of the mean percentage of pyroptotic cells in each respective lineage in MDS BM-MNC incubated with autologous BM plasma and either 0.5 µg CD33-IgG$_1$ or 0.1 µM IRAK4 inhibitor for 24 hours (n=4).

FIG. 22. BM-MNC isolated from lower-risk MDS patients (n=5) were treated for 24 hours with CD33-IgG1, and pyroptosis-related gene expression was assessed by qPCR for (A) CASP1, (B) CASP3, (C) IL-1β, (D) IL-18, or (E) NLRP3.

FIG. 23. Colony forming capacity was assessed in BM-MNC from MDS patient specimens (n=3) that were treated with increasing concentrations of CD33-IgG$_1$, for (A) GEMM, (B) erythroid, or (C) GM cells.

FIG. 24. Colony forming capacity was assessed in BM-MNC from MDS patient specimens (n=3) that were treated with increasing concentrations of the inflammasome inhibitor MCC950, for (A) GEMM, (B) erythroid, or (C) GM cells.

FIG. 25. Quantitative analysis of (A) a-caspase-1 MFI, (B) NLRP3 MFI, (C) co-localization, and (D) cell area from confocal images of BM cells isolated from WT (n=2), 2 month (n=4), 6 month (n=5), and 11 month (n=4) old S100A9Tg mice.

FIG. 26. Representative micrograph (2520× magnification, 7.5 µm scale) of a-caspase-1 and NLRP3 protein expression in WT BM cells treated for 24 hours with 5 pig/mL S100A9, and of BM cells from S100A9Tg mice. DAPI (first column), a-caspase-1 (second column) and NLRP3 (third column); merged image illustrates inflammasome formation (fourth column).

FIG. 27. Quantitative analysis of (A) a-caspase-1 MFI, (B) NLRP3 MFI, (C) co-localization, and (D) cell area from confocal images of BM cells isolated from WT (n=2) mice, from WT BM cells treated for 24 hours with 5 µg/mL S100A9, or from BM cells from S100A9Tg mice (n=13).

FIG. 28. Representative scatter plots of pyroptotic KLS (c-Kit$^+$Lin$^-$Sca-1$^+$) cells isolated from (A) WT and (B) transgenic mice.

FIG. 29. Representative scatter plots of apoptotic KLS (c-Kit$^+$Lin$^-$Sca-1$^+$) cells isolated from (A) WT and (B) transgenic mice.

FIG. 30. Mean percentage of (A) pyroptotic and (B) apoptotic versus apoptotic KLS cells in WT (n=6) and S100A9Tg mice (n=6).

FIG. 31. Mean percentage of total (A) a-caspase-1+ and (B) a-caspase-3/T7+ KLS cells isolated from WT (n=6) and S100A9Tg mice (n=6).

FIGS. 32-38 show that S100A9 and MDS gene mutations induce ROS through NADPH oxidase to activate β-catenin. Error bars: SE, *p<0.05, p<0.01, and *p<0.001.

FIG. 32. The percentage of ROS positive cells were assessed by flow cytometry in BM-MNC isolated from MDS patients (n=5) and normal donors (n=2).

FIG. 33. The ROS MFI values were assessed by flow cytometry in BM-MNC isolated from MDS patients (n=5) and normal donors (n=2).

FIG. 34. Representative micrograph (2520× magnification, 7.5 μm scale) of β-catenin expression in normal BM-MNC (n=3), normal BM-MNC treated with 5 μg/mL rhS100A9 (n=3) and MDS patients (n=6). DAPI is depicted in the first column, β-catenin in the second column, and the merged image in the third column illustrates nuclear localization of β-catenin.

FIG. 35. Quantitation and scoring of β-catenin confocal images based on the presence of no, low, medium, or high nuclear β-catenin in normal BM-MNC, rhS100A9 treated normal BM cells, and MDS patients.

FIG. 36. Mean percentage of (A) ROS positive cells and (B) ROS MFI were assessed by flow cytometry in U2AF1 S34F mutant expressing TF-1 cells and corresponding WT cells. Data are representative of three independent experiments.

FIG. 37. Representative micrograph (1890× magnification, 10 μm scale) illustrating β-catenin expression in U2AF1 WT cells, cells expressing S34F, or S34F-expressing mutant cells treated with NAC or the NADPH oxidase inhibitor DPI for 24 hours prior to staining.

FIG. 38. Quantitation and scoring of β-catenin confocal images based on the presence of no, low, medium, or high nuclear β-catenin.

FIG. 39. Mean percentage of total a-caspase-1+ cells assessed by hematopoietic lineage. Data are representative of five normal donors and eight lower-risk MDS patients. Error bars: SE, *p<0.05 and **p<0.01.

FIG. 40. Mean percentage of total annexin-V+ cells assessed by hematopoietic lineage. Data are representative of five normal donors and eight lower-risk MDS patients. Error bars: SE, *p<0.05 and **p<0.01.

FIG. 41. Mean percentage of total a-caspase-3/7+ cells assessed by hematopoietic lineage. Data are representative of five normal donors and eight lower-risk MDS patients. Error bars: SE, *p<0.05 and **p<0.01.

FIG. 43. U937 monocytic cells were treated with increasing concentrations of rhS100A9 for 24 hours, resulting in a concentration-dependent increase in the fraction of pyroptotic cells.

FIG. 44. Active caspase-1 MFI and percent positive cells increase in a (A) concentration-dependent manner and (B) U937 cells treated with 5 μg/mL rhS100A9 over time show a time-dependent increase in a-caspase-1 MFI and percent positive cells.

FIG. 45. Representative histogram depicting a-caspase-1. LPS was used as a positive control for caspase-1 activation.

FIG. 46. Representative micrograph (1890× magnification, 10 μm scale) depicting inflammasome formation in U937 cells that were untreated or treated with 5 μg/mL rhS100A9 for 24 hours. DAPI (first column), a-caspase-1 (second column), NLRP3 (third column); merged image shows formation of inflammasome complexes (fourth column).

FIG. 47. Quantitative analysis of (A) a-caspase-1, (B) NLRP3, or (C) colocalization from confocal images of untreated and treated U937 cells. Cells were pooled for analysis.

FIG. 49. Representative histograms from flow cytometry in BM-MNC isolated from MDS patients (n=6) and normal controls (n=4).

FIG. 50. Mean percentage of S100A9+ cells. Intracellular levels of the alarmin S100A9 are increased across myeloid lineages. Intracellular levels of S100A9 were measured by flow cytometry in BM-MNC isolated from MDS patients (n=6) and normal controls (n=4).

FIG. 51. S100A9 MFI. Intracellular levels of the alarmin S100A9 are increased across myeloid lineages. Intracellular levels of S100A9 were measured by flow cytometry in BM-MNC isolated from MDS patients (n=6) and normal controls (n=4). Error bars: SE, *p<0.05.

FIG. 56. Representative density plot of inflammasome formation based on the detection of fluorescence pulse differences in ASC for (A) WT, (B) S34F, and (C) DPI cells.

FIG. 57. Quantitation of ASC in WT, S34F, and S34F cells treated with DPI for 24 hours.

FIG. 58. Representative scatter plots of pyroptotic cells by flow cytometry from WT, S34F, and S34F cells treated with DPI for 24 hours.

FIG. 59. Quantitation of the percentage of pyroptotic cells in mutant and WT cells.

FIG. 60. Quantitation of the relative percentage of total a-caspase-1$^+$ was assessed by flow cytometry in mutant and WT cells.

FIG. 61. The relative percentage of (A) total annexin-V$^+$ cells was assessed by flow cytometry and (B) the MFI of a-caspase-1 was assessed by flow cytometry.

FIG. 62. The MFI of (A) annexin-V was assessed by flow cytometry and (B) the mean cell area was quantitated from confocal images of WT and S34F mutant cells.

FIG. 63. Mean percentage of EB+ cells were measured vs. time (minutes). To investigate pore formation, 12.5 µg/mL EB was added to the WT and mutant line, and incorporation of the dye was measured by flow cytometry at 5 min intervals.

FIG. 70. Mean percentage of ROS-positive cells was assessed by flow cytometry.

FIG. 71. Mean percentage of ROS MFI was assessed by flow cytometry.

FIG. 72. Representative micrograph (2520× magnification, 7.5 µm scale) of β-catenin expression. DAPI (first column), β-catenin (second column), and the merged images show nuclear localization of β-catenin (third column).

FIG. 73. Quantitation and scoring of β-catenin confocal images based on the presence of no, low, medium, or high nuclear β-catenin in WT (n=6), K700E (n=6), and K700E cells treated with NAC (n=3) or DPI (n=3) for 24 hours.

FIG. 74. Representative density plot of inflammasome formation based on the detection of fluorescence pulse differences in ASC for (A) WT and (B) P95H cells FIG. 75. Quantitation of (A) ASC positive cells and (B) fold change of the mean percentage of pyroptotic cells.

FIG. 76. Quantitation of (A) total a-caspase-1$^+$ cells, (B) total annexin-V$^+$ cells in WT and P95H cells.

FIG. 77. Quantitation of MFI values for (A) a-caspase-1 and (B) annexin-V, normalized to WT transfected cells.

FIG. 78. Quantitation of (A) mean percentage of ROS positive cells and (B) ROS MFI in WT, P95H, and DPI cells.

FIG. 79. Representative micrograph (1890× magnification, 10 µm scale) of β-catenin expression. DAPI (first column), β-catenin (second column), and the merged images show nuclear localization of β-catenin (third column).

FIG. 80. Quantitation and scoring of β-catenin confocal images based on the presence of no, low, medium, or high nuclear ti-catenin. Error bars: SE, *$p<0.05$.

FIG. 81. Representative micrograph (2520× magnification, 7.5 µm scale) depicting inflammasome formation in control and KO cells that were untreated, or treated with NAC or DPI. DAPI (first row), a-caspase-1 (second row), NLRP3 (third row); merged images show inflammasome formation (fourth row).

FIG. 82. Quantitative analysis of a-caspase-1 confocal images. Cells were pooled for analysis.

FIG. 83. Quantitative analysis of NLRP3 confocal images. Cells were pooled for analysis.

FIG. 84. Quantitative analysis of colocalization of a-caspase-1 and NLRP3 from confocal images. Cells were pooled for analysis.

FIG. 85. Representative density plot of inflammasome formation based on the detection of fluorescence pulse differences in ASC.

FIG. 86. Quantitation of percentage of ASC positive cells in control and KO cells that were untreated, or treated with NAC or DPI.

FIG. 87. Quantitation of mean cell area in control and KO cells that were untreated, or treated with NAC or DPI.

FIG. 88. Percentage of EB+ cells vs. time (minutes) was measured to assess pore formation. Ethidium bromide was added to the cells and dye incorporation was measured by flow cytometry at 5 minute intervals.

FIG. 89. Mean percentage of ROS positive cells in control and KO cells that were untreated, or treated with NAC or DPI.

FIG. 90. ROS MFI was assessed by flow cytometry in control and KO cells that were untreated, or treated with NAC or DPI.

FIG. 91. Representative micrograph (2520× magnification, 7.5 μm scale) of β-catenin expression. DAPI (first row), β-catenin (second row), and the merged images show nuclear localization of β-catenin (third row).

FIG. 92. Quantitation and scoring of β-catenin confocal images based on the presence of no, low, medium, or high nuclear β-catenin. Cells were pooled for analysis, and measurements of significance were made on untreated deleted cells compared to NAC or DPI treated deleted cells. Error bars: SE, *$p<0.05$ and ***$p<0.001$.

Figure 107:
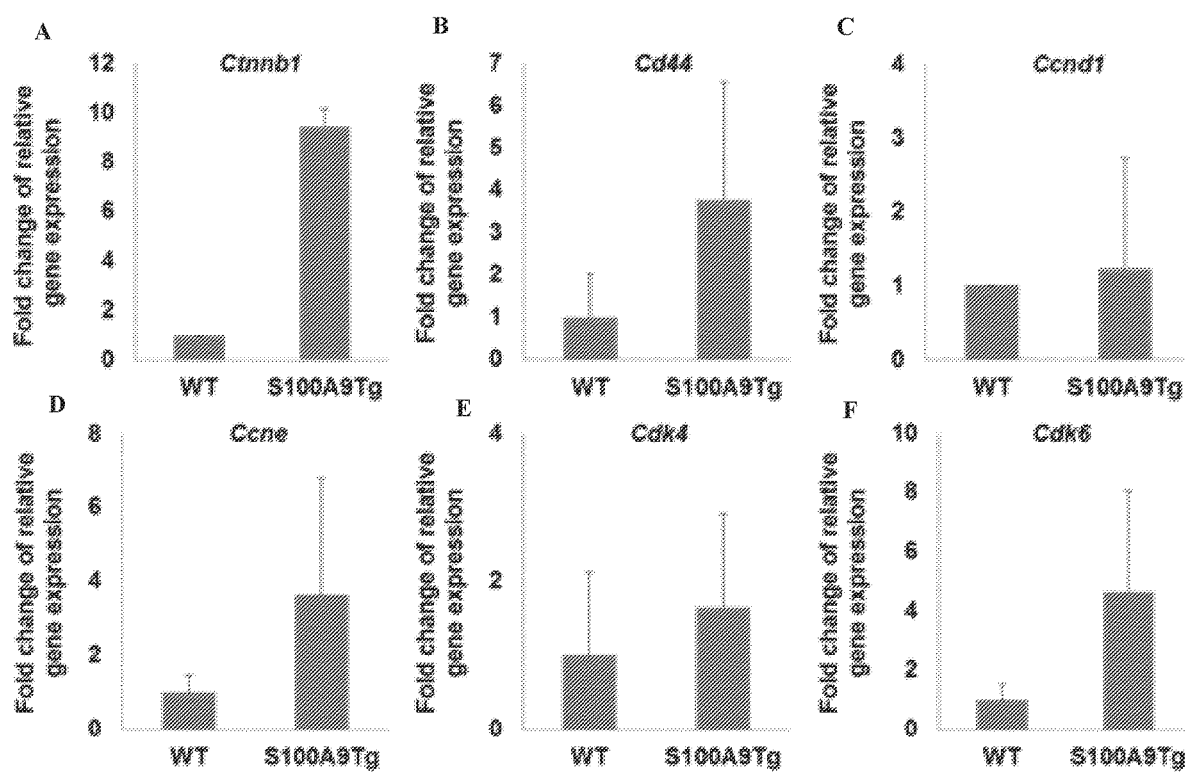

FIG. 107. Wnt/β-catenin target gene expression in WT and S100A9Tg BM cells for (A) Ctnnb1. (B) Cd44, (C) Ccnd1, (D) Ccne, (E) Cdk4, and (F) Cdk6.

Figure 108:
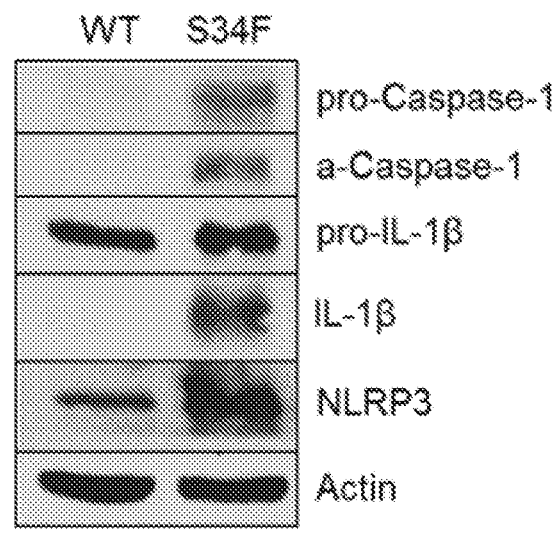

FIG. 108. Western blot of cleaved caspase-1 and IL-1β maturation.

FIGS. 109-116 show that inflammasome activation occurs via up-regulation of TXNIP and down-regulation of POP-1. Error bars: SE, *$p<0.05$. Data are representative of three independent experiments.

Figure 109:
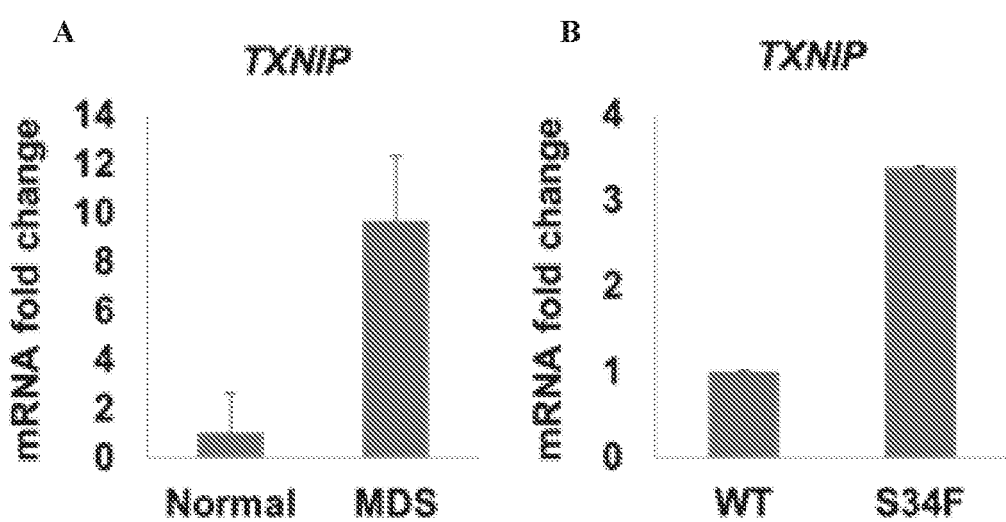

FIG. 109. qPCR analyses of TXNIP expression in (A) lower-risk MDS BM-MNC (n=9) compared to normal donor controls (n=4) and (B) in U2AF1-S34F-expressing cells compared to WT.

Figure 110:
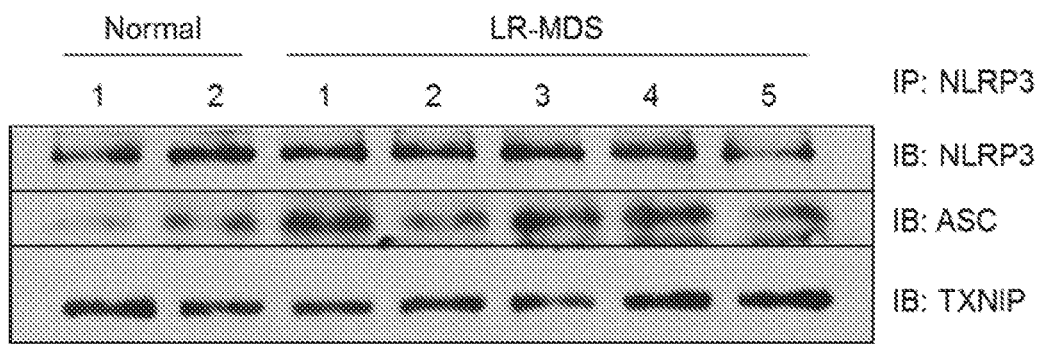

FIG. 110. Binding of TXNIP and ASC to NLRP3 in lower-risk MDS BM-MNC.

Figure 111:
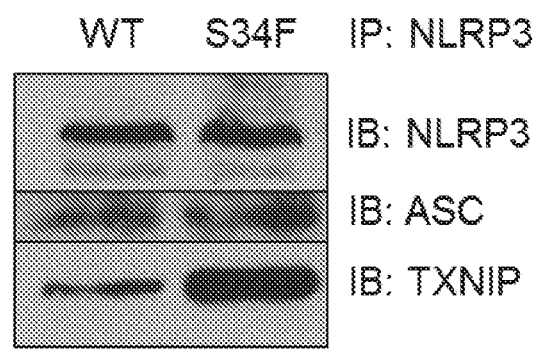

FIG. 111. Binding of TXNIP and ASC to NLRP3 in U2AF1-S34F cells (IP: NLRP3, IB: NLRP3, ASC, TXNIP).

Figure 112:
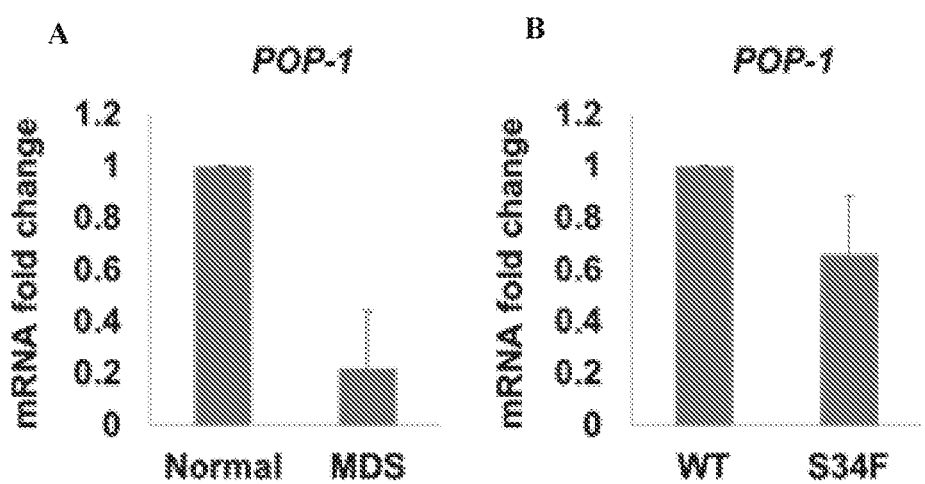

FIG. 112. qPCR analyses of POP-1 expression in (A) lower-risk MDS BM-MNC (n=9) compared to normal donor controls (n=4) and (B) in U2AF1-S34F-expressing cells compared to WT.

Figure 113:
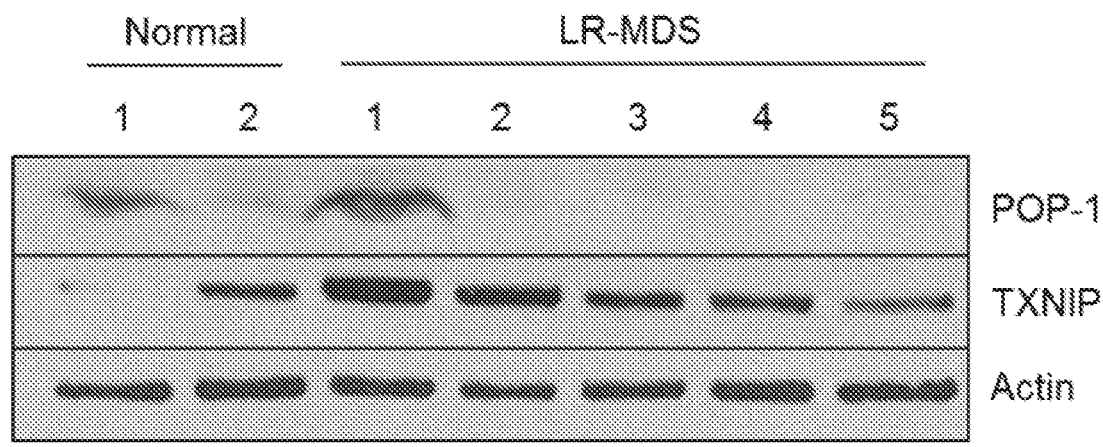

FIG. 113. Western blot of POP-1 and TXNIP protein expression in lower-risk MDS BM-MNC compared to normal donors.

Figure 114:
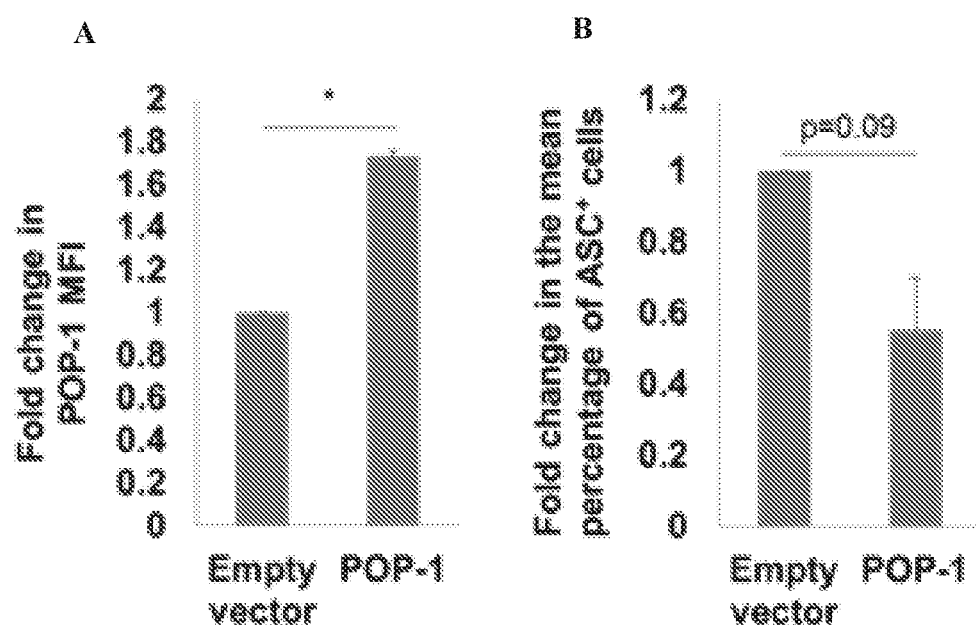

FIG. 114. POP-1 protein expression (A) and ASC oligomerization (B) following transient transfection of U2AF1-S34F-expressing cells.

Figure 115:
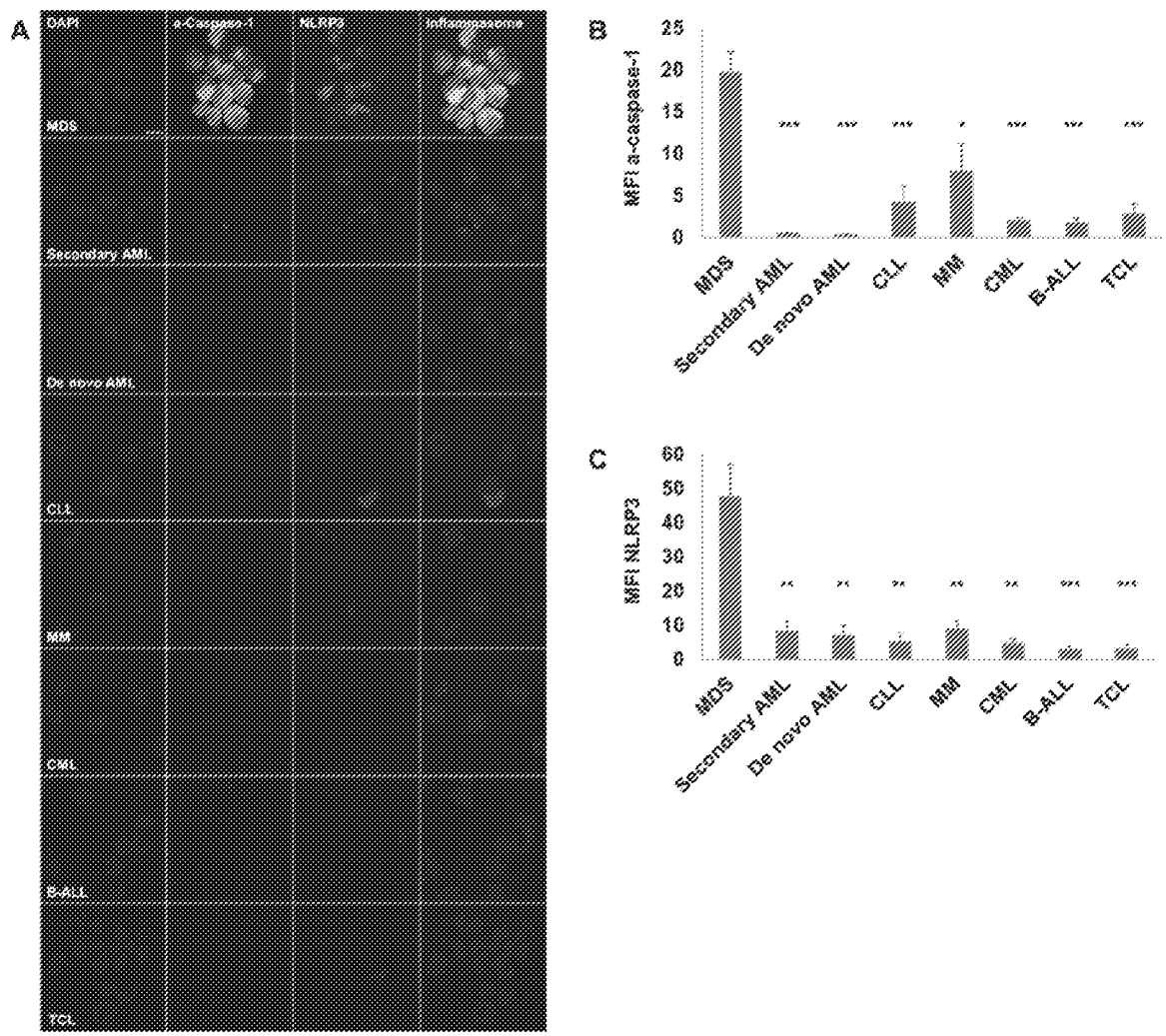

FIG. 115 shows that NLRP3 inflammasome assembly may be MDS-specific. (A) Representative confocal fluorescence micrograph (2520× magnification, 7.5 µm scale) of a-caspase-1 and NLRP3 expression in MDS (n=10), secondary AML (n=3), de novo AML (n=2), chronic lymphocytic leukemia (CLL, n=5), multiple myeloma (MM, n=5), chronic myeloid leukemia (CML, n=3), acute B lymphoblastic leukemia (B-ALL, n=3) and T cell lymphoma (TCL, n=3) BM-MNC. DAPI (first column), a-caspase-1 (second column), NLRP3 (third column); merged images show inflammasome formation (fourth column). Quantitative analysis of (B) a-Caspase-1 MFI and (C) NLRP3 MFI. Error bars: SE, *p<0.05, p<0.01 and *p<0.001.

Figure 116:
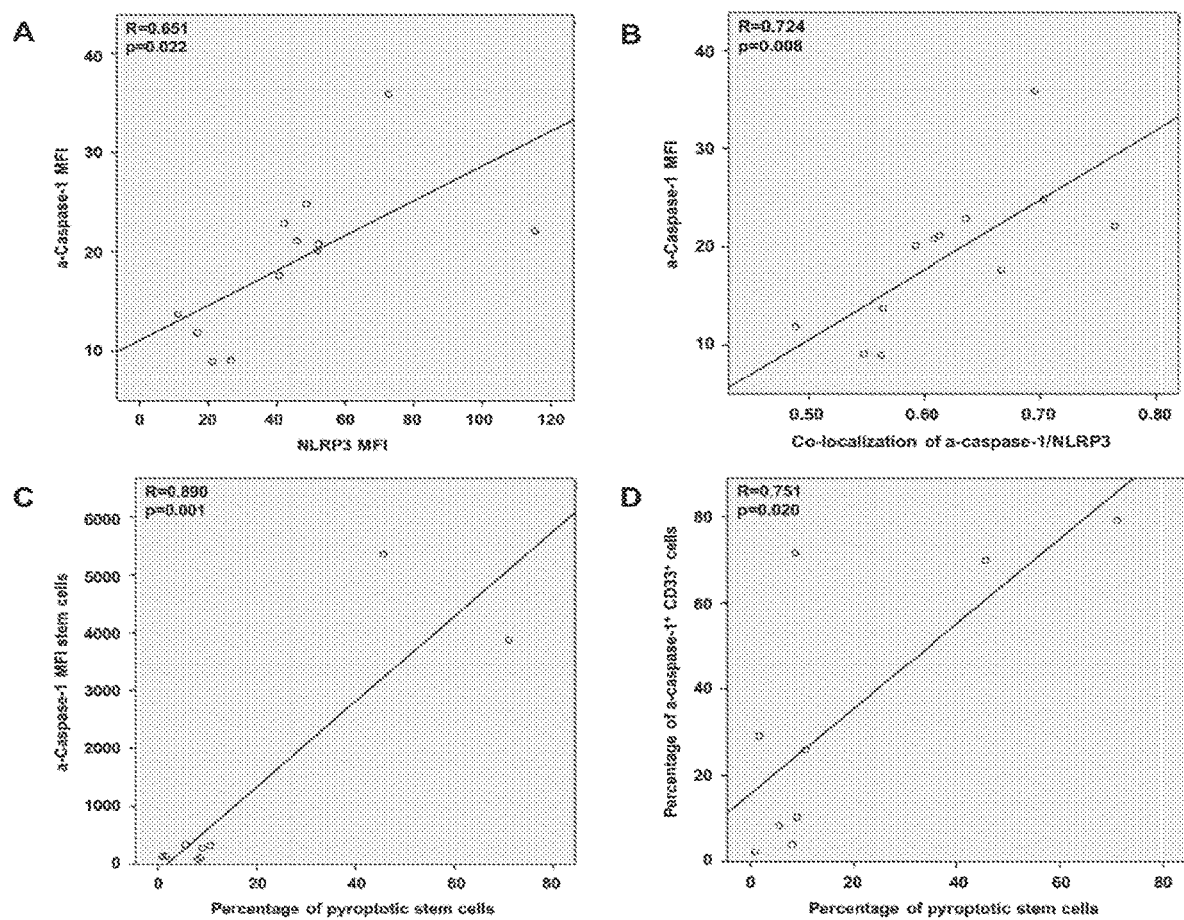

FIG. 116 shows that caspase-1 activation significantly correlates with the extent of pyroptosis detected in MDS BM-MNC. (A)-(B) a-caspase-1 MFI, NLRP3 MFI and NLRP3 inflammasome formation measured by co-localization of a-caspase-1/NLRP3, were determined by analysis of confocal immunofluorescence images. (C)-(D) The percentage of pyroptotic stem cells and MFI of a-caspase-1 in the stem cell and $CD33^+$ population were determined by flow cytometry.

Figure 117:
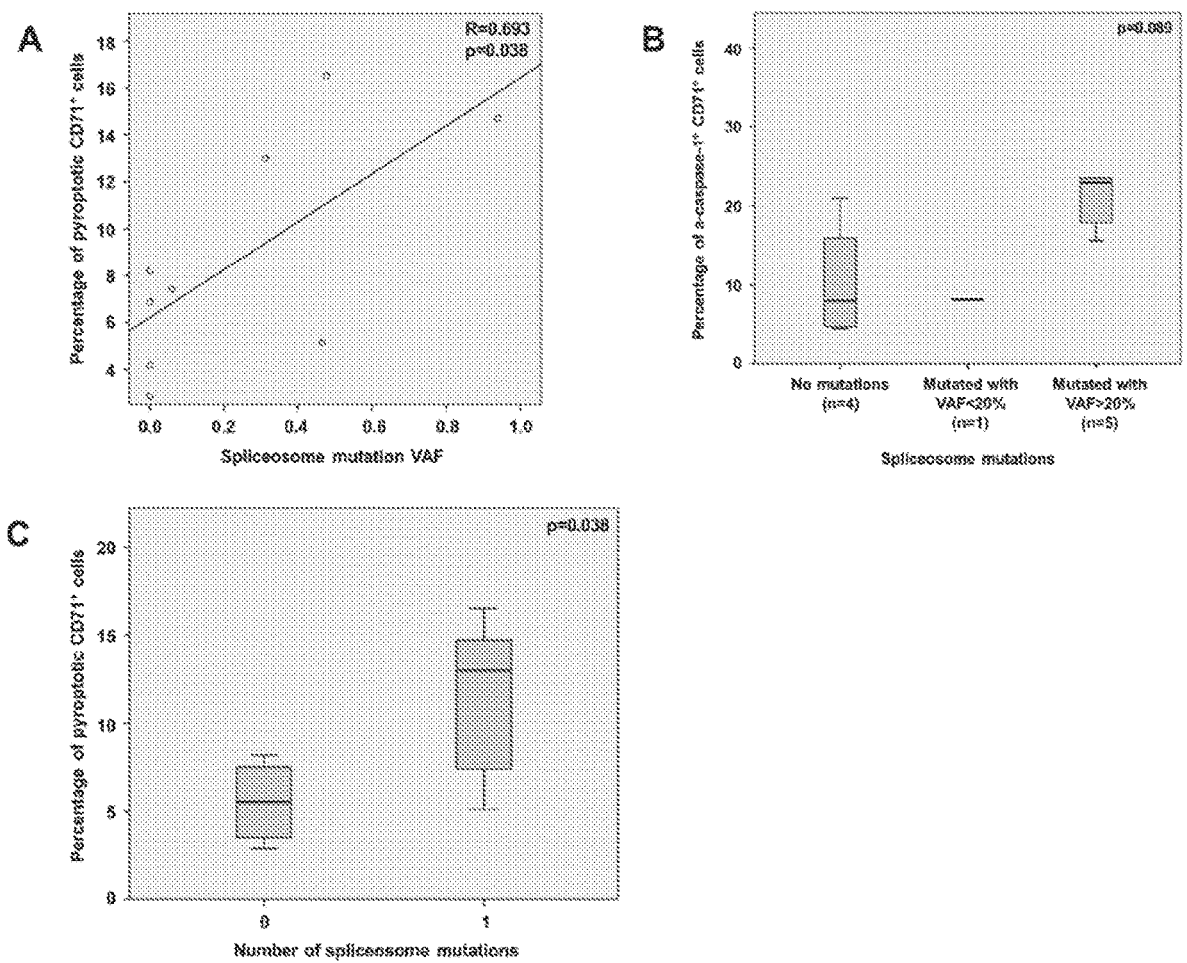

FIG. 117. The fraction of pyroptotic erythroid progenitors increases proportional to spliceosomal gene mutation variant allele fraction. (A) The percentage of pyroptotic $CD71^+$ cells significantly increases with spliceosome mutation VAF. (B) There is a trend toward increased a-caspase-$1^+$ $CD71^+$ cells with VAF. (C) The percentage of pyroptotic $CD71^+$ cells increases with the number of spliceosome gene mutations.

DETAILED DESCRIPTION

Disclosed herein are new methods of treatment and methods of diagnosis for myelodysplastic syndromes (MDS). The inventors have identified that MDS hematopoietic stem and progenitor cells (HSPC) activate NLRP3 inflammasomes that drive caspase-1-dependent pyroptotic cell death, inflammatory cytokine generation, and clonal expansion. Inflammasome components are induced by danger-associated molecular pattern (DAMP) engagement of membrane Toll-like receptors (TLR), whereas cytoplasmic complex assembly is triggered by DAMP interaction with NOD-like receptor proteins (NLRP). Once activated, inflammasomes serve as platforms for caspase-1 activation, IL-1β and IL-18 maturation, cation channel activation and pyroptosis. Additionally, knockdown of caspase-1, neutralization of S100A9, and/or pharmacologic inhibition of the NLRP3 inflammasome or NADPH oxidase suppressed pyroptosis, ROS generation and active β-catenin while restoring effective hematopoiesis.

Myelodysplastic Syndromes (MDS)

Myelodysplastic syndromes (MDS) share features of cytological dysplasia and ineffective hematopoiesis despite remarkable genetic heterogeneity. MDS HSPC are disclosed herein to routinely activate a redox-sensitive inflammasome signaling pathway that drives caspase-1 dependent pyroptotic cell death, inflammatory cytokine generation and clonal expansion. Inflammasome components are induced by danger-associated molecular pattern (DAMP) signal activation of membrane Toll-like receptors (TLR), whereas cytoplasmic complex assembly is triggered by DAMP interaction with NOD-like receptor proteins (NLRP). Once activated, inflammasomes serve as platforms for caspase-1 activation, IL-1β and IL-18 maturation, cation influx and pyroptosis. MDS HSPC are shown to overexpress inflammasome proteins accompanied by NLRP3 and NLRP1 inflammasome complex formation, caspase-1 activation, IL-1β generation and pyroptotic cell death independent of genotype. Pyroptosis was triggered by the DAMP protein S100A9 found in excess in MDS bone marrow (BM) plasma, which in turn induced reactive oxygen species (ROS), cation influx with cell swelling, and β-catenin activation. Knock-down of caspase-1, but not caspase-3, in patient-derived BM cells suppressed pyroptosis. Similarly, neutralization of S100A9 in BM plasma or pharmacologic inhibition of the NLRP inflammasome suppressed pyroptosis, ROS generation and nuclear β-catenin while restoring effective hematopoiesis. Lastly, cells overexpressing varied splicing gene mutations displayed cation channel activation, larger cell size, inflammasome assembly, pyroptosis and β-catenin activation compared to wild-type cells that was extinguished by NAC, indicating that diverse MDS gene mutations initiate pyroptosis by superoxide generation. These findings provide the first evidence that DAMP signals and oncogene mutations in MDS license a common redox-sensitive inflammasome platform to induce pyroptosis, inflammatory cytokine generation, expansion of cell volume and enhance self-renewal.

Inflammasome Inhibitors

Several different proteins have been identified as platforms for the formation of the inflammasome, and each has a distinct set of stimuli recognition. In some embodiments, the inflammasome inhibitor comprises a NLRP3 inflammasome inhibitor or a caspase-1 inhibitor (or a pan caspase inhibitor).

In some embodiments, the inflammasome inhibitor is 3,5,7-trihydroxy-4'-methoxy-8-(3-hydroxy-3-methylbutyl)-flavone (ICT).

In some embodiments, the inflammasome inhibitor has the following structure:

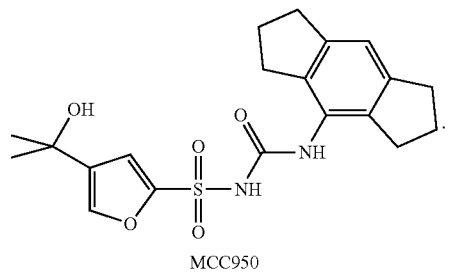 [SMILES: CC(C)(O)c1coc(S(=O)(=O)NC(=O)Nc2c3c(cc4c2CCC4)CCC3)c1]

MCC950

In some embodiments, the inflammasome inhibitor is selected from the group consisting of glybenclamide (glyburide), 5-chloro-2-methoxy-N-[2-(4-sulfamoylphenyl)ethyl]benzamide, and isoliquiritigenin.

In some embodiments, the inflammasome inhibitor comprises an S100A9 inhibitor. In some embodiments, the S100A9 inhibitor is an S100A9 high-affinity chimeric (CD33-$IgG_1$) decoy receptor. In some embodiments, the inflammasome inhibitor is a caspase-1 inhibitor. In some embodiments, the caspase-1 inhibitor is a shRNA targeting CASP1.

In some embodiments of the method, the amount of the inflammasome inhibitor and the amount of the lenalidomide are each periodically administered to the subject. In some embodiments of the method, the amount of the compound and the amount of the lenalidomide are administered simultaneously, separately or sequentially. In some embodiments of the method, the amount of the compound and the amount of the lenalidomide when taken together is more effective to treat the subject than when the compound or the lenalidomide is administered alone. In some embodiments of the method, the amount of the compound and the amount of the lenalidomide when taken together has a greater than additive effect on the MDS in the subject. In some embodiments of the method, the amount of the compound and the amount of the myelodysplastic syndrome when taken together is effective to reduce a clinical symptom of the MDS in the subject.

In some embodiments, the inflammasome inhibitor comprises an activator of AMP kinase. The adenosine monophosphate (AMP)-activated protein kinase (AMPK) is the downstream component of a protein kinase cascade that is activated by rising AMP coupled with falling ATP, these changes in cellular nucleotides signalling a fall in cellular energy status. One outcome of reduced AMPK signalling is increased cell proliferation. Activators of AMP kinase represent one embodiment to inhibit inflammasome activity.

Also disclosed is a pharmaceutical composition comprising an inflammasome inhibitor and at least one pharmaceutically acceptable carrier for use in treating MDS. Also disclosed is a pharmaceutical composition comprising an inflammasome inhibitor and lenalidomide, and at least one pharmaceutically acceptable carrier for use in treating MDS. In some embodiments, the pharmaceutically acceptable carrier comprises a liposome. In some embodiments of the pharmaceutical composition, the inflammasome inhibitor is contained in a liposome or microsphere, or the compound and the lenalidomide are contained in a liposome or microsphere. Also disclosed is a pharmaceutical composition comprising an amount a inflammasome inhibitor for use in treating a subject afflicted with MDS as an add-on therapy or in combination with, or simultaneously, contemporaneously or concomitantly with lenalidomide.

In some embodiments of any of the above methods or uses, the compound and/or the lenalidomide is orally administered to the subject. In some embodiments, the subject is transfusion dependent prior to treatment. In some embodiments, the subject is transfusion independent following treatment.

In some embodiments of any of the above methods, the MDS is primary (where no apparent risk factors are found) or secondary (where the MDS develops after being exposed to, for example, chemotherapy or radiation therapy, or exposure to industrial chemicals such as benzene).

The first International Prognostic Scoring System (IPSS) was derived from a study published in 1997 and separates patients into four categories: low risk, intermediate-1 risk, intermediate-2 risk, and high risk (Greenberg P, Cox C, LeBeau M M, et al. International scoring system for evaluating prognosis in myelodysplastic syndromes. Blood 1997: 89:2079-2088). A revised IPSS was developed in 2012 and separates patients into five categories: very low risk, low risk, intermediate risk, high risk, and very high risk (Greenberg P L, Tuechler H, Schanz J, et al. Revised international prognostic scoring system for myelodysplastic syndromes. Blood 2012, 120:2454-2465).

For the foregoing embodiments, each embodiment disclosed herein is contemplated as being applicable to each of the other disclosed embodiments. Thus, all combinations of the various elements described herein are within the scope of the invention.

Pharmaceutical Composition

Also disclosed is a pharmaceutical composition comprising the disclosed molecule in a pharmaceutically acceptable carrier Pharmaceutical carriers are known to those skilled in the art. These most typically would be standard carriers for administration of drugs to humans, including solutions such as sterile water, saline, and buffered solutions at physiological pH. For example, suitable carriers and their formulations are described in Remington: The Science and Practice of Pharmacy (21 ed.) ed. P P. Gerbino, Lippincott Williams & Wilkins, Philadelphia, Pa. 2005. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. The solution should be RNAse free. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Methods of Treatment

Disclosed is a method for treating myeloid disorders in a subject by administering to the subject a therapeutically effective amount of the disclosed pharmaceutical composition. The method can further involve administering to the subject lenalidomide, or an analogue or derivative thereof.

In some cases, the myeloid disorder is a myelodysplastic syndrome (MDS). MDSs are hematological (blood-related) medical conditions with ineffective production (or dysplasia) of the myeloid class of blood cells. In some cases, the MDS patient has a chromosome 5q deletion (del(5q)). However, in other cases, the patient has non-del5q MDS.

In some cases, the myeloid disorder is a myelodysplastic/myeloproliferative neoplasms (MDS/MPN). In some cases, the myeloid disorder is a myelodysplastic syndrome with myeloproliferative features. In some cases, the myeloid disorder is a therapy-related myeloid neoplasm.

The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for MDS. Thus, the method can further comprise identifying a subject at risk for MDS prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical daily dosage of the disclosed composition used alone might range from about 1 µg/kg to up to 100 mg/kg of body weight or more per day, depending on the factors mentioned above.

In some embodiments, the molecule containing lenalidomide is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of molecule containing lenalidomide administered to achieve a therapeutic effective dose is about 0.1 ng, 1 ng, 10 ng, 100 ng, 1 µg, 10 g, 100 g, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg 100 mg, 500 mg per kg of body weight or greater.

Definitions

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "sample from a subject" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally. The following delivery systems, which employ a number of routinely used pharmaceutical carriers, may be used but are only representative of the many possible systems envisioned for administering compositions in accordance with the invention.

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

The disclosed compounds may be in a salt form. As used herein, a "salt" is a salt of the instant compounds which has been modified by making acid or base salts of the compounds. In the case of compounds used to treat an infection or disease, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

As used herein, the term "therapeutically effective amount" or "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

Methods of Diagnosing Myelodysplastic Syndromes (MDS)

Apoptosis, a non-inflammatory form of programmed cell death, has been implicated in the ineffective hematopoiesis in MDS based upon membrane externalization of phosphatidylserine, mitochondrial depolarization and DNA fragmentation (Raza A, et al. Blood. 1995 86(1):268-76; Parker J. E, et al. Blood. 2000 96(12):3932-8; Tehranchi R, et al. Blood. 2003 101(3): 1080-6). Nevertheless, the inflammatory cytokine and cellular milieu instead support innate immune activation (Takizawa H, et al. Blood 2012 119:2991-3002). Inflammatory cytokines such as interleukin-1β (IL-1β), tumor necrosis factor-α, transforming growth factor-β, IL-6 and others are generated in excess in MDS, accompanied by bone marrow expansion of hematopoietic-inhibitory, myeloid derived suppressor cells (MDSC) activated by the danger associated molecular pattern (DAMP) S100A9, a Toll-like receptor (TLR)-4/CD33 ligand (Mundle S. D, et al. Blood. 1996 88(7):2640-7: Chen X, et al. J Clin Invest. 2013 123(11):4595-611; Vogl T, et al. Nat Med. 2007 13(9):1042-9; Ehrchen J. M, et al. J Leukoc Biol. 2009 86(3):557-66). MDS hematopoietic stem and progenitor cells (HSPC) express elevated levels of TLRs and their signaling intermediates, while TLR signaling has been implicated in the proliferation of MDS HSPC and in the pathogenesis of peripheral blood cytopenias (Maratheftis C. I., et al. Clin Cancer Res. 2007 13(4):1154-60; Rhyasen G. W, et al. Cancer Cell. 2013 24(1):90-104; Hofmann W. K, et al. Blood. 2002 100(10):3553-60).

Recent studies have shown that activation of TLRs by select DAMPs can trigger pyroptosis, a novel caspase-1-dependent pro-inflammatory cell death (Masters S. L, et al. Immunity. 2012 37(6):1009-23; Brennan M. A., et al. Mol Microbiol. 2000 38(1):31-40; Cookson B. T. & Brennan M. A. Trends Microbiol. 2001 9(3):113-4) that involves the activation of ion gradients, cell swelling and the release of IL-1β and IL-18, intracellular DAMPs and other pro-inflammatory cytokines (Ehrchen J. M, et al. J Leukoc Biol. 2009 86(3):557-66; Maratheftis C. I., et al. Clin Cancer Res. 2007 13(4):1154-60; Rhyasen G. W, et al. Cancer Cell. 2013 24(1):90-104; Masters S. L, et al. Immunity. 2012 37(6): 1009-23; Bergsbaken T, et al. Nat Rev Microbiol. 2009 7(2):99-109). Pyroptosis is mediated by the formation of inflammasome complexes, cytosolic heptameric oligomers composed of nucleotide-binding domain and leucine-rich repeat pattern recognition receptors (NLRs). The best characterized NLR, NLRP3, undergoes a conformational change in response to DAMP interaction to recruit the adapter protein, apoptosis-associated speck-like protein containing a caspase-recruitment domain (ASC), and pro-caspase-1, which in turn catalyzes proteolytic cleavage of pro-IL-1β & pro-IL-18 to their active forms (Brennan M. A., et al. Mol Microbiol. 2000 38(1):31-40). Inflammasome activation involves NFκB-induced transcriptional priming of inflammasome components, followed by cation channel activation with cell volume expansion and inflammasome component assembly (Brennan M. A., et al. Mol Microbiol. 2000 38(1):31-40; Cookson B. T. & Brennan M. A. Trends Microbiol. 2001 9(3): 113-4; Bergsbaken T, et al. Nat Rev Microbiol. 2009 7(2):99-109; Fantuzzi G. & Dinarello, C. A. J Clin Immunol. 1999 19(1):1-11). Inflammasome assembly is induced by S100A9 homodimers and S100A8 heterodimers, which function as alarmins regulating NADPH oxidase to generate reactive oxygen species (ROS), and which extracellularly direct paracrine inflammatory signals (Kessel C, et al. Clin Immunol. 2013 147(3):229-41; Lim S. Y., et al. J Leukoc Biol. 2009 86(3):577-87; Simard J. C, et al. PLoS One. 2013 8(8):e72138).

S100A9 and ROS, generated in response to NLRP3 activation or somatic gene mutations, are shown herein to serve as DAMP signaling intermediates responsible for inflammasome-mediated pyroptosis and β-catenin activation in MDS. Further, targeting this circuit restores effective hematopoiesis in MDS.

In some aspects, the disclosed method is an immunoassay. Immunoassays, in their most simple and direct sense, are binding assays involving binding between antibodies and antigen. For example, antibodies that specifically bind human a-caspase-1, NLRP3, IL-1β, IL-18, and S100A9 are commercially available and can be produced using routine skill.

Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays. Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

A modifier unit such as a radionuclide can be incorporated into or attached directly to any of the compounds described herein by halogenation. In another aspect, the radionuclide can be attached to a linking group or bound by a chelating group, which is then attached to the compound directly or by means of a linker. Radiolabeling techniques such as these are routinely used in the radiopharmaceutical industry.

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two-step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

In some aspects, the method comprises detecting gene expression for genes such as CASP-1, NLRP3, or a combination thereof, e.g., using a primer or probe that selectively binds CASP-1 or NLRP3 mRNA.

A number of widely used procedures exist for detecting and determining the abundance of a particular mRNA in a total or poly(A) RNA sample. For example, specific mRNAs can be detected using Northern blot analysis, nuclease protection assays (NPA), in situ hybridization, or reverse transcription-polymerase chain reaction (RT-PCR).

In theory, each of these techniques can be used to detect specific RNAs and to precisely determine their expression level. In general, Northern analysis is the only method that provides information about transcript size, whereas NPAs are the easiest way to simultaneously examine multiple messages. In situ hybridization is used to localize expression of a particular gene within a tissue or cell type, and RT-PCR is the most sensitive method for detecting and quantitating gene expression.

Northern analysis presents several advantages over the other techniques. The most compelling of these is that it is the easiest method for determining transcript size, and for identifying alternatively spliced transcripts and multigene family members. It can also be used to directly compare the relative abundance of a given message between all the samples on a blot. The Northern blotting procedure is straightforward and provides opportunities to evaluate progress at various points (e.g., intactness of the RNA sample and how efficiently it has transferred to the membrane). RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

The Nuclease Protection Assay (NPA) (including both ribonuclease protection assays and S1 nuclease assays) is an extremely sensitive method for the detection and quantitation of specific mRNAs. The basis of the NPA is solution hybridization of an antisense probe (radiolabeled or nonisotopic) to an RNA sample. After hybridization, single-stranded, unhybridized probe and RNA are degraded by nucleases. The remaining protected fragments are separated on an acrylamide gel. Solution hybridization is typically more efficient than membrane-based hybridization, and it can accommodate up to 100 µg of sample RNA, compared with the 20-30 µg maximum of blot hybridizations. NPAs are also less sensitive to RNA sample degradation than Northern analysis since cleavage is only detected in the region of overlap with the probe (probes are usually about 100-400 bases in length).

NPAs are the method of choice for the simultaneous detection of several RNA species. During solution hybridization and subsequent analysis, individual probe/target interactions are completely independent of one another. Thus, several RNA targets and appropriate controls can be assayed simultaneously (up to twelve have been used in the same reaction), provided that the individual probes are of different lengths. NPAs are also commonly used to precisely map mRNA termini and intron/exon junctions.

In situ hybridization (ISH) is a powerful and versatile tool for the localization of specific mRNAs in cells or tissues. Unlike Northern analysis and nuclease protection assays, ISH does not require the isolation or electrophoretic separation of RNA. Hybridization of the probe takes place within the cell or tissue. Since cellular structure is maintained throughout the procedure, ISH provides information about the location of mRNA within the tissue sample.

The procedure begins by fixing samples in neutral-buffered formalin, and embedding the tissue in paraffin. The samples are then sliced into thin sections and mounted onto microscope slides. (Alternatively, tissue can be sectioned frozen and post-fixed in paraformaldehyde.) After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while nonisotopically labeled probes are conveniently detected with colorimetric or fluorescent reagents.

RT-PCR has revolutionized the study of gene expression. It is now theoretically possible to detect the RNA transcript of any gene, regardless of the scarcity of the starting material or relative abundance of the specific mRNA. In RT-PCR, an RNA template is copied into a complementary DNA (cDNA) using a retroviral reverse transcriptase. The cDNA is then amplified exponentially by PCR. As with NPAs, RT-PCR is somewhat tolerant of degraded RNA. As long as the RNA is intact within the region spanned by the primers, the target will be amplified.

Relative quantitative RT-PCR involves amplifying an internal control simultaneously with the gene of interest. The internal control is used to normalize the samples. Once normalized, direct comparisons of relative abundance of a specific mRNA can be made across the samples. It is crucial to choose an internal control with a constant level of expression across all experimental samples (i.e., not affected by experimental treatment). Commonly used internal controls (e.g., GAPDH, β-actin, cyclophilin) often vary in expression and, therefore, may not be appropriate internal controls. Additionally, most common internal controls are expressed at much higher levels than the mRNA being studied. For relative RT-PCR results to be meaningful, all products of the PCR reaction must be analyzed in the linear range of amplification. This becomes difficult for transcripts of widely different levels of abundance.

Competitive RT-PCR is used for absolute quantitation. This technique involves designing, synthesizing, and accurately quantitating a competitor RNA that can be distinguished from the endogenous target by a small difference in size or sequence. Known amounts of the competitor RNA are added to experimental samples and RT-PCR is performed. Signals from the endogenous target are compared with signals from the competitor to determine the amount of target present in the sample.

Also disclosed herein is a kit for treating a subject with meylodysplastic syndrome (MDS), comprising an inflammasome inhibitor and an assay for detecting inflammasome activity. In one embodiment, disclosed herein is a kit for diagnosing a subject with meylodysplastic syndrome (MDS), comprising an assay for detecting inflammasome activity. In one embodiment, the assay is an immunoassay, for example, an immunoassay comprising an antibody that specifically binds CASP1, NLRP3, s100A9, or ROS. In one embodiment, the assay further comprises secondary antibodies and reagents for detecting binding of an antibody to CASP1, NLRP3, s100A9, or ROS. In one embodiment, the immunoassay comprises enzyme-linked immunosorbent assay (ELISA), immunohistochemistry, or flow cytometry.

In one embodiment, the assay comprises one or more oligonucleotides that function as primers or probes for detecting gene expression levels, for example, primers or probes for detecting gene expression levels of CASP1, NLRP3, s100A9, or ROS. In one embodiment, the oligonucleotide is conjugated to a detection label. In one embodiment, the assay further comprises polymerase chain reaction (PCR) enzymes and buffers. In one embodiment, the assay further comprises CASP1, NLRP3, s100A9, or ROS protein or cDNA to serve as a control. In one embodiment, the kit further comprises reference values of CASP1, NLRP3, s100A9, or ROS for patients with MDS and control patients without MDS.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Identification of the NLRP3 Inflammasome as a Driver of the MDS Phenotype Recent investigations indicate that activation of TLRs by specific DAMPs can trigger pyroptosis, a caspase-1-dependent pro-inflammatory cell death (Masters, S L. et al. Immunity 2012 37:1009-1023; Brennan, M A. & Cookson, B. T. Mol Microbiol 2000 38:31-40; Cookson, B T. & Brennan, M A. Trends Microbiol 2001 9:113-114). Pyroptosis differs from apoptosis by its caspase-1 dependence, activation of ion gradients resulting in cell swelling rather than condensation, and the release of IL1β intracellular DAMPs and other pro-inflammatory cytokines (Hofmann, W K. et al. Blood 2002 100:3553-3560; Masters, S L. et al. Immunity 2012 37:1009-1023; Brennan, M A. & Cookson, B. T. Mol Microbiol 2000 38:31-40; Bergsbaken, T., et al. Nat Rev Micriobiol 2009 7:99-109). Pyroptosis is mediated by the formation of inflammasome complexes, cytosolic heptameric oligomers composed of pattern recognition receptors (PRR) belonging to the nucleotide-binding domain and leucine-rich repeat receptor (NLR) family. The best characterized NLRs, NLRP1 and NLRP3, undergo a conformational change in response to DAMP interaction to recruit an adapter protein and caspase-1, which in turn catalyzes proteolytic cleavage of pro-IL-1β & pro-IL-18 to their active forms (Fantuzzi, G. & Dinarello, C A. J Clin Immunol 1999 19:1-11). NLRP3 inflammasome activation involves two steps that begins with NFκB induced transcriptional priming of inflammasome components, followed by cation channel activation with cell volume expansion and inflammasome component assembly (Latz, E., et al. Nat Rev Immunol 2013 13:397-411; Barbe, F., et al. Cytokine Growth Factor Rev 2014 25(6):681-97). Intracellularly, S100A9 homodimers and S100A8 heterodimers act as regulators of intracellular NADPH oxidase to generate reactive oxygen species and activate inflammasome assembly, while serving as paracrine inflammatory signals extracellularly (Kessel, C., et al. Clin Immunol 2013 147:229-241; Lim, S Y., et al. J Leukoc Biol 2009 86:577-587; Simard, J C. et al. PLoS One 2013 8(8):e72138). The principal cellular consequence of inflammasome activation is pyroptosis, resulting in the elaboration of inflammatory cytokines and intracellular oxidative intermediates (Lamkanfi, M. & Dixit, V M. Cell 2014 157:1013-1022; Lamkanfi, M. Nat Rev Immunol 2011 11:213-220).

S100A9, coupled with reactive oxygen species (ROS) generated in response to PRR activation or somatic gene mutations, is shown to serve as DAMP signaling intermediates responsible for inflammasome-mediated pyroptosis and β-catenin activation, accounting for key biological features of the MDS phenotype.

Methods

MDS Patient Specimens.

MDS patients consented on The University of South Florida Institutional Review Board approved protocols were recruited from the Malignant Hematology Clinic at H. Lee Moffitt Cancer Center & Research Institute, and the Eastern Cooperative Oncology Group (ECOG) E2905 trial (NCT00843882). Pathologic subtype of MDS was reported according to World Health Organization (WHO) criteria and prognostic risk assigned according to the International Prognostic Scoring System (IPSS). Patients were segregated as lower (Low, Intermediate-1) and higher risk (Intermediate-2, High) MDS. Bone marrow mononuclear cells (BM-MNC) were isolated from heparinized bone marrow aspirates using Ficoll-Hypaque Plus gradient centrifugation (GE Healthcare).

Mice.

S100A9Tg mice were used for animal studies (Chen X, et al. J Clin Invest. 2013 123(11):4595-611). WT FVB/NJ mice were purchased from Jackson Laboratories (Bar Harbor, Me.). Heparinized BM cells were isolated from tibias and femurs of male and female mice.

Reagents and Cells.

U937 cells were grown in RPMI1640 supplemented with 10% FBS. TF-1 U2AF1 mutant and mock WT cells were cultured in RPMI1640 supplemented with 10% FBS and 2 ng/mL recombinant human GM-CSF. Cells were maintained at 37° C. under 5% $CO_2$. Normal, heparinized BM aspirates were purchased from Lonza Walkersville or AllCells, LLC. Normal and MDS bone marrow mononuclear cells (BM-MNC) were isolated from heparinized bone marrow aspirates using Ficoll-Hypaque Plus gradient centrifugation (GE Healthcare). Recombinant human S100A9 and the CD33/Siglec 3 chimeric fusion protein were generated as previously described (Chen X, et al. J Clin Invest. 2013 123(11): 4595-611). The IRAK4 inhibitor was acquired through material transfer agreement from Nimbus Discovery. NAC and DPI were purchased from Sigma-Aldrich. Active caspase-1 and caspase-3/7 were detected using FAM-FLICA® Caspase-1 and Caspase-3/7 activity kits, (ImmunoChemistry Technologies). NLRP1 antibodies were purchased from Santa Cruz Biotechnology, NLRP3 antibodies from Abcam, and β-catenin antibodies from BD Biosciences. Caspase-1 and TXNIP antibodies were purchased from Cell Signaling Technology, Inc. (#3866 and #14715, respectively). IL-1β antibodies were acquired from R&D Systems, Inc. (AF-201-NA) and POP-1 antibodies from OriGene Technologies, Inc. (TA803612).

Pyroptosis Flow Cytometry Panel.

For human samples, treated and untreated BM-MNC were incubated overnight in IMDM, supplemented with 10% autologous BM plasma. Subsequently, cells were harvested, washed twice in 1×PBS, and stained with LIVE/DEAD Violet fluorescent reactive dye according to the manufacturer's protocol (Life Technologies). Cells were resuspended in 1×PBS with 2% BSA, and incubated at room temperature for 15 minutes to block non-specific binding. After washing, cells were stained with 30×FAM-FLICA® Caspase-1 and Caspase-3/7 solution at a ratio of 1:30 for 2 hours at 37° C. Cells were washed and stained for cell surface receptors using CD38:PE-CF594, CD33:BV711, CD34:APC (BD Biosciences), and CD71:PE-Cyanine7 (eBioscience). All antibodies were diluted 1:20, and cells were stained for 30 minutes at 4° C. Cells were washed, resuspended in 1× binding buffer, and stained with Annexin-V:Cy5.5 at a dilution of 1:20 for 15 minutes at room temperature (BD Biosciences). 1× binding buffer was added to a final volume of 400 µL. Sample acquisitions were carried out using a BD LSR II flow cytometer and FACSDiva software (BD Biosciences). Calibration of the flow cytometer was carried out prior to each experiment using Rainbow Mid-Range Fluorescent Particles (BD Biosciences). To establish fluorescence compensation settings, ArC Amine Reactive Compensation Beads were used for LIVE/DEAD Violet staining (Life Technologies), and BD CompBead Plus Anti-Mouse Ig κ/Negative Control (BSA) Compensation Plus Particles were used for surface receptor conjugates (BD Biosciences). Data were analyzed using FlowJo 9.7.5 software (FlowJo, LLC, Ashland, Oreg.).

S100A9 Flow Cytometry Experiments in U937 Cells.

Monocytic U937 cells were treated with the indicated concentrations of rhS100A9 for 24 hours, or with 5 µg/mL rhS100A9 for the indicated time points. Subsequently, cells were stained with 30×FAM-FLICA® Caspase-1 solution at a ratio of 1:30 for 2 hours at 37° C. Cells were washed, resuspended in 1× binding buffer, and stained with Annexin-V:PE at a dilution of 1:30 for 15 minutes at room temperature. 1× binding buffer was added to a final volume of 350 µL. Sample acquisitions were carried out using a BD FACSCalibur flow cytometer (BD Biosciences). Data were analyzed using FlowJo 9.7.5 software.

Intracellular S100A9 Flow Cytometry.

BM-MNC were incubated overnight in IMDM, supplemented with 10% autologous BM plasma. The following day, cells were harvested and washed twice in 1×PBS. Cells were fixed with BD Cytofix Fixation Buffer at 37° C. for 10 minutes, and stored at −80° C. until staining. At the time of staining, cells were warmed to 37° C. in a water bath, spun down, and washed 1× with staining buffer. Pellets were resuspended in 1 mL of pre-warmed BD Permeabilization Buffer III, and incubated on ice for 30 minutes. Cells were washed twice with staining buffer. Following washing, cells were stained with S100A9:FITC (BioLegend), and cell surface receptors using CD38:PE-CF594, CD33:BV711, CD34:APC (BD Biosciences), and CD71:PE-Cyanine7 (eBioscience). All antibodies were diluted 1:20, and cells were stained for 30 minutes at 4° C. Cells were washed and resuspended in 400 µL staining buffer. Sample acquisitions were carried out using a BD LSR II flow cytometer and FACSDiva software (BD Biosciences).

Enzyme-Linked Immunosorbent Assays (ELISA).

Human S100A9 DuoSet ELISA kit was purchased from R&D Systems and HMGB1 ELISA kit was purchased from MYBioSource. Both were performed according to manufacturer's protocol.

Immunofluorescence Confocal Microscopy.

MDS and normal donor BM-MNC and mouse BM cells were stained with 30×FAM-FLICA® Caspase-1 solution at a ratio of 1:30 for 2 hours at 37° C. Cells were washed and cytospins were generated using a 5 minutes centrifugation at 450 rpm. Slides were fixed at 37° C. for 10 minutes using BD Cytofix Fixation Buffer (BD Biosciences), and subsequently washed using PBS. Cells were permeabilized with 0.1% Triton X-100/2% BSA in PBS for 15 minutes at room temperature. After washing with PBS, cells were blocked using 2% BSA in PBS for 30 minutes at room temperature, and washed again. Cells were incubated with the appropriate primary antibody overnight (1:400 for NLRP3, 1:20 for β-catenin) at 4° C. The next day, cells were washed with PBS and incubated with the appropriate secondary antibodies (1:500) for 1 hour at room temperature. After washing, cells were covered with ProLong Gold Antifade Reagent with DAPI prior to the addition of a coverslip (Life Technologies). Co-localization of a-caspase-1 with NLRP3 inflammasome complexes was assessed using a Leica TCS SP5 AOBS Laser Scanning Confocal microscope (Leica Microsystems). Analysis of the inflammasome images was performed with Definiens Developer 2.0 (Definiens AG). The software was used to segment cells based on brightness and size thresholds, followed by a watershed segmentation algorithm. Intensity values and Pearson's correlation coefficient were extracted from the segmented cells. For β-catenin image analysis, confocal images were imported into Definiens Tissue Studio v3.0, 64 Dual in .tif format. Cells were separated from background using the RGB thresholds. Nuclei were identified by setting thresholds in the DAPI channel. Typical cells averaged 60 microns. The red intensity (β-catenin) in the nucleus and cytoplasm was established by setting thresholds to low, medium and high in the red channel on a scale of 0-255 in the red channel.

ASC Staining to Detect Inflammasome Formation by Flow Cytometry.

Staining was carried out as described (Sester D. P, et al. J Immunol. 2015 194(1):455-62). Briefly, cell pellets were resuspended in 1 mL of prewarmed BD Permeabilization Buffer III, and incubated on ice for 30 minutes. Cells were washed 2× with staining buffer. Following washing, cells were stained with rabbit-anti-ASC primary antibodies at a 1:1500 dilution and incubated for 90 minutes. Cells were washed, stained with secondary antibodies at a dilution of 1:1500, and incubated for 45 minutes. Cells were washed, and sample acquisitions were carried out using a BD LSR II flow cytometer and FACSDiva software.

ASC Speck Detection.

400 µg of protein was aliquoted from BM plasma from normal donors and MDS patients, stained with rabbit-anti-ASC primary antibodies at a 1:1500 dilution and incubated for 90 minutes. Secondary antibodies were added at a dilution of 1:1500 and incubated for 45 minutes. Sample acquisitions were carried out using a BD FACSCalibur flow cytometer. Threshold for FSC, SSC and the secondary fluorochrome was set to zero to allow detection of specks.

Real-Time Quantitative

PCR RNA was isolated from BM-MNC using the RNeasy Mini Kit (Qiagen). cDNA was produced using the iScript cDNA Synthesis Kit (Bio-Rad). Sequences for primers can be found in Table 1. GAPDH mRNA was used for transcript normalization. cDNA was amplified using the iQ SYBR Green Supermix and the CFX96 Real-Time PCR Detection System (Bio-Rad). PCR conditions were as follows: 10 minutes at 95° C., followed by 40 cycles of amplification (15 seconds at 95° C. and 1 minute at 60° C.). Relative gene expression was calculated using the $-2^{\Delta\Delta Ct}$ method.

TABLE 1

Primer sets used for qPCR.

| Gene | Forward | |
|---|---|---|
| CASP1 | 5'-TGAGCAGCCAGATGGTAGAGC-3' | SEQ ID NO: 1 |
| CASP3 | 5'-GTGAGGCGGTTGTAGAAGAGTTTC-3' | SEQ ID NO: 2 |
| IL-1β | 5'-CTCTTCGAGGCACAAGGCAC-3' | SEQ ID NO: 3 |
| IL-18 | 5'-ACTGCCTGGACAGTCAGCAA-3' | SEQ ID NO: 4 |
| NLRP1 | 5'-TCTACGTTGGCCACTTGGGA-3' | SEQ ID NO: 5 |
| NLRP3 | 5'-CAATGGGGAGGAGAAGGCGT-3' | SEQ ID NO: 6 |
| S100A9 | 5'-CTCGGCTTTGACAGAGTGCAA-3' | SEQ ID NO: 7 |
| HMGB1 | 5'-CCCTCCCAAAGGGGAGACAAA-3' | SEQ ID NO: 8 |
| GAPDH | 5'-GAAGGTGAAGGTCGGACT-3' | SEQ ID NO: 9 |
| | Reverse | |
| CASP1 | 5'-TCACTTCCTGCCCACAGACAT-3' | SEQ ID NO: 10 |
| CASP3 | 5'-TGAGCAGGGCTCGCTAACTC-3' | SEQ ID NO: 11 |
| IL-1β | 5'-CAAGTCATCCTCATTGCCACTGT-3' | SEQ ID NO: 12 |
| IL-18 | 5'-GCAGCCATCTTTATTCCTGAGA-3' | SEQ ID NO: 13 |
| NLRP1 | 5'-AGAGGTGAAGGTACGGCTATGC-3' | SEQ ID NO: 14 |
| NLRP3 | 5'-TCTGAACCCCACTTCGGCTC-3' | SEQ ID NO: 15 |
| S100A9 | 5'-CTGGTTCAGGGTGTCTGGGT-3' | SEQ ID NO: 16 |
| HMGB1 | 5'-AGAGGAAGAAGGCCGAAGGAG-3' | SEQ ID NO: 17 |
| GAPDH | 5'-GAAGATGGTGATGGGATTTC-3' | SEQ ID NO: 18 |

Lentiviral Infection of Primary Mononuclear Cells.

Lentiviral constructs were purchased from Origene. Caspase-1 (TL305640), Caspase-3 (TL305638b), and scrambled (TR30021) HuSH™ shRNA plasmids were amplified by transforming One Shot® Top 10 competent cells (Life technologies) according to manufacturer's protocol. Single colonies were expanded and mini preps were performed using the Qiagen QIAprep® Mini Prep Kit. HEK293T cells were transfected by incubating 2600 ng of shRNA plasmid, 30 µL Lipofectamine® 2000 (Invitrogen), 26 µL MISSION™ Lentiviral Packaging Mix (Sigma Aldrich) in 500 µL of Opti-MEM®I (Life technologies) for 15 minutes at room temperature. This mixture was then added to 70% confluent HEK293T cells with 4 mL Opti-MEM®I medium without serum in a 100 mm dish. Cells were incubated at 37° C. for 6 hours in a humidified chamber, then 6 mL of DMEM (Mediatech, Manassas, Va.) with 10% serum was added. In the morning, medium was changed and 10 mL fresh DMEM was added. Virus was collected at 48 and 72 hours using 0.45 µm filters. The concentration was determined to be at least $5 \times 10^5$ IFU/mL using Clontech Lenti-X Go Stix (Mountain View, Calif.) and stored at 4° C. Virus up to one week old was used for experiments. For primary cell infection, 2.5 million cells were plated in a 100 mm dish with 1.25 mL fresh virus, 1.25 mL opti-MEM®I, and 8 pig/mL polybrene. Cells were incubated overnight, then 5 mL of fresh IMDM (Mediatech) with 10% FBS was added. RNA was isolated after 72 hours of infection using Qiagen RNeasy Isolation Kit according to manufacturer's protocol and mRNA levels were analyzed by qPCR using GAPDH mRNA levels as a control. Additionally at 72 hours, 10% v/v of autologous BM plasma was added to the remaining cells. Twenty-four hours after plasma was added, cells were stained with annexin-V, 7-AAD, and FAM-FLICA® Caspase-1 and analyzed using a BD FACSCalibur flow cytometer.

Colony Formation Assay.

Four replicates of 350,000 BM-MNC/mL were resuspended in 10% autologous BM plasma and plated in MethoCult methylcellulose medium (Stemcell Technologies) supplemented with 1% v/v penicillin-streptomycin and 3 units/mL erythropoietin. CD33-IgG and MCC950 were added directly to the medium prior to plating. Colonies of BFU-E, CFU-GM, and CFU-GEMM were scored using an inverted light microscope fourteen days after plating.

SRSF2 Transfection of HEK293T Cells.

HEK293T cells were transfected by incubating 4 µg of SRSF2 DNA with 10 µL Lipofectamine® 2000 in 100 µL of Opti-MEM®I for 20 minutes at room temperature. This mixture was added to 70% confluent HEK293T cells with 2 mL Opti-MEM®I medium without serum in a 6 well plate. Cells were incubated at 37° C. for 4 hours in a humidified chamber, then medium was replaced with 2 mL of DMEM with 10% serum added. Treatment with NAC or DPI and subsequent analyses were carried out 24 and 48 hours following transfection, respectively.

Pore Formation Assay.

MDS and normal donor BM-MNC were incubated in 10% autologous BM plasma at 37° C. overnight. Cells were subsequently washed and resuspended in 1 mL of PBS. 12.5 µg/mL ethidium bromide (Fisher Scientific, Pittsburgh, Pa.) was added, and sample acquisitions were acquired at the indicated time points using a BD FACSCalibur flow cytometer.

ROS Detection.

ROS were detected using CM-H$_2$DCFDA and CellROX® Deep Red Reagent according to manufacturer's protocol (Life Technologies).

Comet Assays.

Monocytic U937 cells were treated with 5 µg/mL rhS100A9 for 24 hr.

DNA damage was measured by single cell gel electrophoresis using alkaline CometAssay® according to manufacturer's protocol (Trevigen Inc.).

POP-1 Overexpression.

PYDC1 expression (RC211240) and empty control (PS100001) vectors were purchased from Origene Technologies, Inc. 5 µg of plasmid was added to 6 million cells suspended in 100 µL electroporation solution (Ingenio® Solution, Mirus Bio LLC.) and electroporated using an Amaxa Nucleofector® program T-20 (Lonza Cologne AG, Germany). Cells were resuspended in 30 mL of appropriate growth medium. Expression and functional assays were performed 48 hr after transfection.

Immunoblotting.

U2AF1 S34F cells were treated for 24 hr as indicated, then harvested. Normal and lower-risk MDS BM-MNC were thawed and pelleted. Samples were lysed in 1×RIPA buffer (250 µM $NaOV_4$, 2 µg/mL aprotinin, 2 µg/mL leupeptin, 0.2 µg/mL pepstatin A and 500 µM PMSF), and proteins were resolved by SDS-PAGE and transferred to PVDF membranes. Membranes were blocked for 30 min in 5% dry milk PBST solution (1×PBS, Tween®20), and incubated overnight with the indicated antibody. For caspase-1 detection, the membrane and indicated antibody was incubated in TBST solution (1×TBS, 5% w/v BSA, 0.1% Tween®20). The next day, membranes were washed and secondary antibodies were incubated for three hours. Membranes were developed using ECL or ECL+ according to manufacturer's protocol (Thermo Scientific).

Immunoprecipitation.

Following lysis, 200 µg of protein were incubated with 2 µg of the indicated antibody on ice for 2 hr. Next, 50 µL of Protein A Agarose beads (EMD Millipore) were added to each condition, and bead-lysate slurries were incubated overnight at 4° C. on a rotator. The next day, samples were washed with 500 µL of lysis buffer three times. Beads were dissociated at 95° C. for 5 min following addition of sample buffer. Proteins were separated by SDS-PAGE and immunoblotted accordingly.

Next-Generation Sequencing and Mutation Identification.

DNA was extracted from peripheral blood and bone marrow samples. Target amplification of DNA for each sample was performed using the GeneRead DNAseq Panel PCR Kit V2 (Qiagen, Valencia, Calif.). Target regions of 26 common genes and genotype fingerprint regions were enriched using the Human Colorectal Cancer Panel according to manufacturer instructions (Qiagen). Samples were barcoded using NEXTflex-96™ DNA Barcodes (Bioo Scientific) and pooled in equal amounts before running on an Illumina MiSeq 2000. Sequence reads were aligned to the human genome using the GeneRead Targeted Exon Enrichment Panel Data Analysis (Qiagen). Sample data with synonymous variants, noncoding variants, and variants present in databases of normal genomes (i.e., ESP6500) were discarded. Remaining variants were filtered to contain more than 50× coverage and variant frequencies greater than 0.2. Of these variants, those that were present in COSMIC, or those not present in COSMIC but having SIFT scores ≤0.05 and Polyphen scores ≥0.909, were considered candidate somatic mutations.

Statistics.

Data are expressed as means±standard error. Statistical analyses were carried out in Microsoft Excel using student's t-test, correlations using chi square for non-continuous variables and logistic regression for continuous variables were performed using IPSS software v22 (SPSS Inc., Chicago, Ill.), and *p values <0.05, p<0.01, and *p<0.01 were considered to be statistically significant.

Results

MDS HSPC Manifest Inflammasome Activation and Pyroptosis

Figure 1:
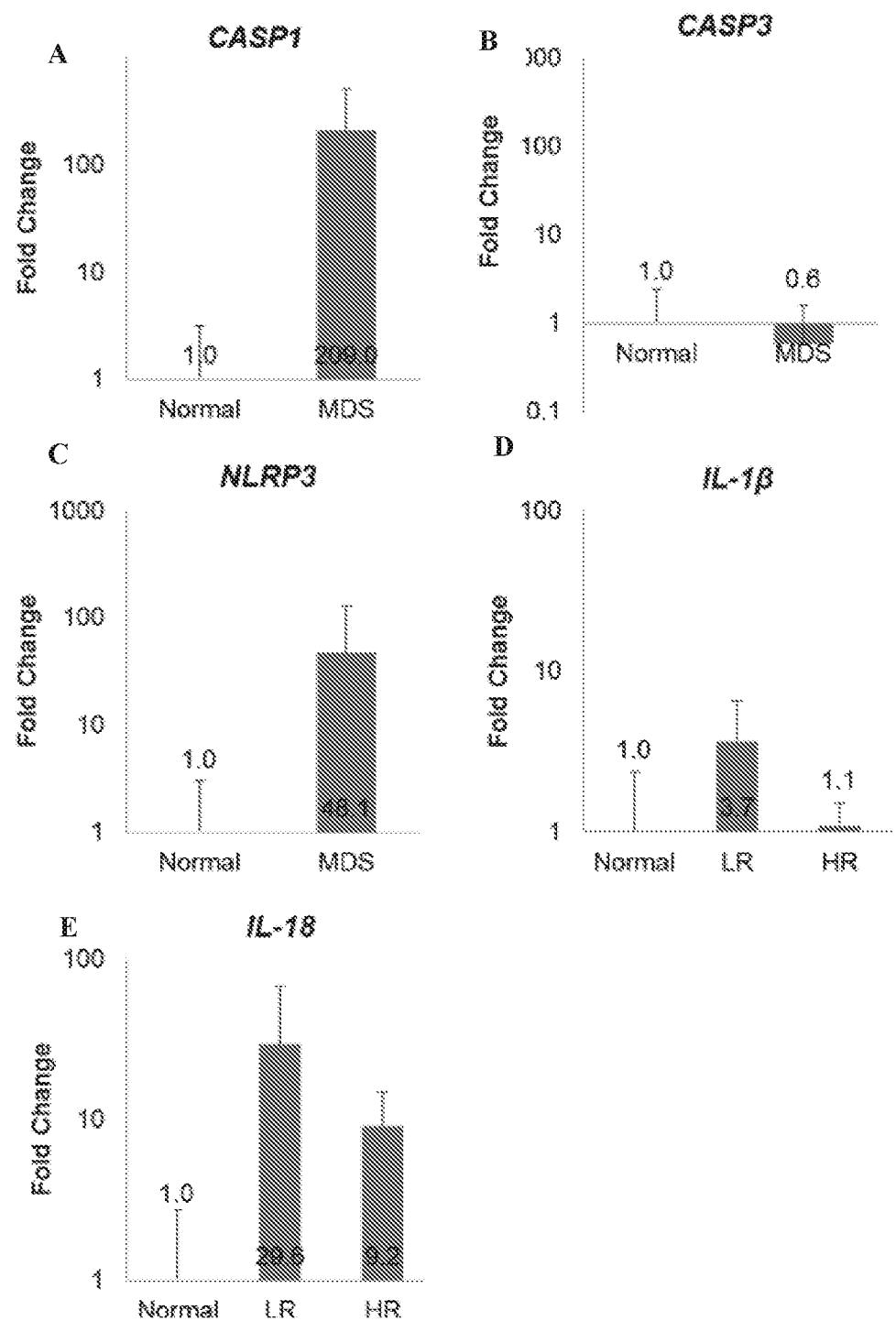
FIGS. 1-7 show that fulminant pyroptosis is manifest in hematopoietic stem/progenitor cells (HSPC) and their progeny in myelodysplastic syndromes (MDS). Error bars: SE, *$p<0.05$, $p<0.01$, and *$p<0.001$.
Figure 2:
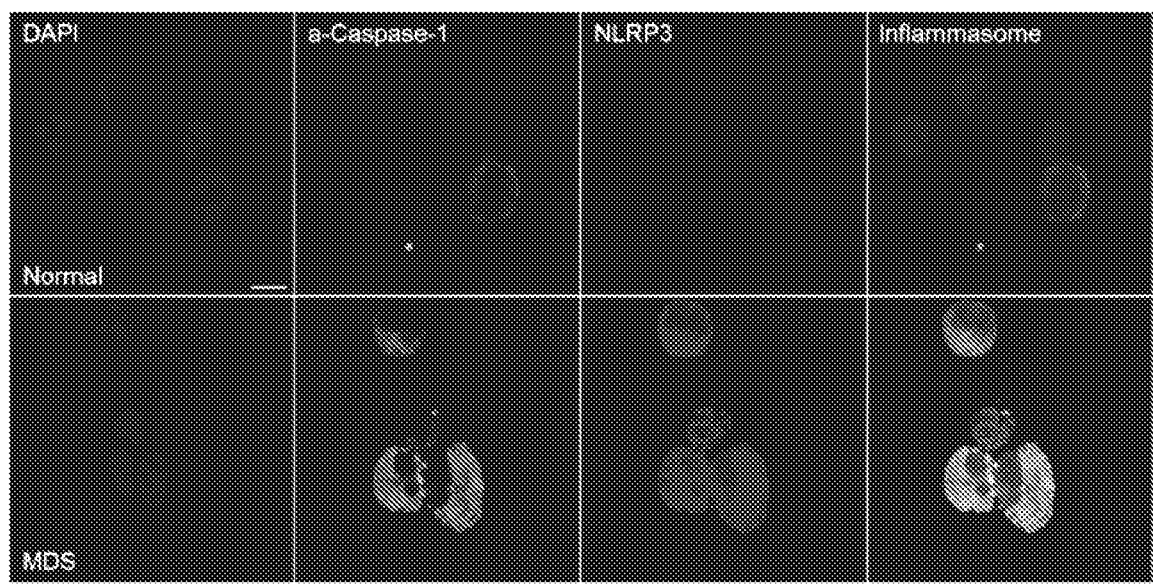
Figure 3:
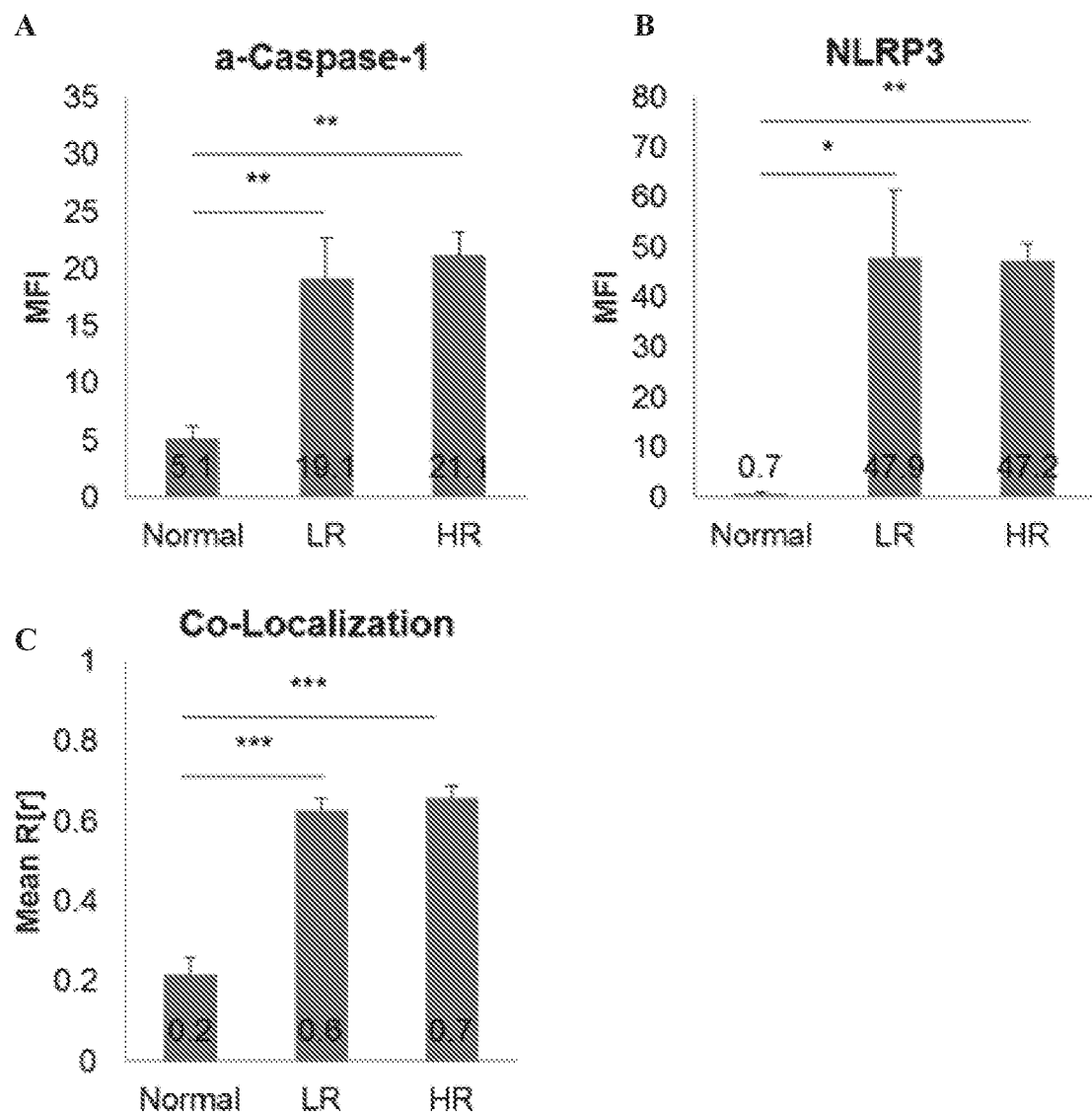

To assess whether pyroptosis was primed in MDS, expression of genes encoding inflammasome proteins was evaluated in bone marrow (BM) mononuclear cells (BM-MNC) isolated from MDS patients (n=10) compared to age-matched normal controls (n=5). MDS specimens displayed marked up-regulation of inflammasomal transcripts (FIG. 1). For example, caspase-1 (CASP1) gene expression was increased 209-fold in MDS, whereas caspase-3 (CASP3), the canonical apoptotic caspase, was 40% lower in MDS compared to normal controls. Gene expression of NLRP3 was increased 48.1-fold in MDS. Further, the expression of the inflammatory cytokines IL-1β and IL-18 was increased 3.7-fold and 29.6-fold in lower-risk MDS (n=5) compared to normal controls (n=5), whereas higher-risk MDS specimens demonstrated only 1.1-fold and 9.2-fold up-regulation (n=5), consistent with the known up-regulation of survival signals in higher risk MDS. Confocal fluorescence microscopy confirmed selective activation of NLRP3 inflammasome complexes in MDS specimens versus age-matched control BM-MNC, where there was co-localization and increased active (a)-caspase-1 (MFI increased 3.7-fold in lower-risk [$p=7.1\times10^{-3}$] and 4.1-fold in higher-risk disease [$p=6.0\times10^{-3}$]) and NLRP3 (MFI was increased 69.1-fold in lower-risk [p=0.013] and 68.2-fold in higher-risk [$p=5.1\times10^{-3}$]) disease (FIG. 2, 3). MDS specimens also displayed significantly greater inflammasome assembly compared to controls, irrespective of IPSS risk group (FIG. 3). Specifically, NLRP3 inflammasome assembly was increased 2.9-fold in lower-risk ($p=3.9\times10^{-5}$) and 3.1-fold in higher-risk ($p=7.1\times10^{-5}$) patients.

Figure 4:
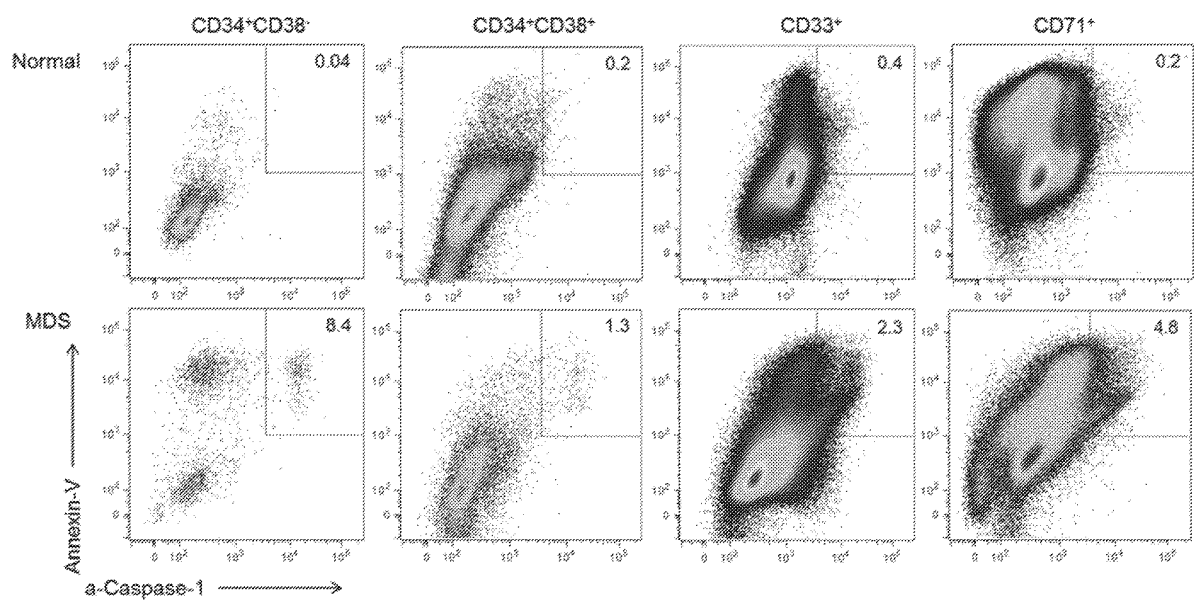
Figure 5:
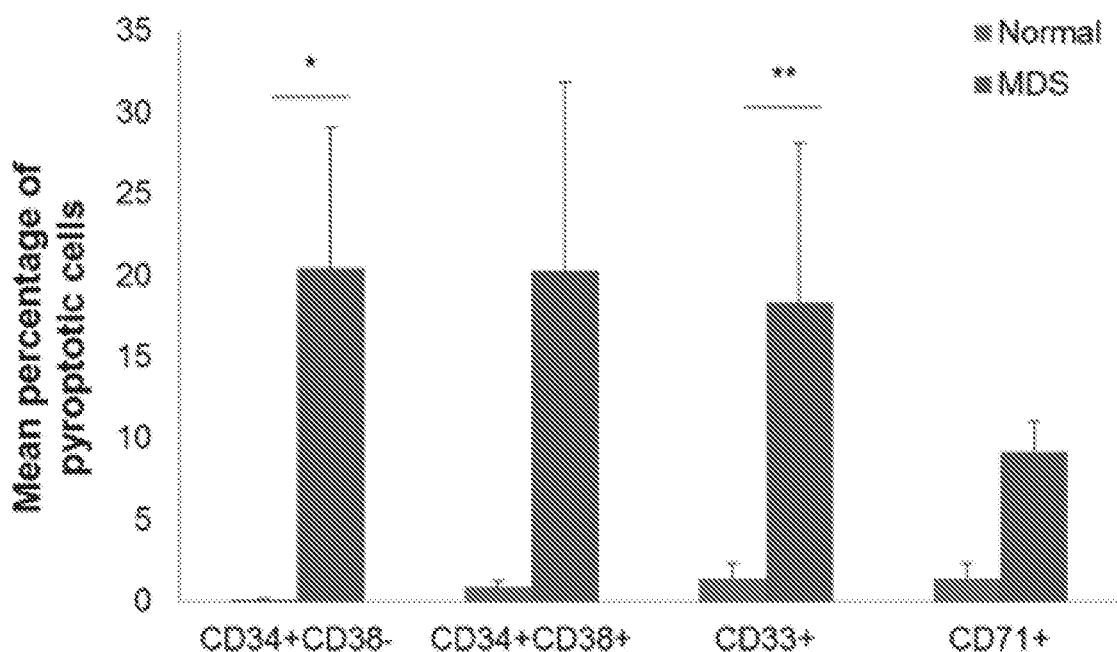
Figure 6:
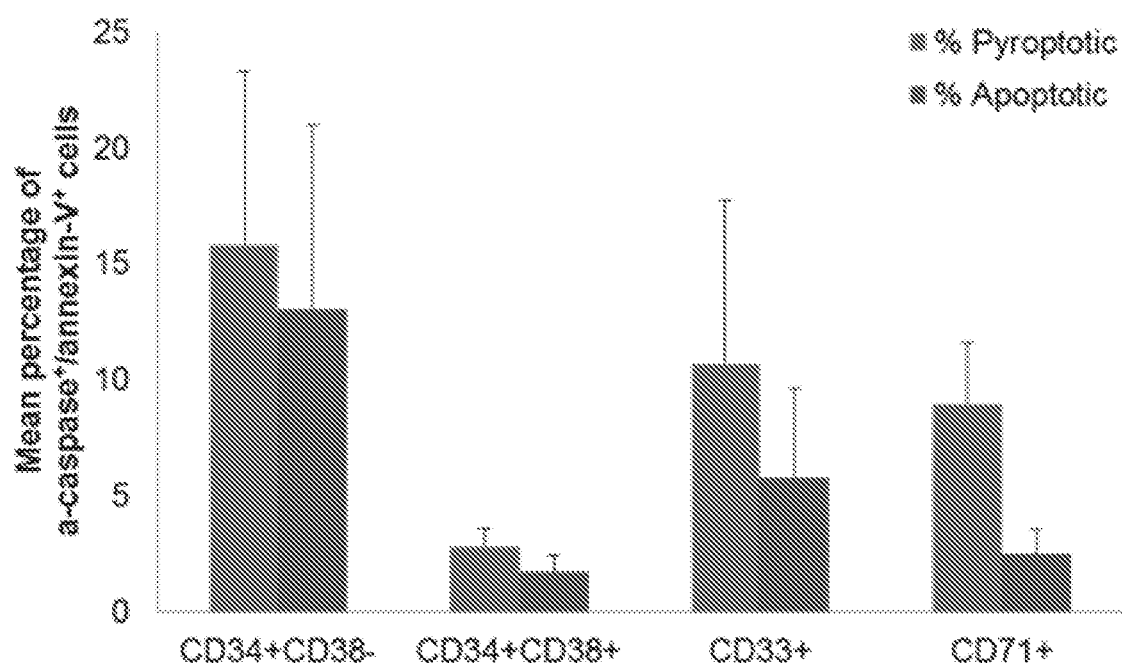
Figure 7:
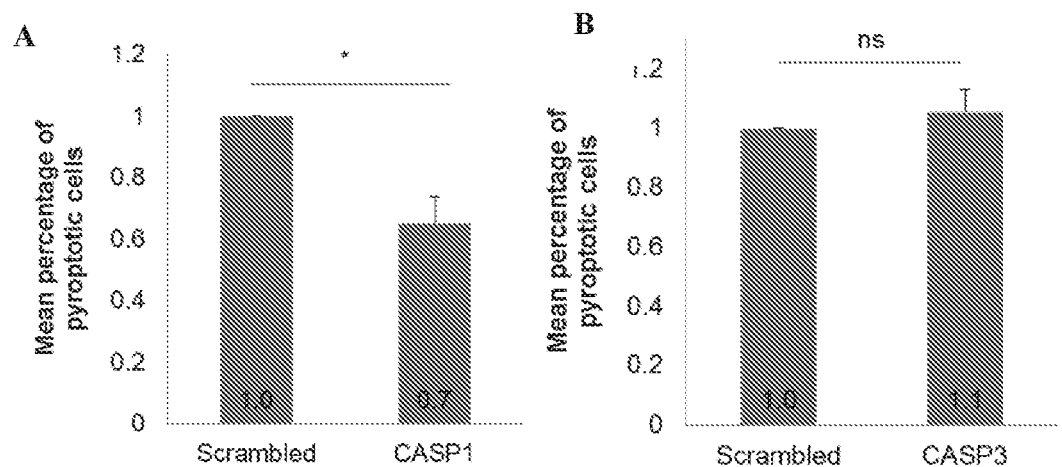
Figure 39:
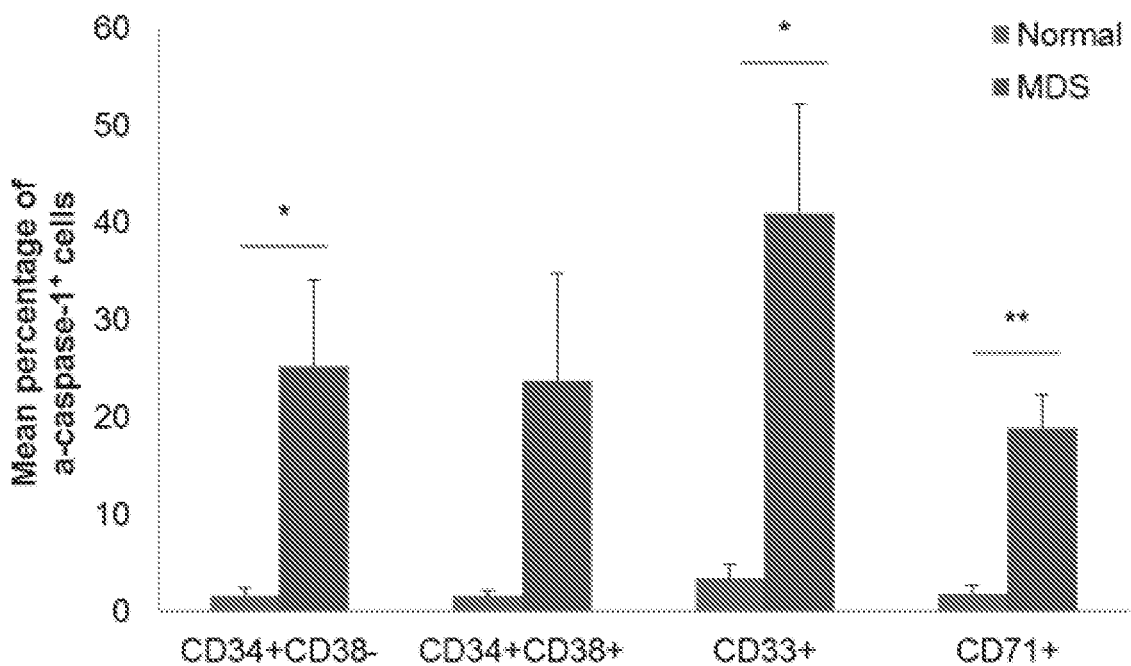
FIGS. 39-41 show that caspase-1 activation exceeds caspase-3 activation in MDS.
Figure 40:
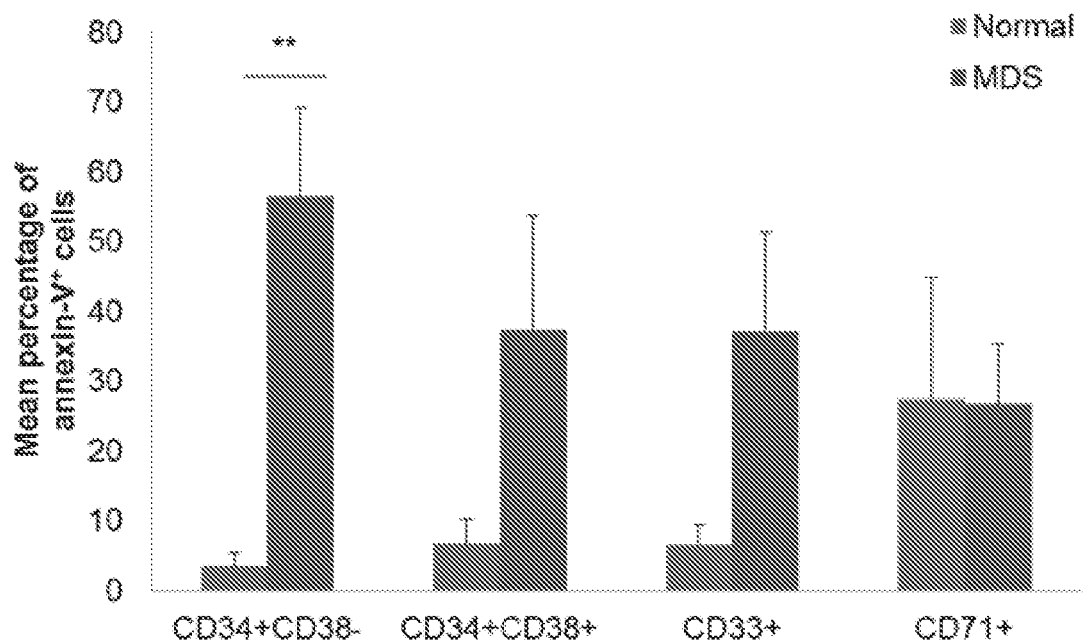
Figure 41:
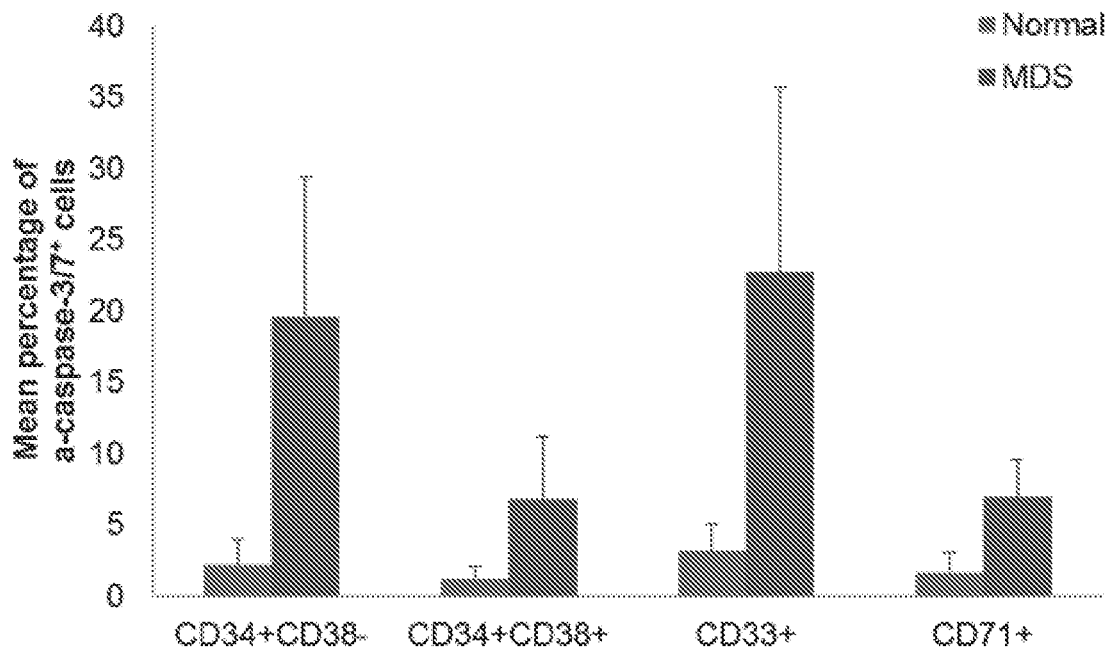
Figure 42:
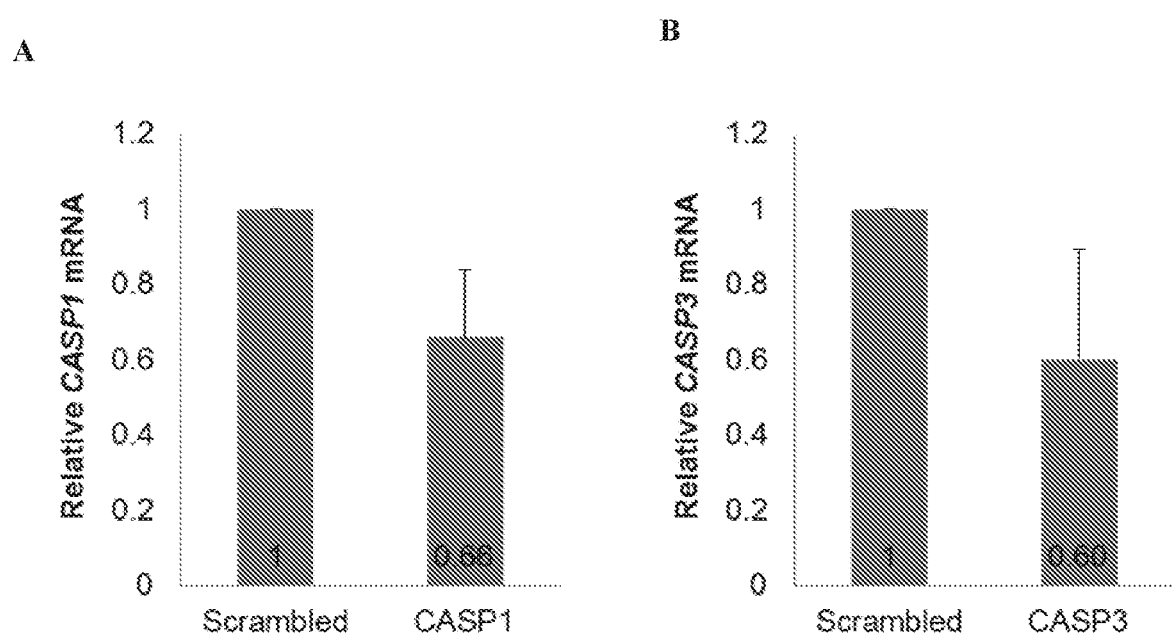
FIG. 42. Gene expression following lentivirus-mediated transfection of MDS BM-MNC. Gene expression of (A) CASP1 and (B) CASP3 was assessed by qPCR following shRNA-directed silencing performed by lentivirus transfection of lower-risk BM-MNC (n=3).

To assess pyroptosis in MDS, the percentage of pyroptotic cells, defined as percentage of a-caspase-$1^+$/annexin-$V^+$ cells, was determined in phenotypically distinct hematopoietic lineages by flow cytometry. Normal (n=5) and lower-risk MDS BM-MNC (n=8) were incubated with autologous BM plasma for 24 hours prior to flow cytometry analysis. MDS HSPC demonstrated markedly increased pyroptosis (FIG. 4), where the fraction of pyroptotic cells increased 150-fold in $CD34^+CD38^-$ stem cells (p=0.051), 22.8-fold in progenitor cells ($CD34^+CD38^+$), 13.0-fold in immature myeloid cells ($CD33^+$), and 6.8-fold in erythroid cells ($CD71^+$, $p=3.1\times10^{-3}$), compared to normal controls (FIG. 5). Additionally, the percentage of a-caspase-$1^+$ cells was increased 15.6-fold in hematopoietic stem cells (p=0.032), 14.1-fold in progenitors, 12.1-fold in immature myeloid cells (p=0.012), and 10.1-fold in $CD71^+$ cells ($p=1.5\times10^{-3}$) (FIG. 39). Overall, only the stem cell population had a significant increase in total annexin-W cells ($p=3.8\times10^{-3}$) (FIG. 40). A-caspase-1 MFI directly correlated with NLRP3 MFI, inflammasome assembly, and the percentage of pyroptotic stem cells. Notably, the latter was directly associated with the percentage of a-caspase-1 CD33 myeloid progenitors. The extent of apoptosis (i.e., a-caspase-3/$7^+$/annexin-$V^+$) was also evaluated in lower-risk MDS specimens (n=5). Pyroptotic cells were 1.2-fold, 1.6-fold, 1.9-fold, and 3.6-fold up-regulated in stem cells, progenitor cells, immature myeloids, and erythroid cells, compared to the apoptotic cell fraction (FIG. 6). No significant differences in a-caspase-3/$7^+$ cells were detected in any of the four hematopoietic lineages investigated (FIG. 41). Lastly, to confirm that caspase-1 is essential for hematopoietic cell death in MDS, shRNA-directed silencing of caspase-1 and caspase-3 was performed by lentivirus transfection of lower-risk BM-MNC (n=3) (FIG. 42). Knockdown of caspase-1 significantly decreased the fraction of pyroptotic cells, greater than 35% versus scrambled transfected controls (p=0.038) (FIG. 7A). In contrast, knockdown of caspase-3 had no discernible effect (FIG. 7B), confirming selective caspase-1-dependence.

Figure 94:
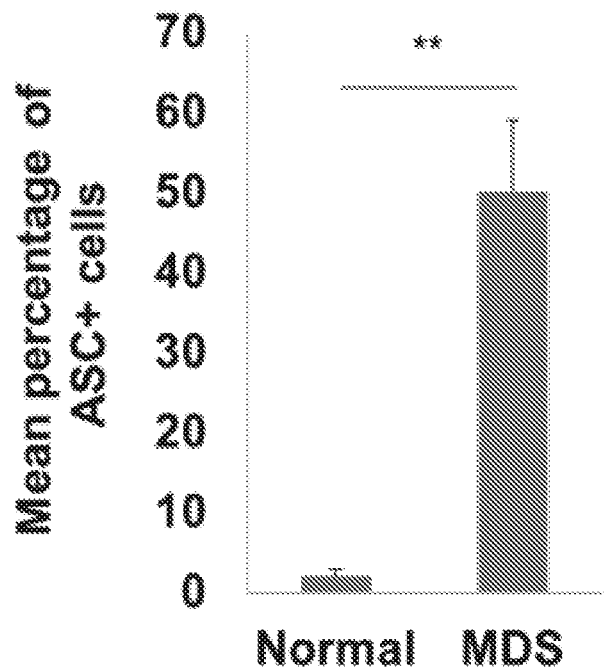
FIG. 94. Quantitation of inflammasome activation based on ASC oligomerization in BM-MNC from lower-risk MDS (n=5) versus normal donors (n=3).
Figure 95:
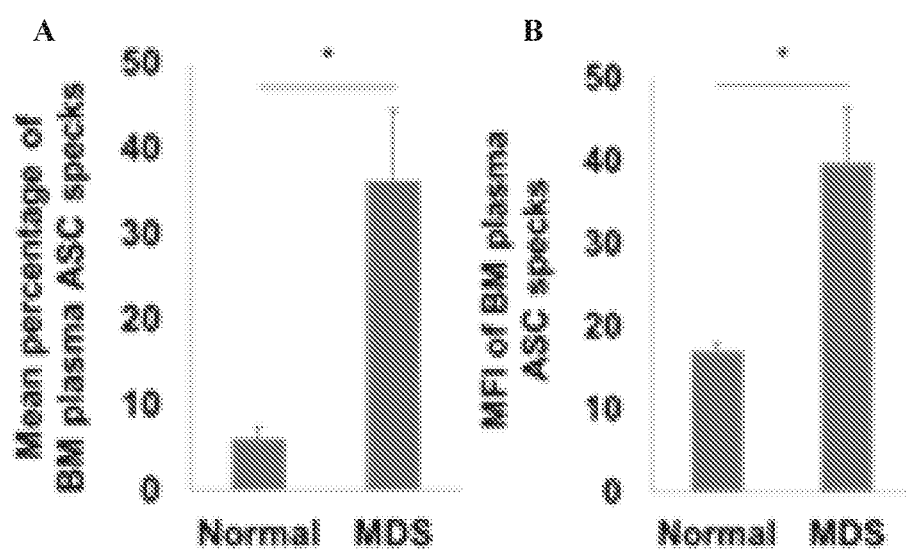
FIG. 95. Mean percentage (A) of ASC specks and (B) speck MFI in the BM plasma of lower-risk MDS specimens (n=6) compared to normal donors (n=3).

Inflammasome formation was confirmed by assessment of ASC oligomerization, whose incorporation into inflammasome complexes can be detected by flow cytometric changes in fluorescence pulse height and area (FIG. 94). MDS specimens also displayed significantly greater inflammasome assembly compared to controls, irrespective of IPSS risk group (FIG. 3). Specifically, NLRP3 inflammasome assembly was increased 2.9-fold in lower-risk ($p=3.9\times10^{-5}$) and 3.1-fold in higher-risk ($p=7.1\times10^{-5}$) MDS patients. Notably, active ASC specks are released into the extracellular space following cytolysis and specifically following execution of the pyroptotic cascade. Analysis of ASC specks in BM plasma from lower-risk MDS specimens (n=6) confirmed a profound increase in the percentage of ASC specks in MDS compared to normal donors (n=3) (mean, MDS 36.2±1.4 vs. 6.0±8.4) (FIG. 95). Finally, immunofluorescence and flow cytometry analyses of other hematologic malignancies suggest that inflammasome activation is specific for MDS (FIG. 94).

Figure 96:
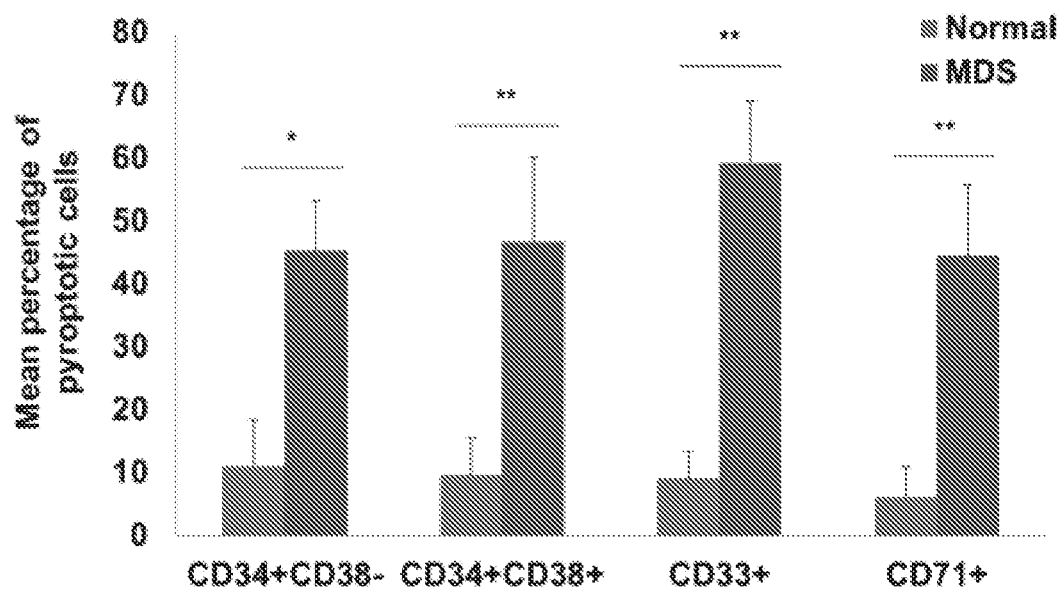
FIG. 96. Quantitation of the mean percentage of pyroptotic cells by hematopoietic lineage in lower-risk MDS (n=8) versus normal donors (n=8).
Figure 97:
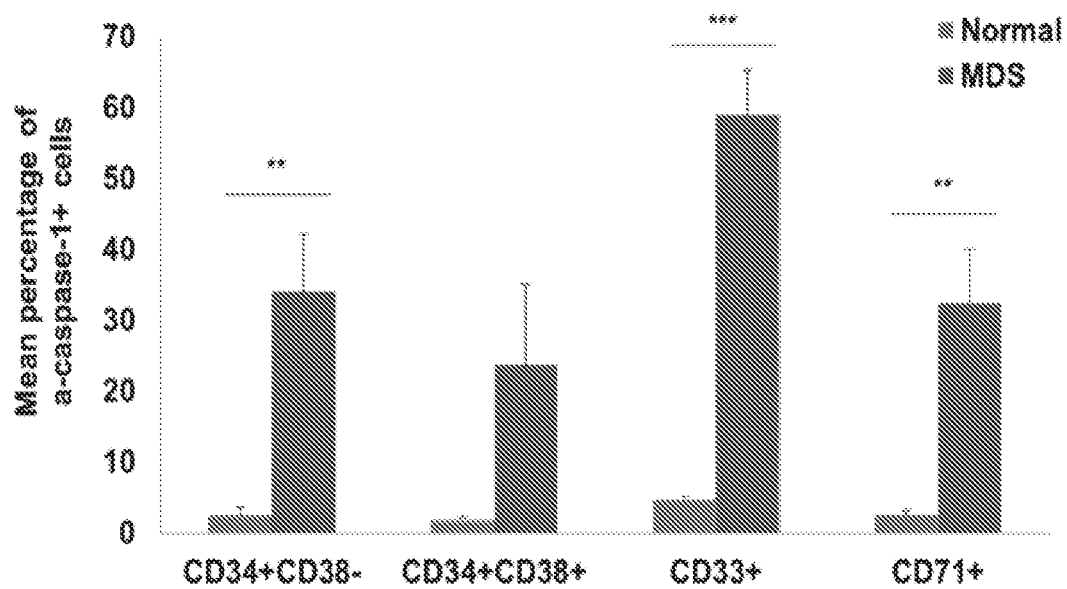
FIG. 97. Mean percentage of total a-caspase-1$^+$ assessed by hematopoietic lineage in lower-risk MDS (n=8) and normal donors (n=5).
Figure 98:
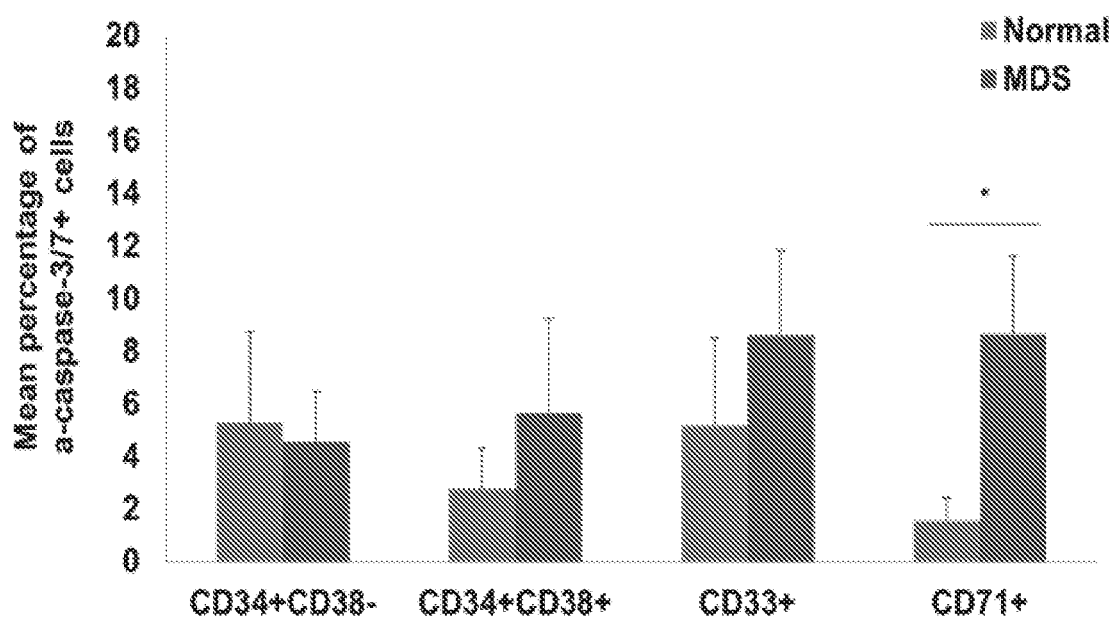
FIG. 98. Mean percentage of a-caspase-3/7$^+$ cells assessed by hematopoietic lineage in lower-risk MDS (n=8) and normal donors (n=5).
Figure 99:
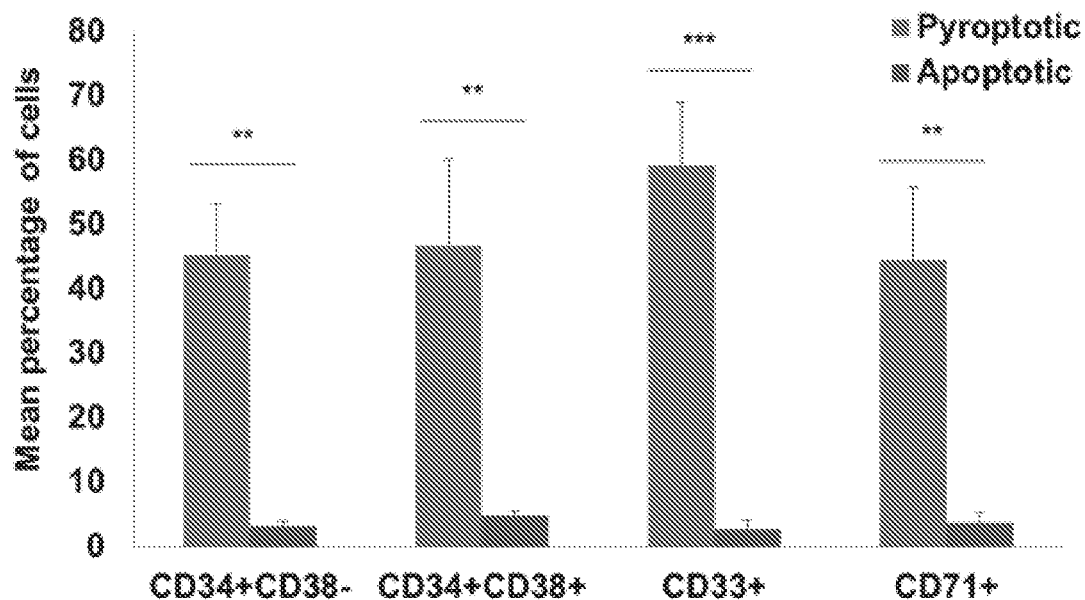
FIG. 99. Comparison of the mean percentage of pyroptotic versus apoptotic cells by hematopoietic lineage in lower-risk MDS specimens (n=8).
Figure 100:
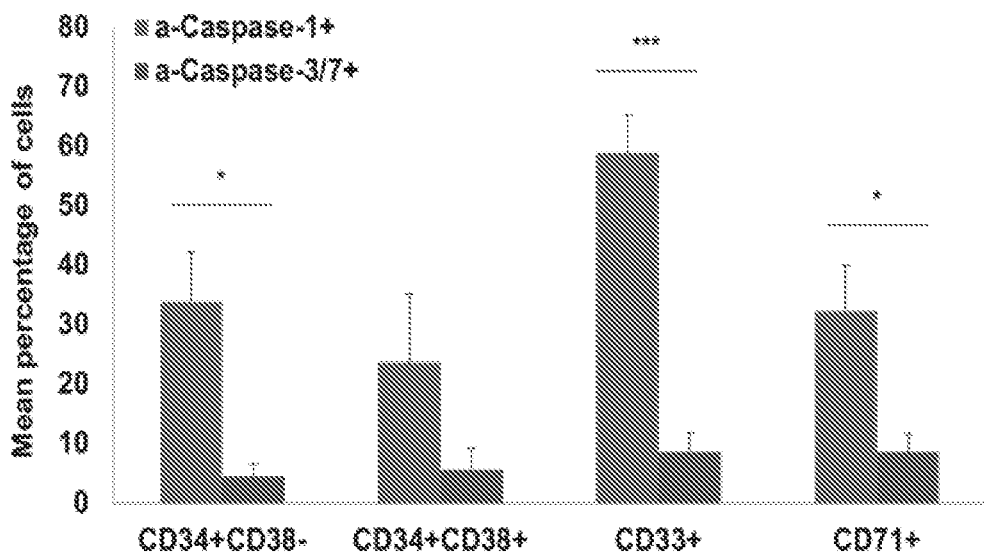
FIG. 100. Comparison of the mean percentage of a-caspase-1$^+$ versus a-caspase-3/7$^+$ cells in the same lower-risk MDS patients (n=8).
Figure 101:
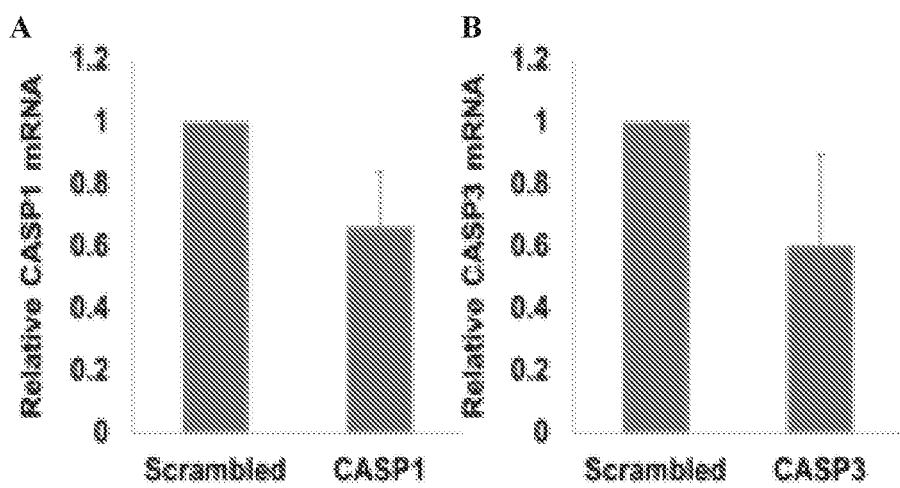
FIG. 101. Relative gene expression of (A) CASP1 and (B) CASP3 assessed by qPCR following shRNA-directed silencing of lower-risk MDS BM-MNC (n=3) by lentivirus infection.
Figure 102:
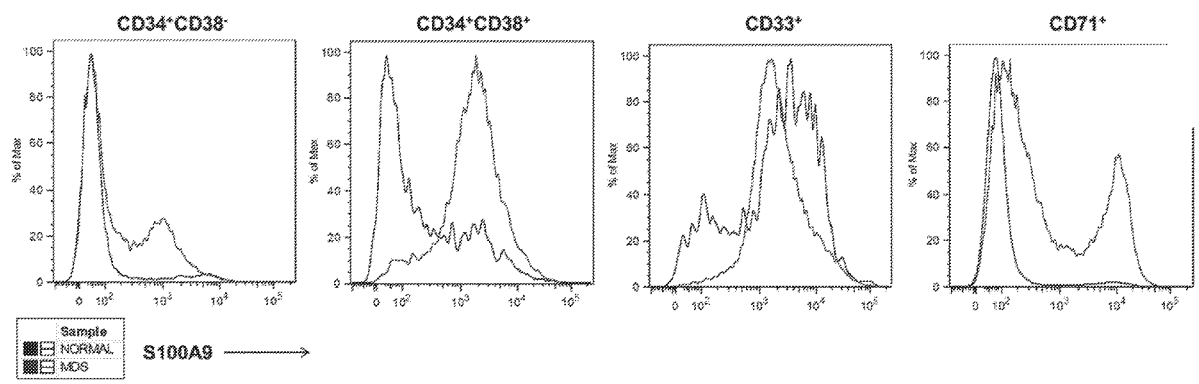
FIG. 102. Representative histograms of intracellular levels of S100A9 by hematopoietic lineage in BM-MNC isolated from MDS patients (n=6) and normal controls (n=5).
Figure 103:
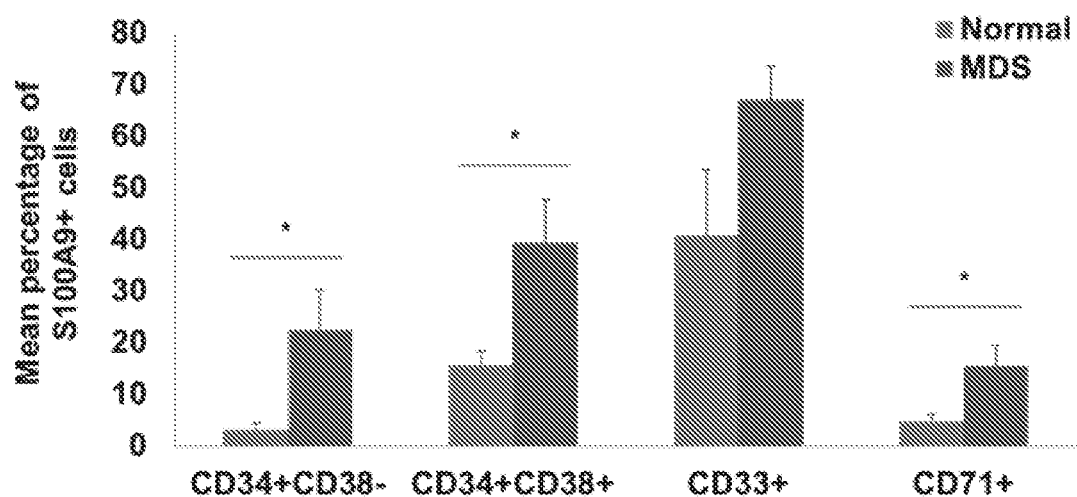
FIG. 103. Mean percentage of S100A9 cells by hematopoietic lineage in MDS patients and normal controls.

Caspase-1 activation by the inflammasome is followed by mitochondrial depolarization and caspase-3 activation as late events in pyroptosis. To specifically assess pyroptosis versus apoptosis in MDS, the percentage of pyroptotic cells, defined as the percentage of a-caspase-$1^+$/a-caspase-$3^+$/annexin-$V^+$ cells, was determined in phenotypically distinct hematopoietic lineages by flow cytometry. Normal (n=5) and lower-risk MDS BM-MNC (n=8) were incubated with autologous BM plasma for 24 hours prior to flow cytometry analysis. MDS HSPC demonstrated markedly increased pyroptosis, where the fraction of pyroptotic cells was increased 4.1-fold in $CD34^+CD38^-$ stem cells (p=0.035), 4.9-fold in progenitor cells ($CD34^+CD38^+$, $p=6.8\times10^{-3}$), 6.6-fold in immature myeloid cells ($CD33^+$, $p=1.5\times10^{-3}$), and 7.3-fold in erythroid cells ($CD71^+$, $p=2.8\times10^{-3}$) compared to normal controls (FIG. 96). Additionally, the percentage of a-caspase-$1^+$ cells was increased 14.2-fold in the stem cell fraction ($p=8.0\times10^{-3}$), 13.2-fold in progenitors, 12.9-fold in immature myeloid cells ($p=1.3\times10^{-4}$), and 13.0-fold in $CD71^+$ erythroid precursors ($p=7.7\times10^{-3}$). A-caspase-1 MFI directly correlated with NLRP3 MFI, inflammasome assembly and the percentage of pyroptotic stem cells. Notably, the latter was directly associated with the percentage of a-caspase-$1^+$ $CD33^+$ myeloid progenitors (FIG. 116). The extent of apoptotic cells (i.e., a-caspase-3/$7^+$/a-caspase-$1^+$/annexin-$V^+$) was also evaluated in lower-risk MDS specimens (n=8). No significant differences in a-caspase-3/$7^+$ cells were detected in any of the four hematopoietic lineages investigated (FIG. 98). Indeed, the pyroptotic cell fraction was 14.4-fold ($p=9.7\times10^{-3}$), 9.7-fold ($p=2.3\times10^{-3}$), 21.9-fold ($p=9.5\times10^{-4}$), and 12.1-fold ($p=1.6\times10^{-3}$) increased in stem cells, progenitor cells, immature myeloid and erythroid cells when compared to the apoptotic cell fraction (FIG. 99). Additionally, the fraction of a-caspase-$1^+$ cells was significantly greater than the corresponding a-caspase-3/$7^+$ cell fraction, confirming that caspase-1 activation (pyroptosis) exceeds caspase-3 activation (apoptosis) in MDS (FIG. 100). Finally, to confirm that caspase-1 is essential for hematopoietic cell death in MDS, shRNA-directed silencing of caspase-1 and caspase-3 was performed by lentivirus transfection of lower-risk BM-MNC (n=3) (FIG. 101). Knockdown of caspase-1 significantly decreased the fraction of pyroptotic cells versus scrambled transfected controls (p=0.038) (FIG. 7A). In contrast, knockdown of caspase-3 had no discernible effect (FIG. 7B), confirming selective caspase-1-dependence.

The DAMP Protein S100A9 is a Primary Initiator of Pyroptosis

Figure 43:
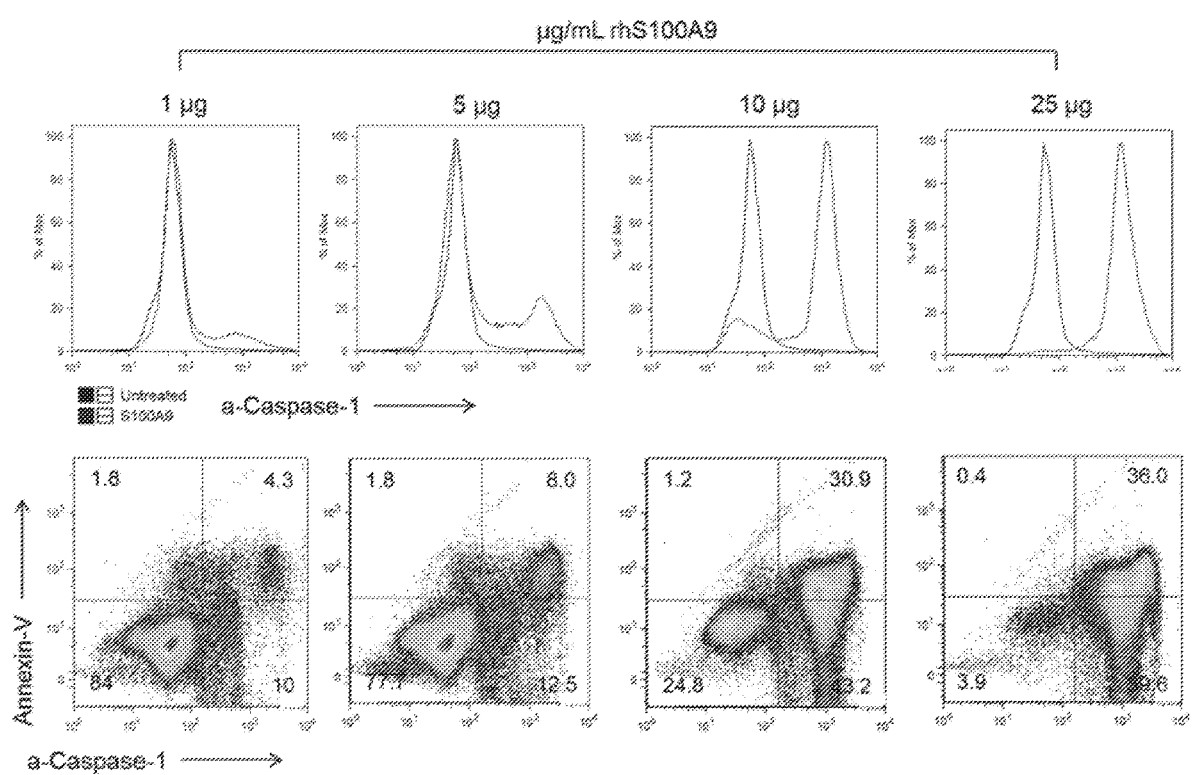
FIGS. 43-47 show that S100A9 provokes pyroptosis and inflammasome activation ex vivo. Error bars: SE, p<0.01 and *p<0.001. Data are representative of three independent experiments.
Figures 44, 45:
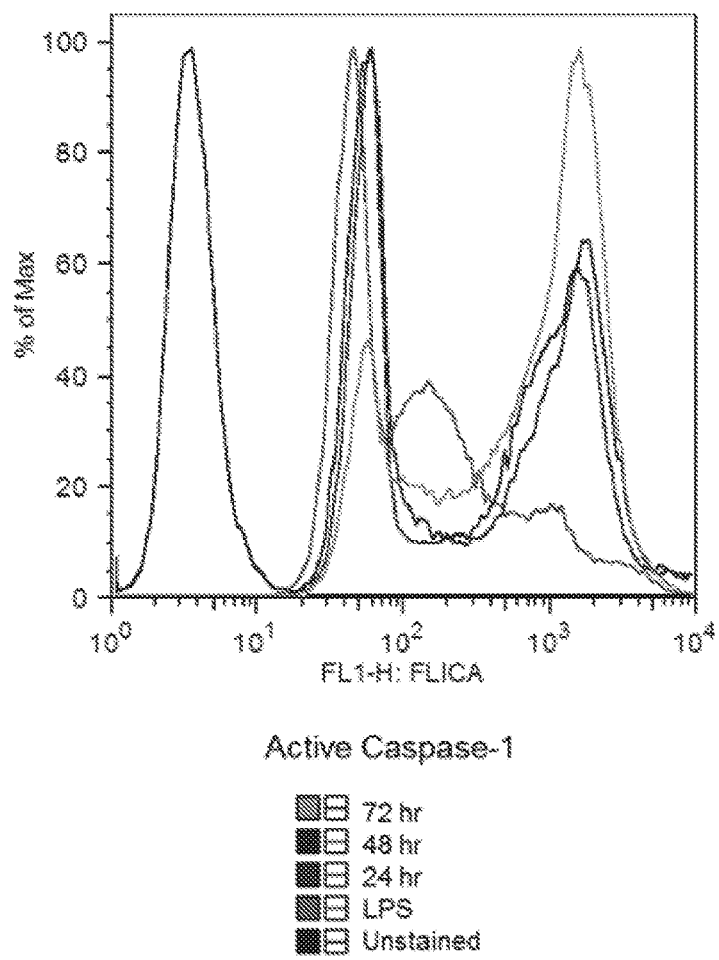
Figure 46:
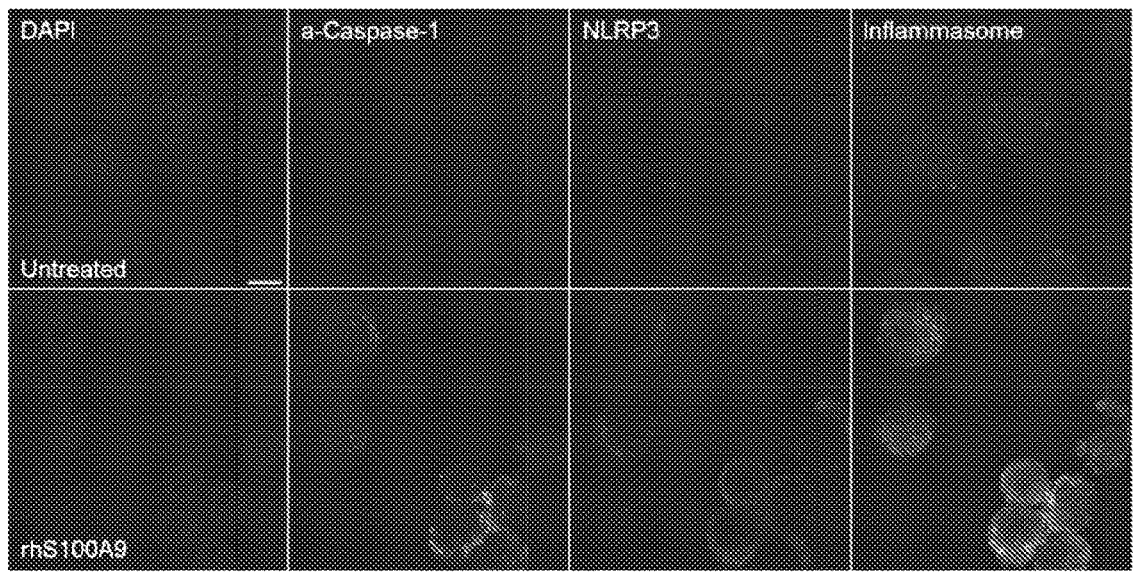
Figure 47:
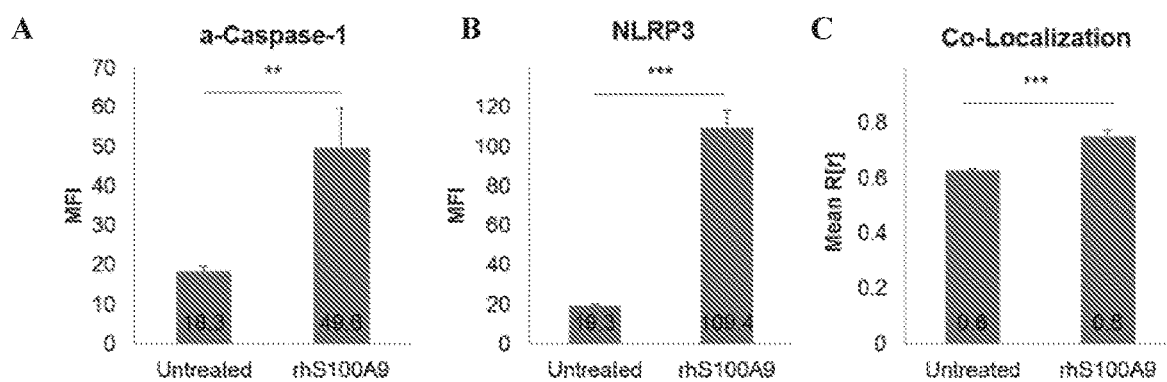

BM plasma concentrations of the alarmin S100A9 are increased in MDS and stimulate the expansion of MDSC through ligation of its cognate receptors, TLR4 and CD33 (Chen X, et al. J Clin Invest. 2013 123(11):4595-611). As NLRPs are sensors of DAMP signals, experiments were conducted to determine if S100A9 triggers pyroptosis in MDS. Indeed, treatment of the monocytic cell line U937 with recombinant human S100A9 (rhS100A9) resulted in a concentration-dependent increase in the fraction of pyroptotic cells (FIG. 43), with a corresponding increase in a-caspase-1 MFI and percentage of a-caspase-$1^+$ cells (FIG. 44A). Likewise, treatment with 5 µg/mL rhS100A9 provoked a time-dependent increase in activation of caspase-1 (FIG. 44B, 45). Furthermore, treatment with rhS100A9 markedly increased levels of NLRP3 inflammasome complexes and this was accompanied by caspase-1 activation (FIG. 46, 47).

Figure 8:
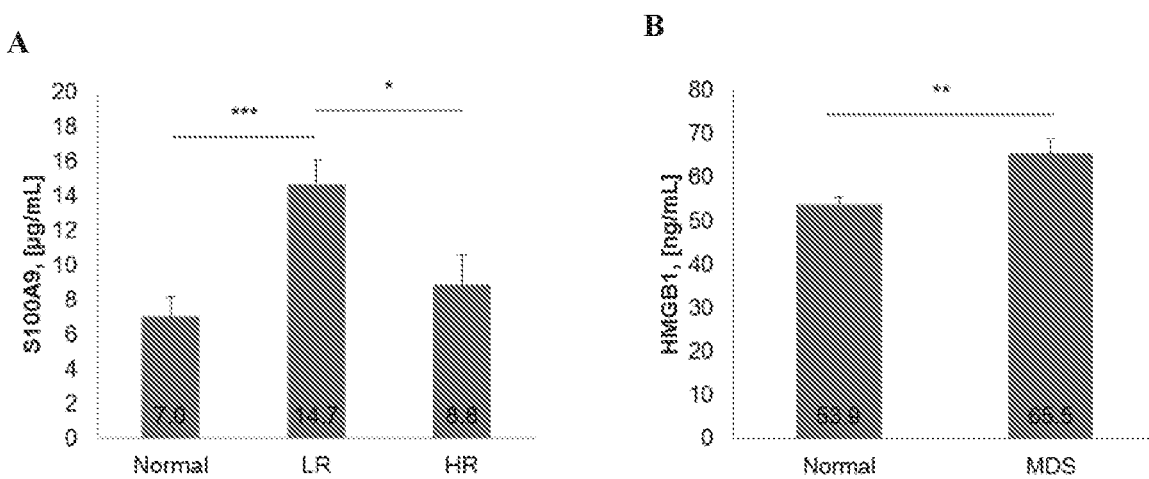
FIGS. 8-12 show S100A9 initiates pyroptosis in MDS. Error bars: SE, *$p<0.05$, $p<0.01$, and *$p<0.001$.
Figure 9:
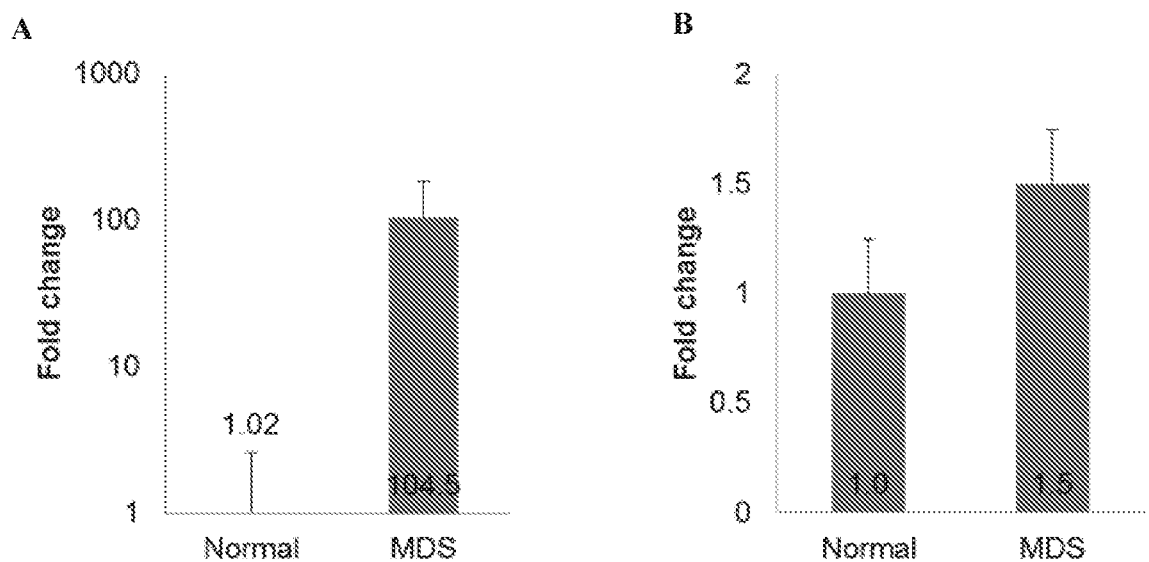
Figure 48:
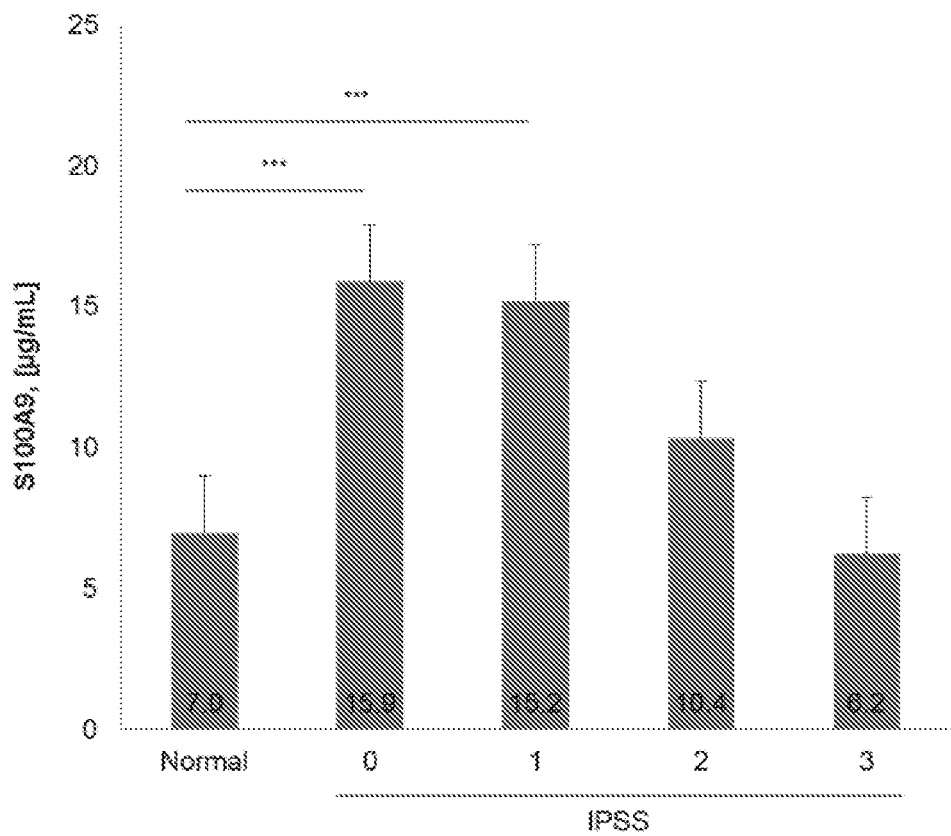
FIG. 48 shows that plasma levels of S100A9 are elevated in MDS. BM plasma concentration of S100A9 was assessed by ELISA and analyzed according to IPSS risk score. Only MDS patients with lower-risk disease (IPSS=0, IPSS=1) demonstrate a statistically significant increase in BM plasma S100A9 concentration ($p=2.3 \times 10^{-5}$ and $1.0 \times 10^{-3}$, respectively). Error bars: SE, ***p<0.001.
Figure 49:
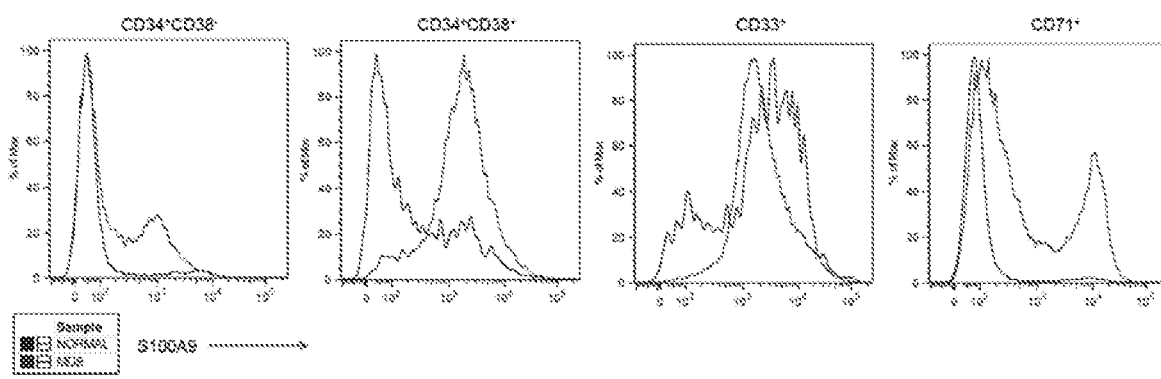
FIGS. 49-51 show that intracellular levels of the alarmin S100A9 are increased across myeloid lineages.
Figure 50:
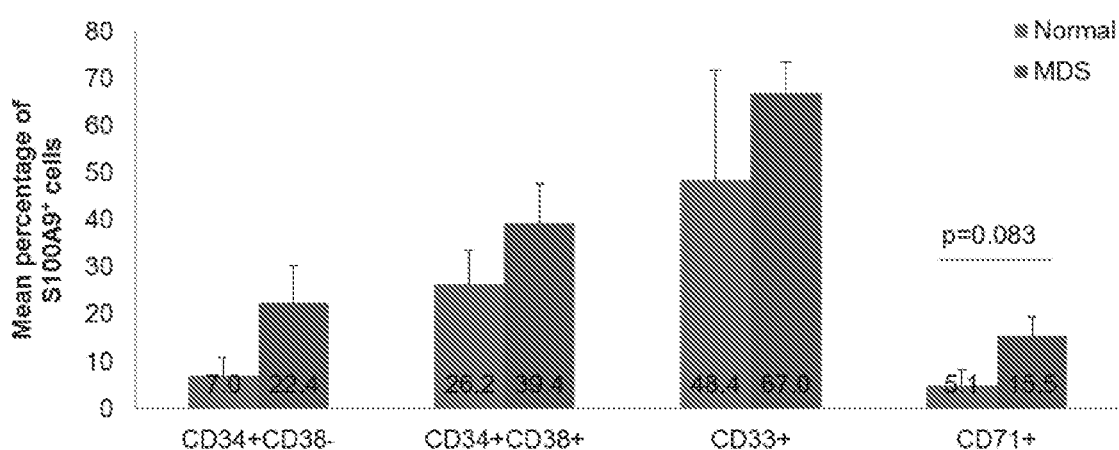
Figure 51:
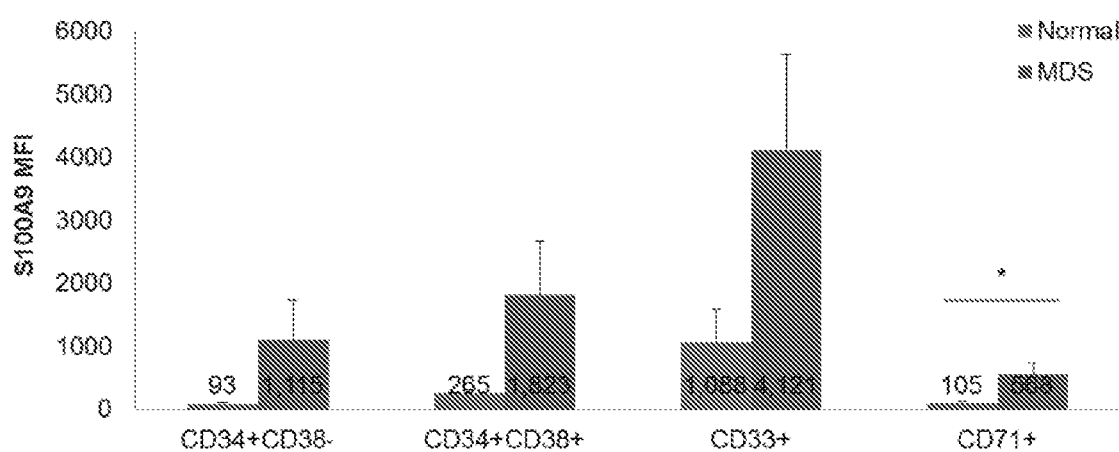
Figure 52:
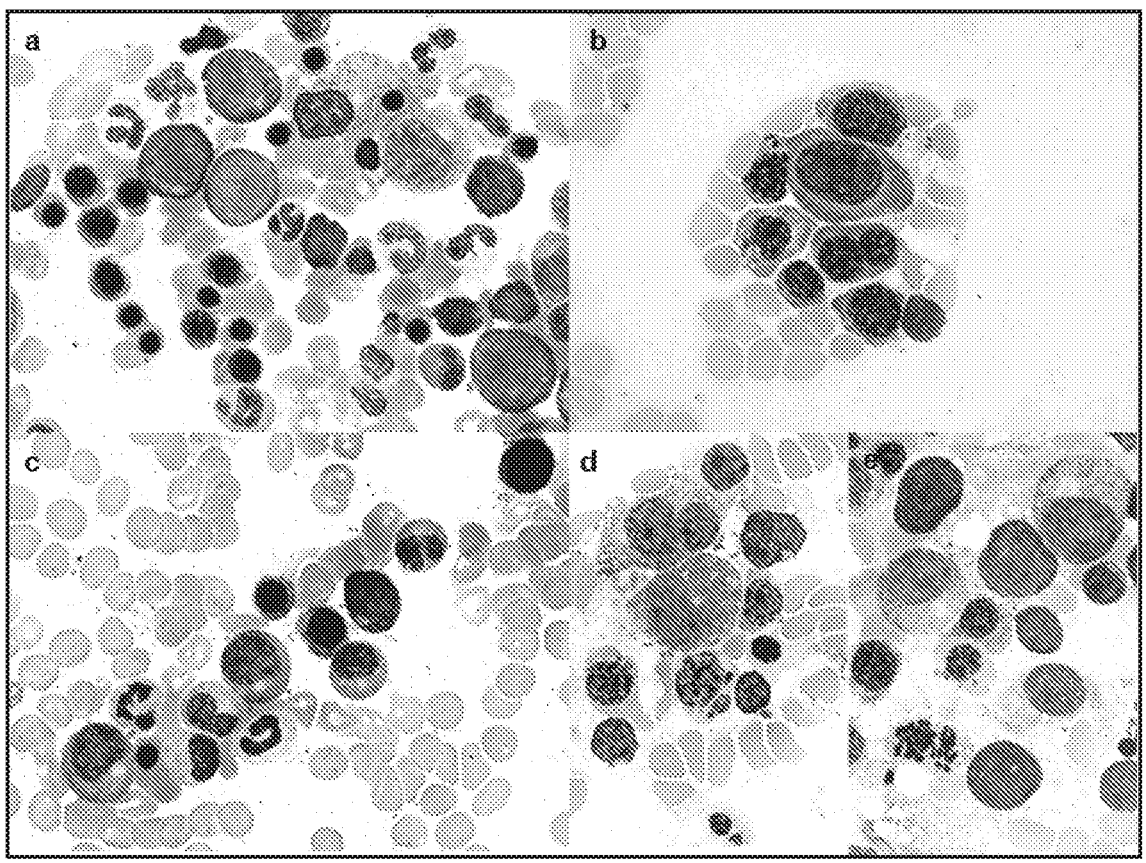
FIG. 52 shows increased size of MDS hematopoietic lineage cells. Images depict Wright-Giemsa staining (1000× magnification). (a) Normal BM with mild erythroid hyperplasia. The erythroid precursors show a full spectrum of maturation with mean cellular diameter recorded at different maturation stages [orthrochromic normoblast, 7.5 μm (normal reference: 6-12 μm); early to late polychromic normoblasts, 8.5 μm (normal reference: 8-14 μm); early and late basophilic normoblasts, 12.4 μm (normal reference: 12-17 μm and 10-15 μm, respectively); and promonoblasts, 15.8 μm (normal reference: 14-24 μm)]. (b) Dysplastic erythroid precursors in the BM from an MDS patient. The erythroid precursors show obscured stage specific maturation or maturation asynchrony. Hematopoietic precursors are enlarged in size compared to the corresponding stage of maturation in normal donors [dysplastic/megaloblastoid orthrochromic normoblasts (15.8 μm), dysplastic early to late polychromic binucleated normoblast (18.2 μm), dysplastic late basophilic normoblasts (17.6 μm), and dysplastic promonoblasts (25.5 μm)]. (c) Normal BM with complete spectrum of myeloid maturation. The myeloid progenitors represent different stages of maturation with appropriate size [segmented neutrophil (10-18 μm), band form (10-20 μm), metamyelocyte (10-18 μm), myelocyte (10-20 μm), promyelocyte (12-24 μm), and myeloblasts (9-20 μm)]. (d) Enlarged eosinophilic myelocytes measuring 23.1 μm at the maximal dimension in a background of marked dyserythropoiesis. (e) Enlarged myelocyte with overt maturation asynchrony in a background of dyserythropoiesis in an MDS BM. The myelocyte measures 23.6 µm, which is larger than a normal myelocyte.

The BM plasma concentration of S100A9 was significantly higher in lower-risk patient specimens (n=33) compared to normal controls (n=12; $p=1.5\times10^{-4}$), with no difference in higher-risk patient specimens (n=27, FIG. 8A). Analysis of S100A9 BM plasma concentration by International Prognostic Scoring System (IPSS) risk category showed a 2.3- and 2.2-fold increase in low risk (n=10, $p=2.3\times10^{-5}$) and intermediate-I (n=23, $p=1.0\times10^{-3}$), compared to normal controls (n=12), with no significant differences among controls and intermediate-II (n=17) or high risk (n=10) disease (FIG. 48). Notably, BM S100A9 concentrations were significantly higher in lower-risk versus higher-risk MDS (p=0.013) (FIG. 8A). In addition, the BM plasma concentration of HMGB1, a nuclear DAMP and TLR4 ligand, was significantly increased in MDS (n=55) versus normal controls (n=11) ($p=2.6\times10^{-3}$) (FIG. 8B) (Velegraki M, et al. Haematologica. 2013 98(8):1206-15; Chirico V, et al. Eur J Pediatr. 2014 173(9):1123-36). Moreover, S100A9 and HAMGB1 gene expression were up-regulated 104.5-fold and 1.5-fold in MDS, respectively, compared to normal controls (FIG. 9A, 9B), and flow cytometric analysis confirmed a corresponding increase in cellular expression of the S100A9 alarmin in MDS stem cells and progeny (FIG. 49-51).

Figure 10:
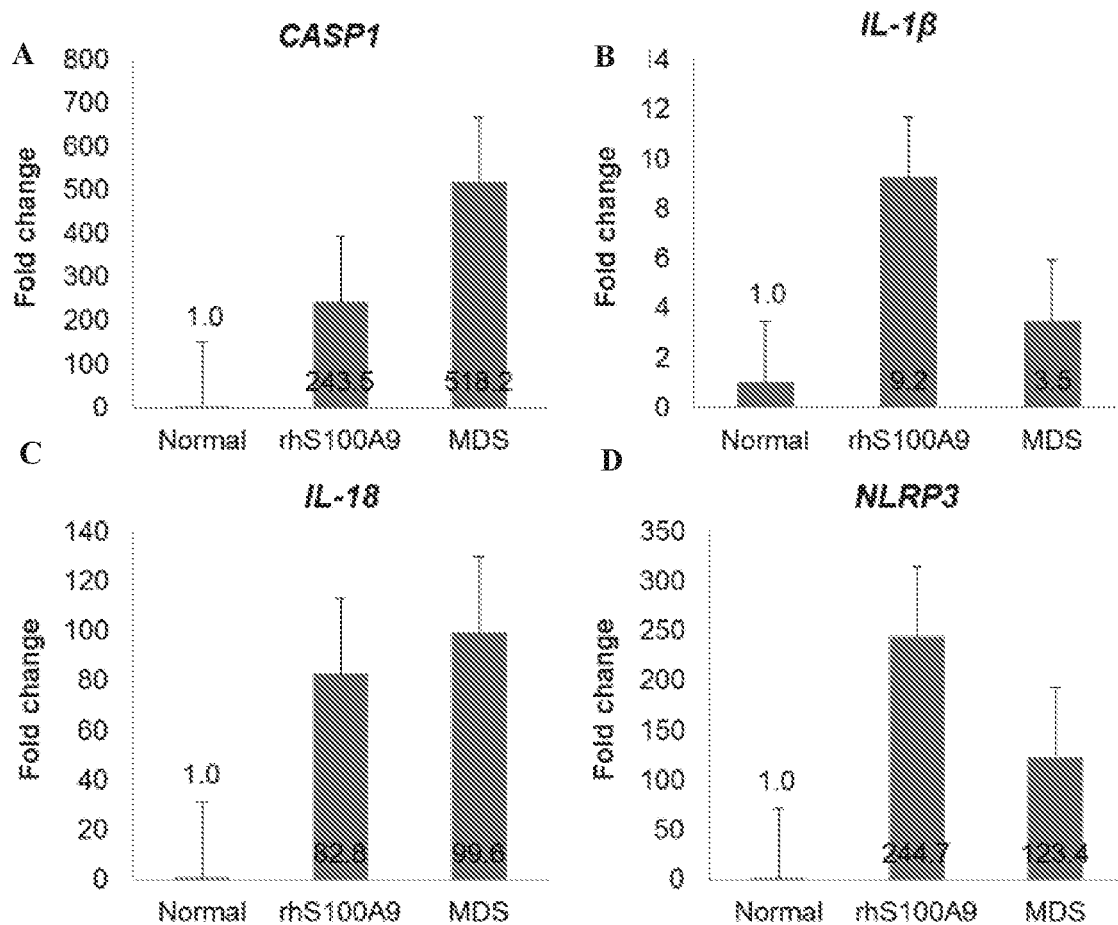
Figure 11:
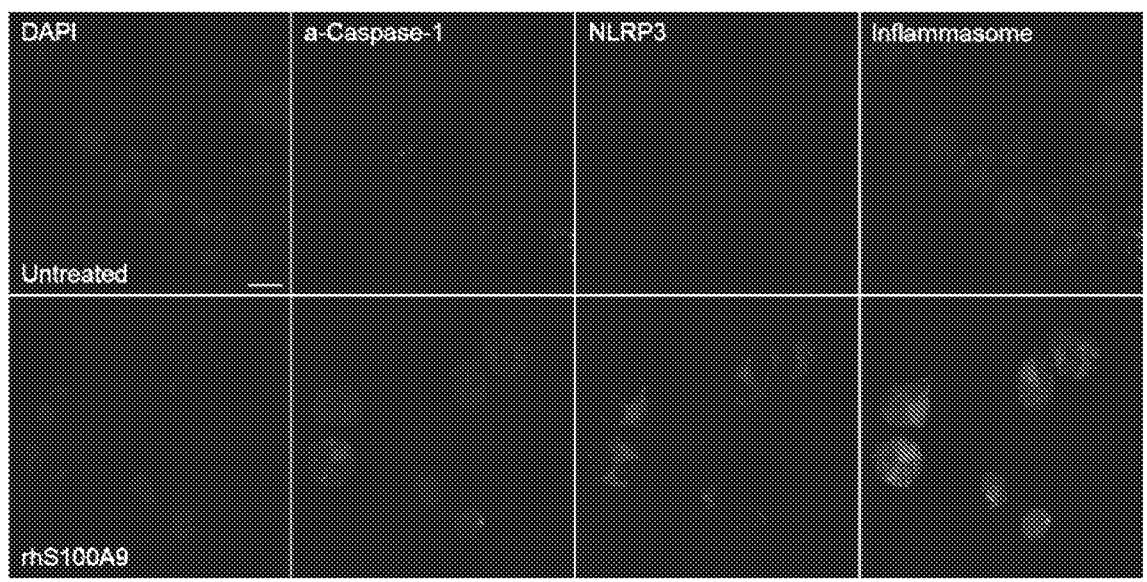
Figure 12:
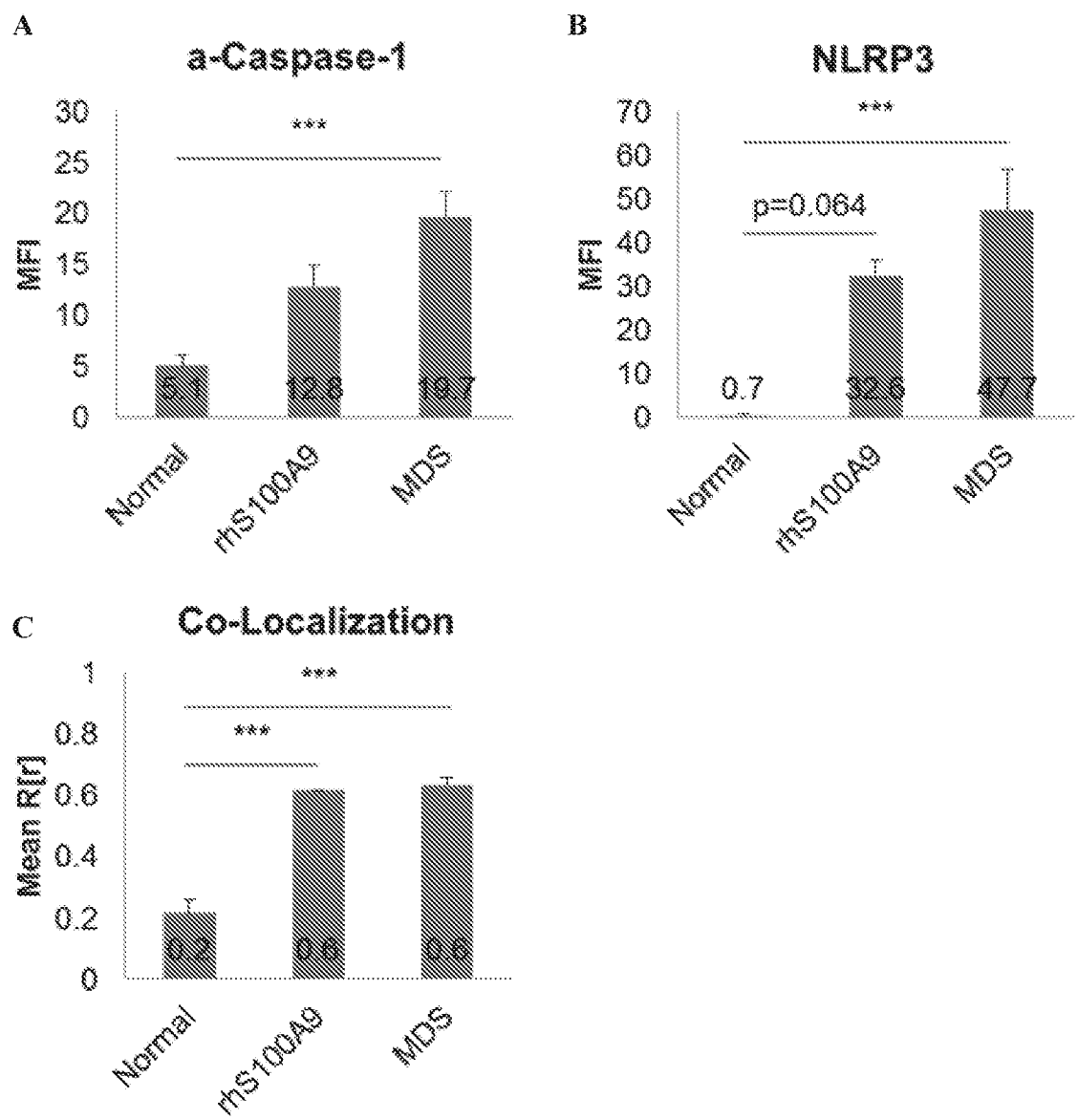

To determine if S100A9 directly triggers pyroptosis in HSPC, normal BM-MNC (n=2) were treated with 1 µg/mL rhS100A9 and changes in gene expression was assessed by qPCR. The expression of pyroptosis-associated genes was significantly up-regulated following addition of rhS100A9, for some to levels that surpass those detected in MDS (n=5) (FIG. 10). Accordingly, a-caspase-1 and NLRP3 levels were induced following treatment of normal BM-MNC with 5 pig/mL rhS100A9 (FIG. 11), by 2.5-fold and 47.1-fold (p=0.064), respectively, as were formation of NLRP3 inflammasomes, by 2.9-fold ($p=3\times10^{-4}$) (FIG. 12). Finally, although rhS100A9 treatment induced inflammasome assembly and caspase-1 activation in normal controls, MDS patient specimens (n=10) displayed greater activation and co-localization of these effectors. Notably, treatment of normal BM-MNC (n=3) with MDS-derived bone marrow plasma demonstrated no significant induction of pyroptosis, as measured by mean percentage of pyroptotic cells, a-caspase-11 cells or a-caspase-1 MFI, indicating that MDS HSPCs are selectively primed for the pyroptotic response.

Inflammasome-Initiated Pore Formation Increases Size of MDS Precursors

Figure 13:
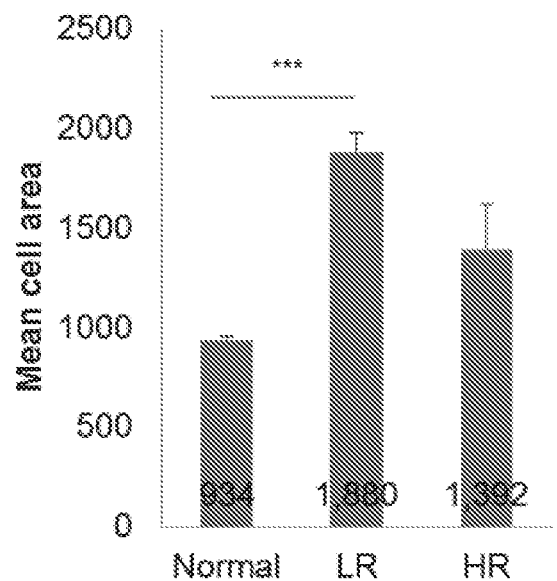
FIGS. 13-19 show that inflammasome-initiated pore formation increases size of MDS precursors.
Figure 14:
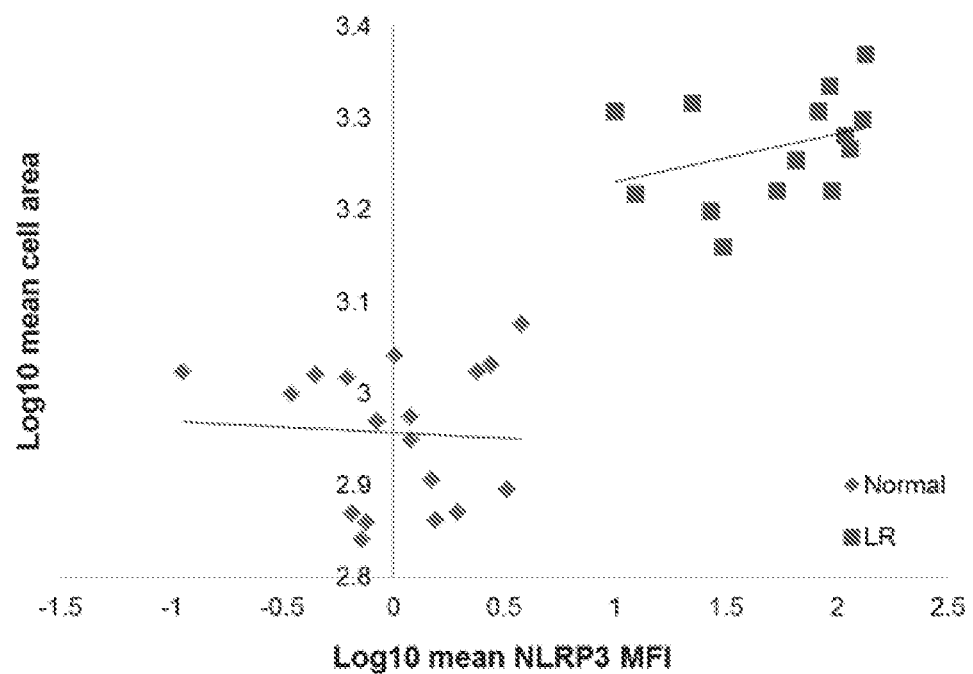
Figure 15:
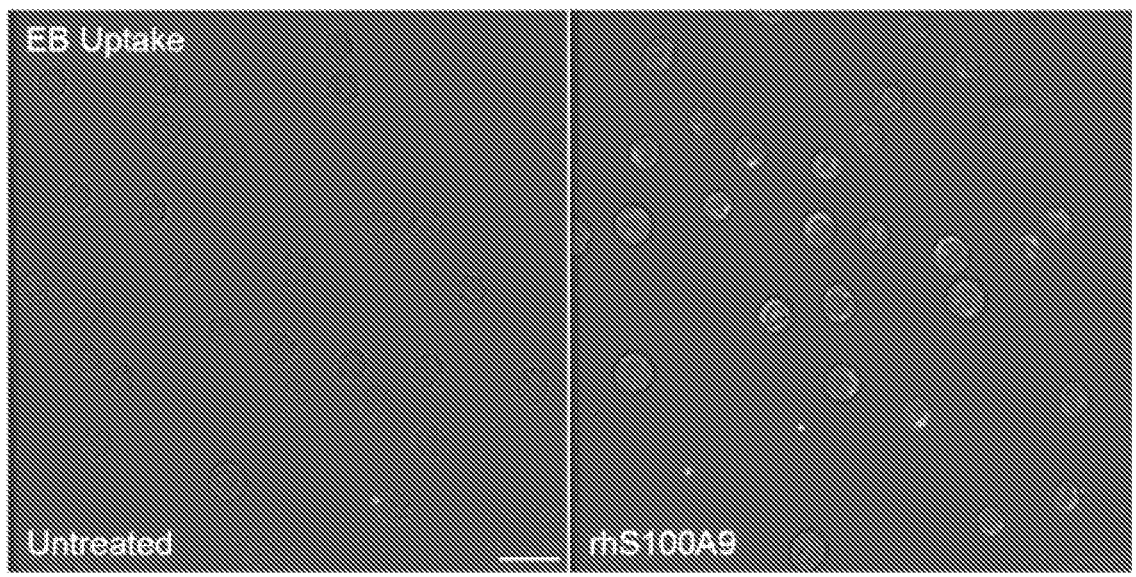
Figure 16:
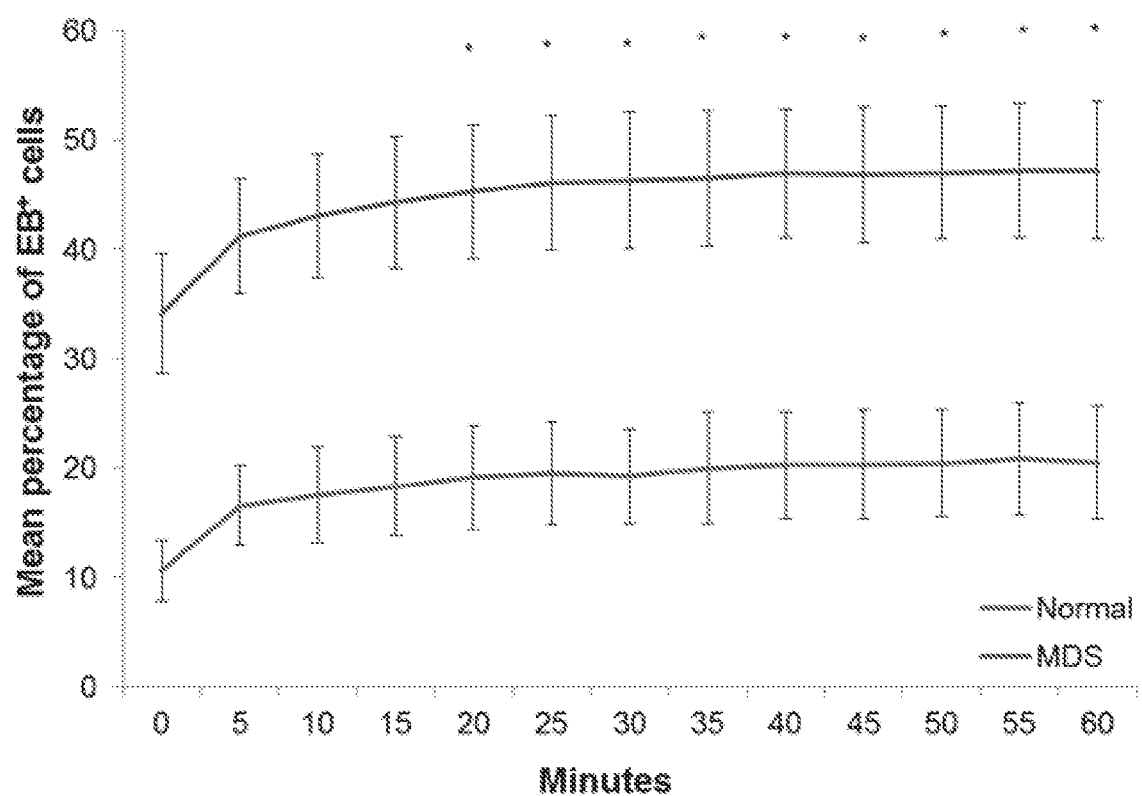
Figure 17:
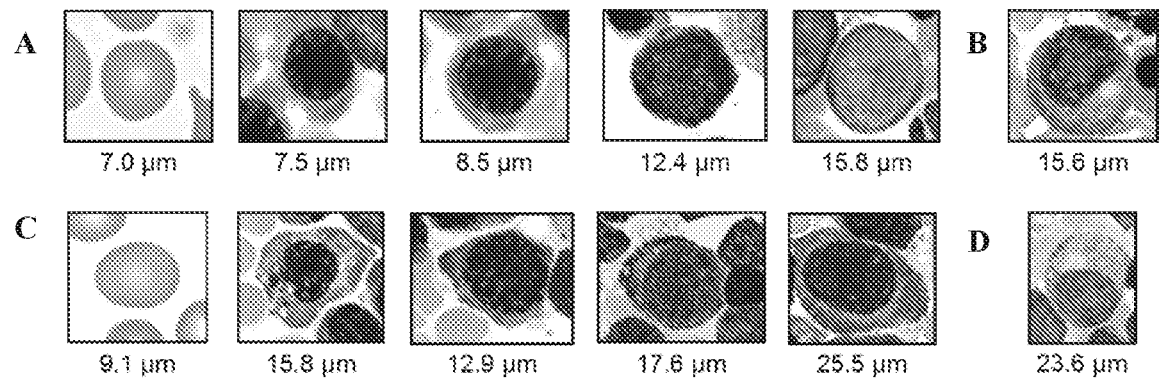
Figure 18:
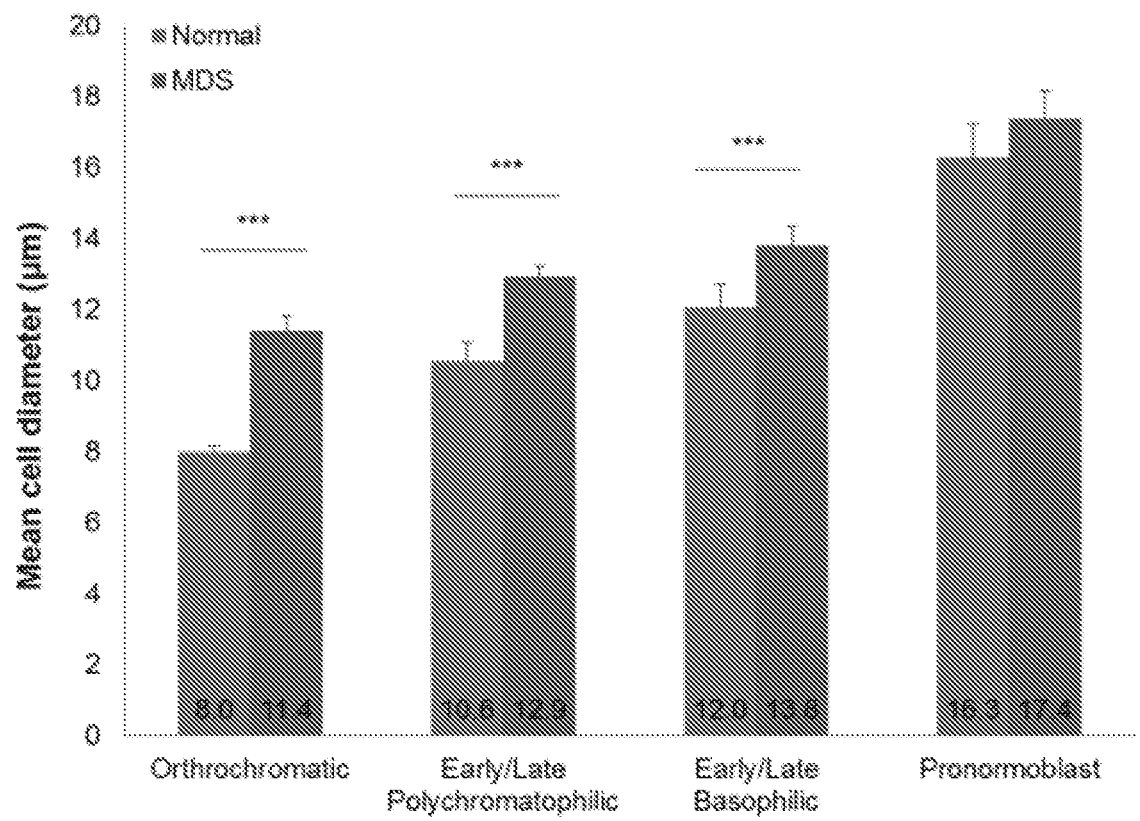
Figure 19:
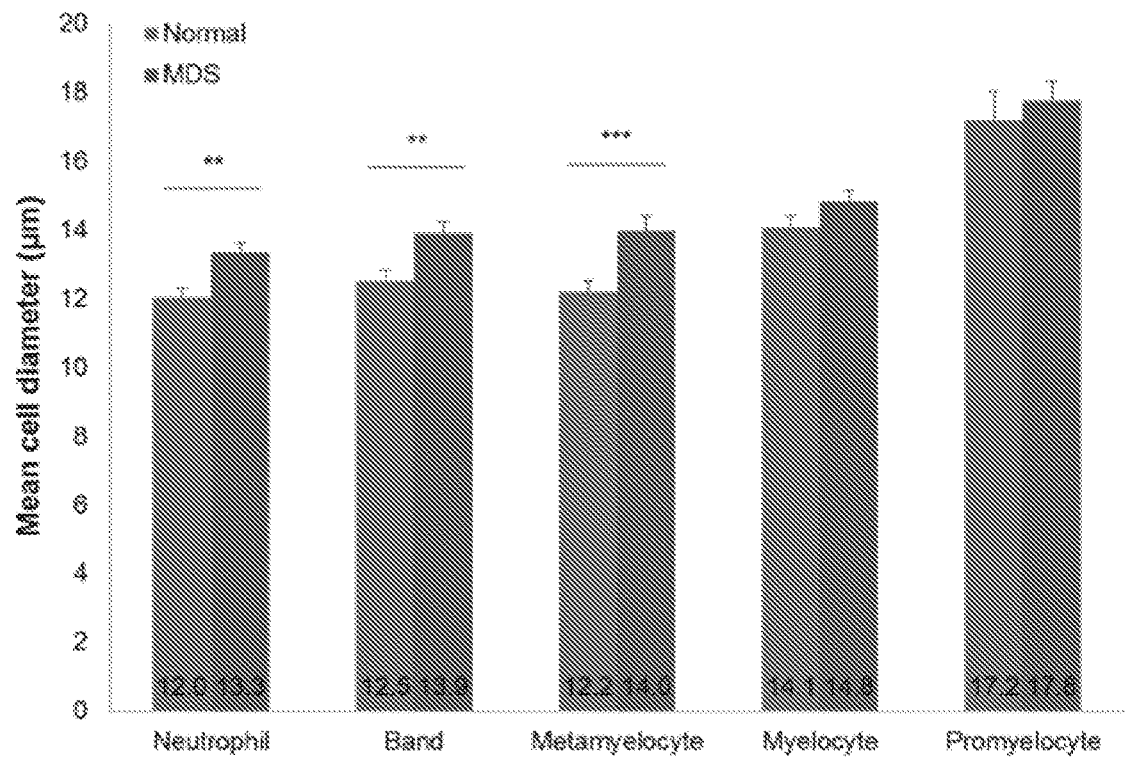
Figure 104:
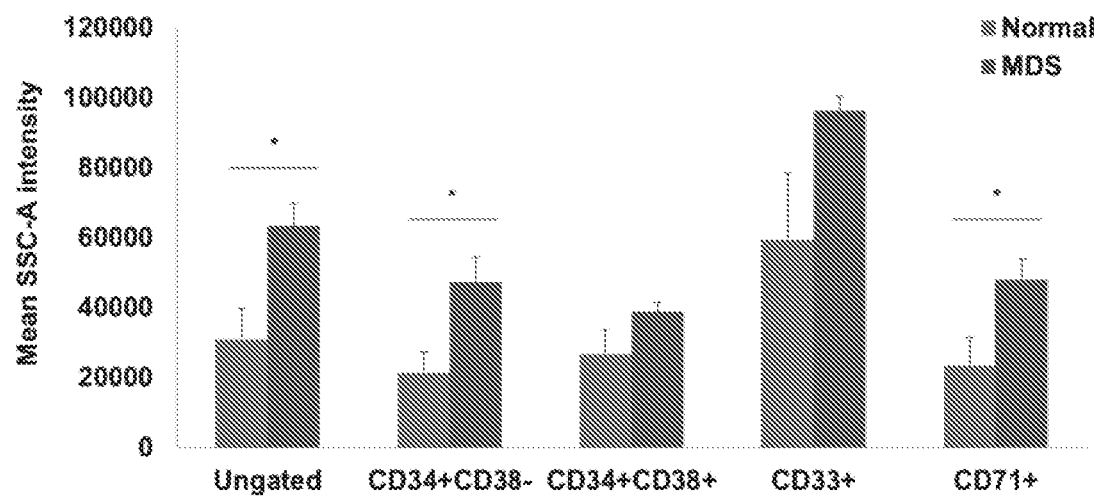
FIG. 104. Flow cytometric analysis of mean SSC-A intensity of BM-MNC isolated from normal donors (n=6) or lower-risk MDS patients (n=7). MDS BM-MNC have 2.0-fold greater mean cell area of live, ungated BM-MNC (p=0.017), 2.2-fold of stem cells (CD34$^+$CD38$^-$, p=0.019), 1.5-fold of progenitor cells (CD34$^+$CD38$^+$), 1.6-fold of immature myeloids (CD33$^+$) and 2.0-fold of erythroids (CD71$^+$, p=0.038).
Figure 105:
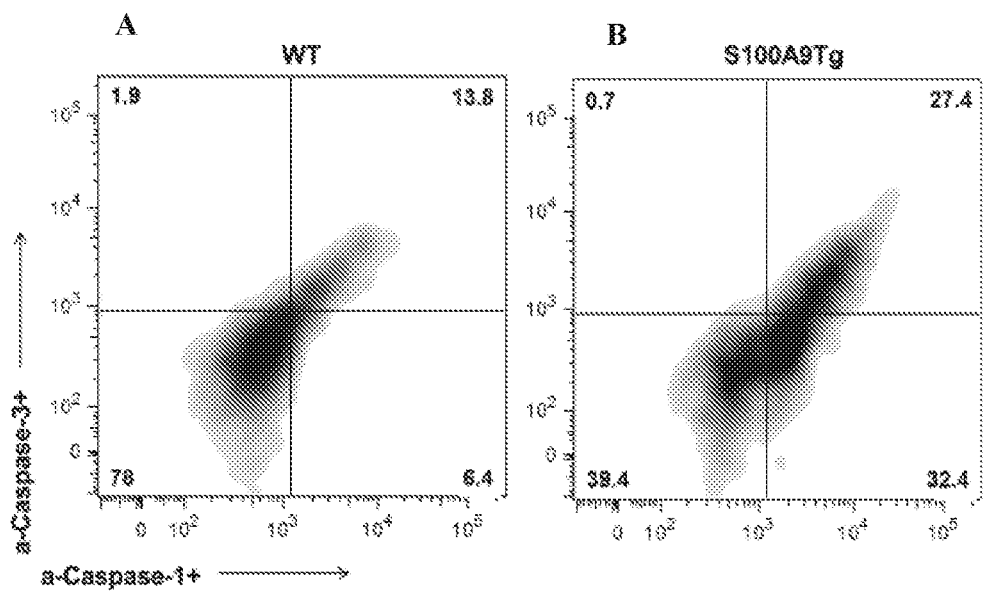
FIG. 105. Representative scatter plots of apoptotic KLS (c-Kit$^+$Lin$^-$Sca-1$^+$) cells isolated from (A) WT and (B) transgenic mice.

Cell swelling is a hallmark of pyroptosis. This occurs following caspase-1-mediated activation of plasma membrane cation channels, which compromises membrane integrity and disrupts osmolality (Fink S. L. & Cookson B. T. Cell Microbiol. 2006 8(11):1812-25). Confocal image analyses of MDS BM-MNC cells demonstrated significantly larger mean cell area compared to normal controls (FIG. 13). This phenotype was accentuated in lower-risk MDS patients compared to normal controls ($p=6.0\times10^{-5}$), with no significant difference detected in higher-risk patients. These findings were corroborated using SSC-A flow cytometric measurements, a validated reference for cell size, in ungated BM-MNC derived from lower-risk MDS patients (n=7) and normal donors (n=6), as well as in antigenically distinct hematopoietic lineages (FIG. 104). Further, there was a positive correlation between mean NLRP3 MFI and mean cell area in lower-risk (but not higher-risk) MDS patients (r=0.49) (p=7.8×10$^{-3}$) (FIG. 14). To assess pore formation, influx of the membrane-impermeable, cationic dye ethidium bromide was assessed by immunofluorescence. As predicted, monocytic U937 cells treated with rhS100A9 demonstrated rapid and substantial uptake of ethidium bromide (FIG. 15). Further, flow cytometric analyses of ethidium bromide uptake demonstrated that MDS specimens incubated with autologous bone marrow plasma had rapid and sustained elevated dye influx versus that of BM-MNC from normal donors, which was demonstrable as early as 20 minutes (p=0.041), and remained significant through 1 hour of dye exposure (p=0.014) (FIG. 16). Finally, analysis of normal and MDS bone marrow aspirate morphology confirmed the larger cell size by maturation stage and lineage in MDS (FIG. 17-19, 52).

Inhibition of Pyroptosis Improves Hematopoiesis in MDS

Figure 20:
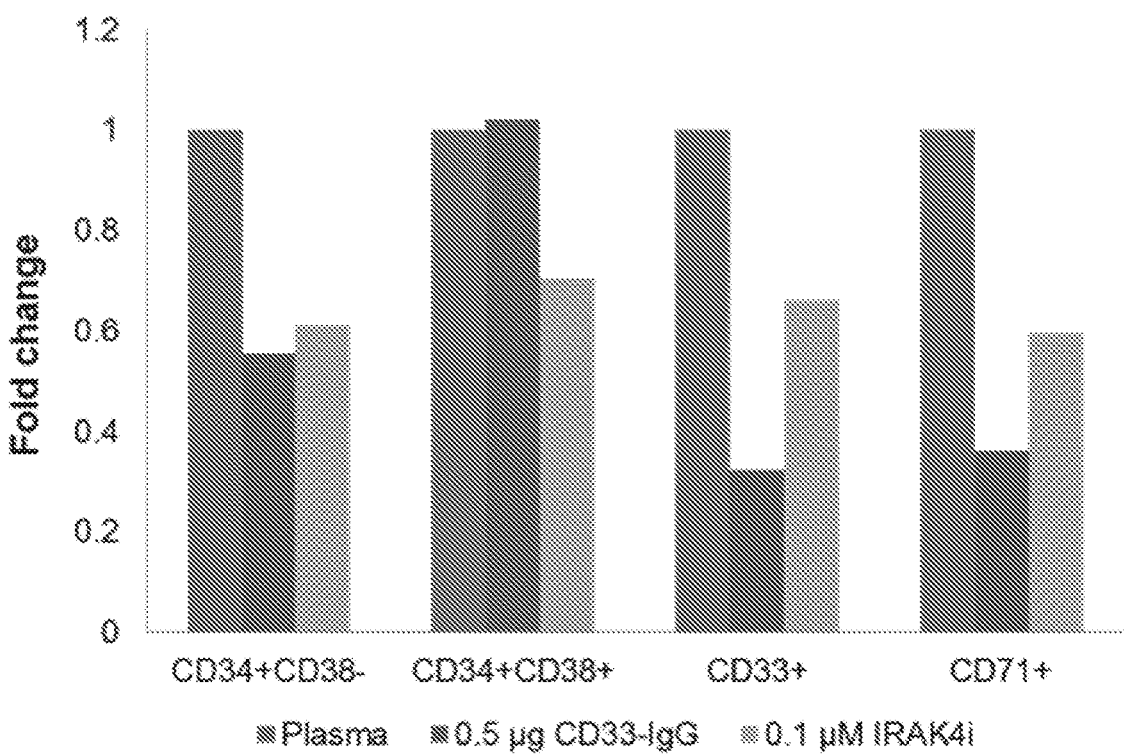
FIGS. 20-24 show that inhibition of pyroptosis abrogates MDS HSPC cell death and augments colony forming capacity.
Figure 21:
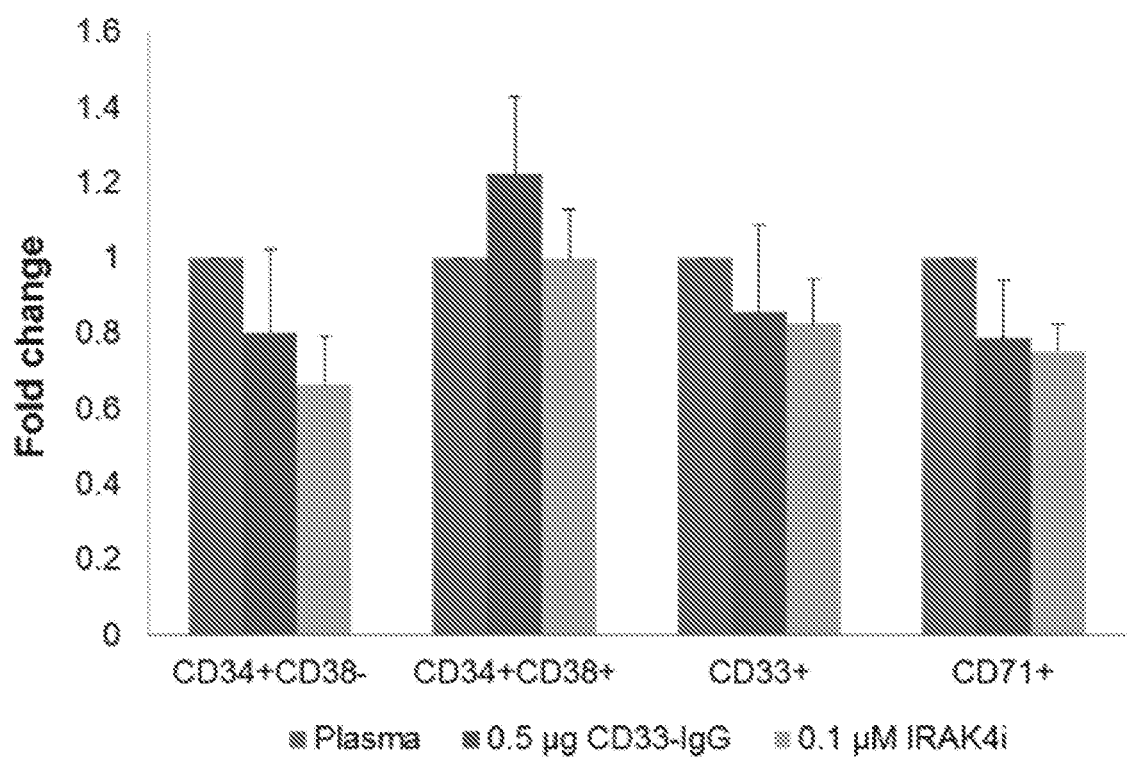
Figure 22:
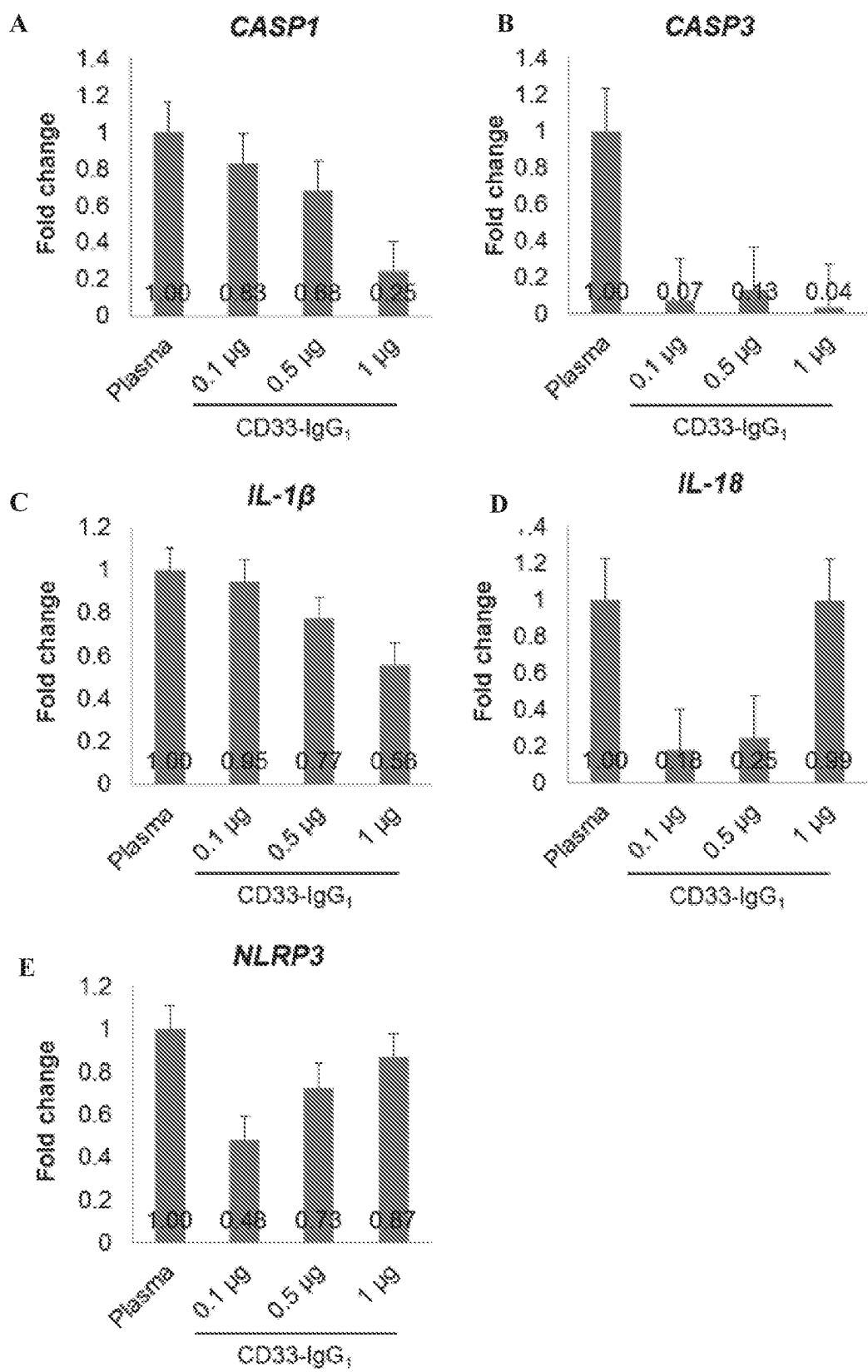

To assess the role of S100A9 in the pyroptosis phenotype evidenced in MDS, experiments were conducted to assess the effects of a S100A9 high-affinity chimeric (CD33-IgG$_1$) decoy receptor or of an IRAK4 inhibitor on phenotypes manifest in BM-MNC (n=4) from MDS patients treated with autologous BM plasma. Notably, treatment with CD33-IgG$_1$ or the IRAK4 inhibitor led to marked reduction in the fraction of pyroptotic cells across all lineages studied (FIG. 20). Overall, short-term incubation with the chimera or the IRAK4 inhibitor reduced the fraction of pyroptotic cells, with corresponding maximum lineage-specific changes in stem cells (44% vs. 75%, respectively), progenitor cells (23% vs. 36%, respectively), CD33+(68% vs. 55%, respectively) and CD71$^+$ cells (64% vs. 55%, respectively) (FIG. 21). Short-term treatment with the chimeric receptor also significantly reduced the MDSC fraction, suggesting that S100A9 neutralization impairs the survival of MDSC. Consistent with this, the CD33 chimera reduced expression of CASP1, IL-1β, IL-18, and NLRP3 versus autologous BM plasma alone (n=5) (FIG. 22). CASP3 expression was also markedly reduced, which is consistent with caspase-3 being activated downstream of caspase-1 after late mitochondrial depolarization (Ali A, et al. J Hematother Stem Cell Res. 1999 8(4):343-56). High concentrations of the chimera led to cross-linking of the IgG$_1$-Fc domains and aggregation that masked dose-dependent effects of S100A9 neutralization.

Figure 23:
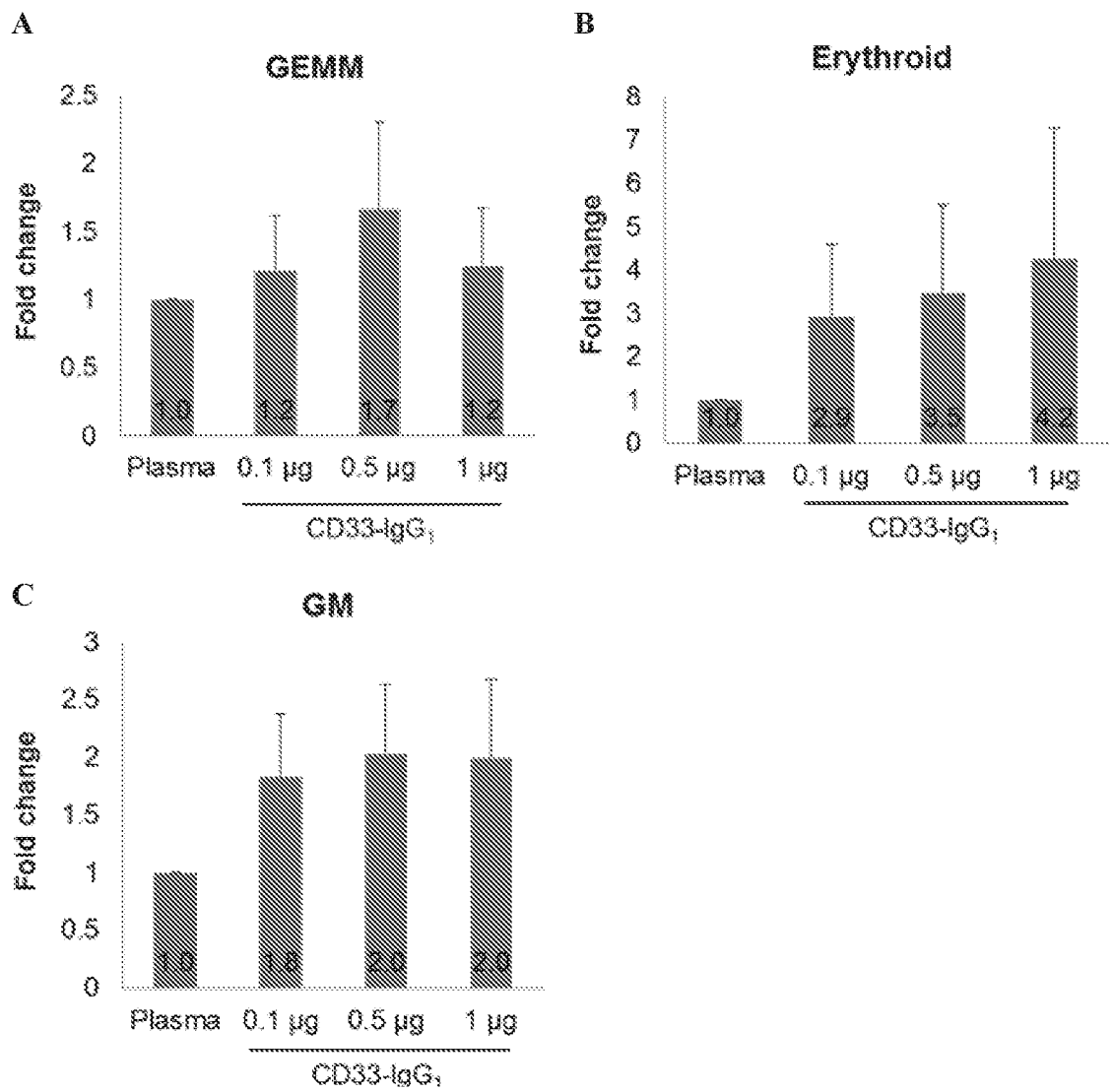
Figure 24:
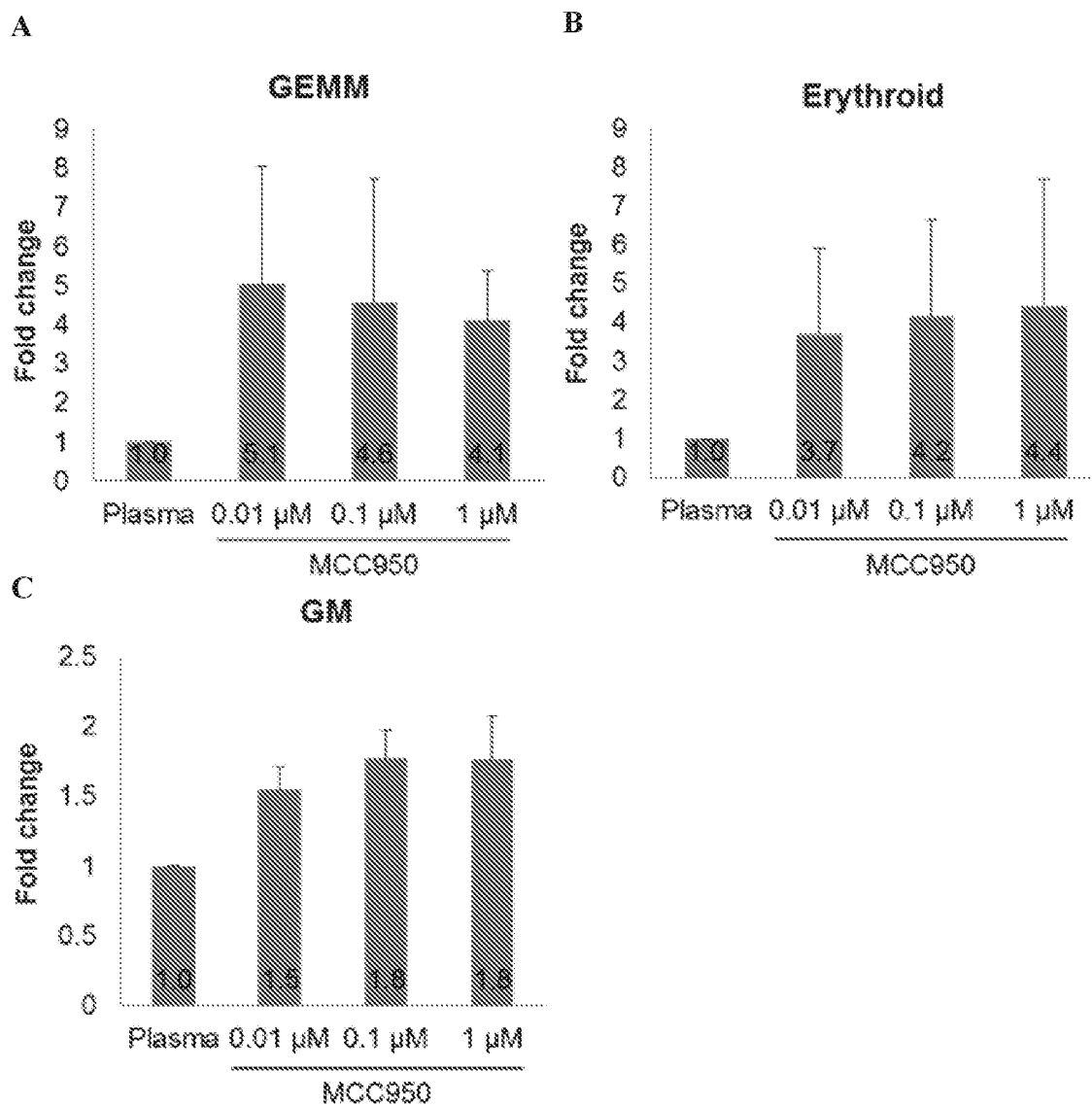

To test if S100A9 neutralization could improve hematopoiesis in MDS, colony forming capacity was assessed after plating of MDS BM-MNC in autologous BM plasma and increasing concentrations of CD33-IgG$_1$ (FIG. 23) or of MCC950 (FIG. 24), a small molecule inhibitor of NLRP3 (Coll R. C, et al. Nat Med. 2015 21(3):248-55). Neutralization of S100A9 or inhibition of the NLRP3 inflammasome markedly improved colony-forming capacity (up to 6.6-fold greater than controls). Thus, pyroptotic pathway inhibition abrogates MDS hematopoietic cell death and promotes effective hematopoiesis.

S100A9 is Sufficient to Provoke HSPC Pyroptosis In Vivo

Figure 25:
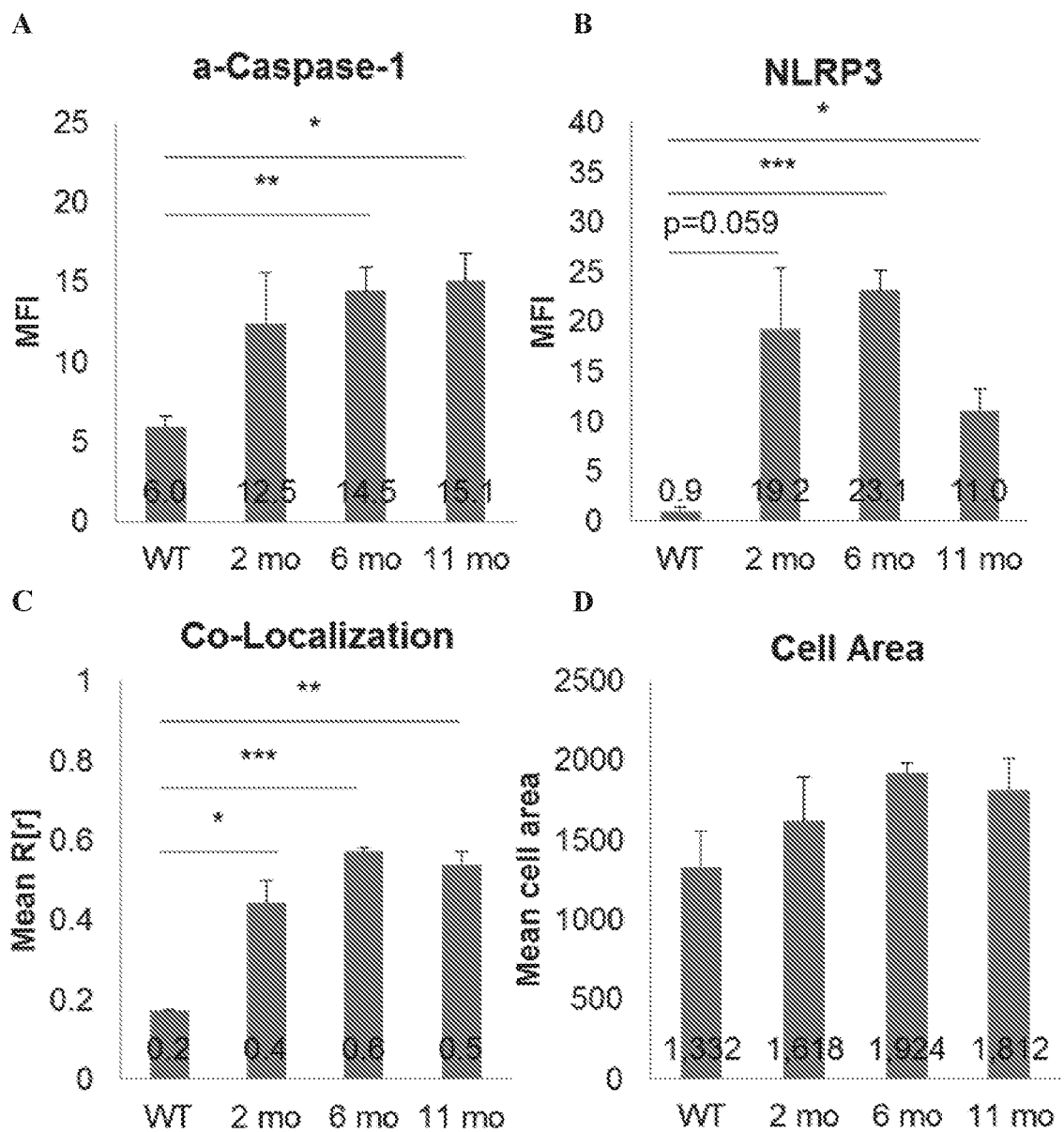
FIGS. 25-32 show that pyroptosis is the principal mechanism of HSPC death in S100A9 transgenic mice. Error bars: SE, *$p<0.05$, $p<0.01$, and *$p<0.001$.

To assess whether forced expression of S100A9 was sufficient to induce pyroptosis in vivo, an S100A9 transgenic (S100A9Tg) mouse model that phenocopies human MDS was analyzed (Chen X, et al. J Clin Invest. 2013 123(11): 4595-611). Confocal fluorescence microscopy analyses of BM cells from the tibia and femurs of S100A9Tg versus wild type (WT) mice at 2 (n=4), 6 (n=4), and 11 (n=5) months of age established that a-caspase-1 levels selectively increased in an age-dependent manner in the BM of S100A9 transgenics, with a 2.1-fold up-regulation at 2 months, 2.4-fold at 6 months (p=3.3×10$^{-3}$), and 2.5-fold at 11 months (p=0.010) versus WT mice. Similarly NLRP3 levels were increased in S100A9Tg mice, with a 21.1-fold up-regulation at 2 months (p=0.059), 25.6-fold at 6 months (p=2.2×10$^{-4}$), and 12.1-fold at 11 months (p=0.018) (FIG. 25). Accordingly, formation of NLRP3 inflammasome complexes was significantly increased in an age-dependent fashion, with 2.6-fold greater co-localization in the 2 month old S100A9Tg transgenic mice (p=0.017), 3.3-fold in the 6 month (p=1.0×10$^{-6}$), and 3.2-fold in 11 month old mice (p=1.2×10$^{-3}$) (FIG. 25). Though transgenic mice illustrate a marked increase in mean cell area at each time point, there was no significant difference in cell size between WT and transgenic mice.

Figure 26:
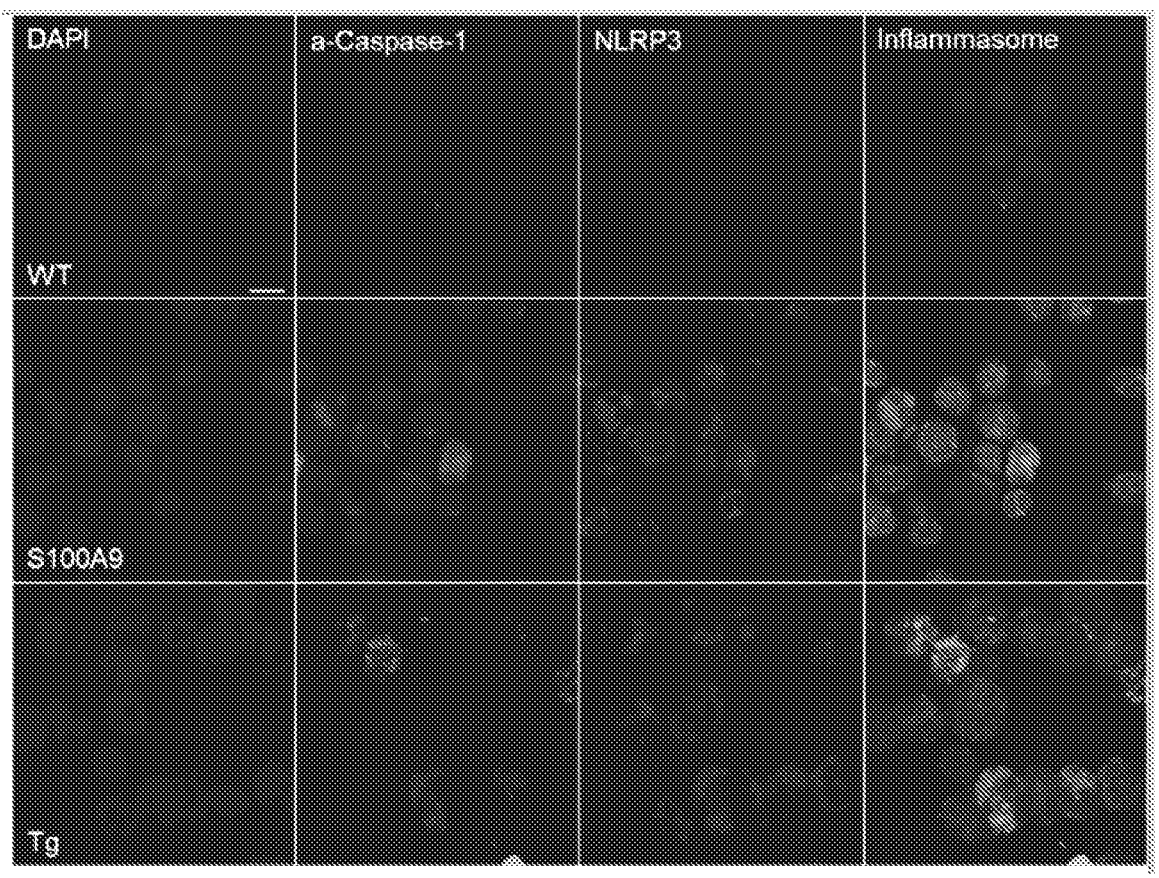
Figure 27:
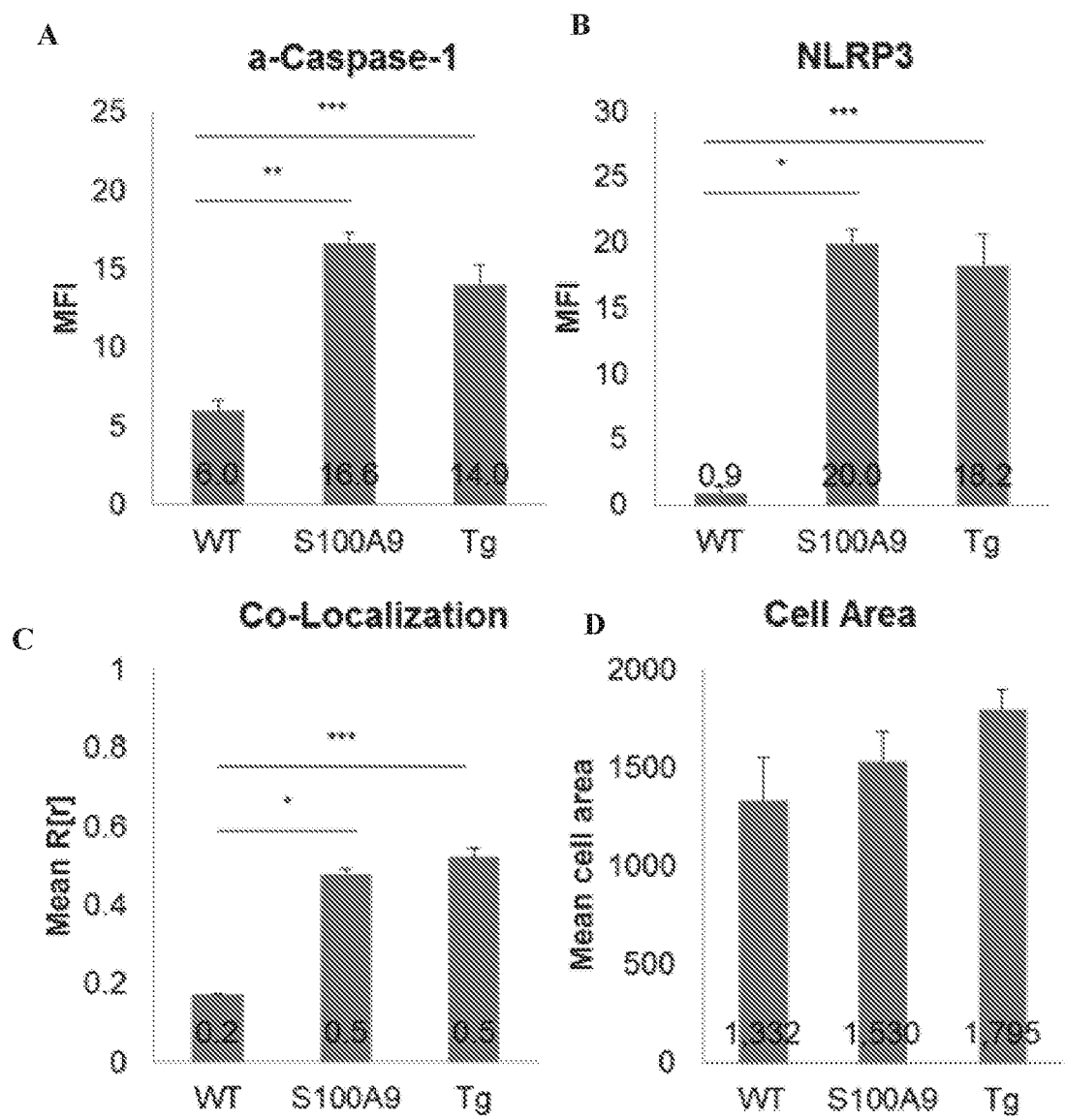
Figure 28:
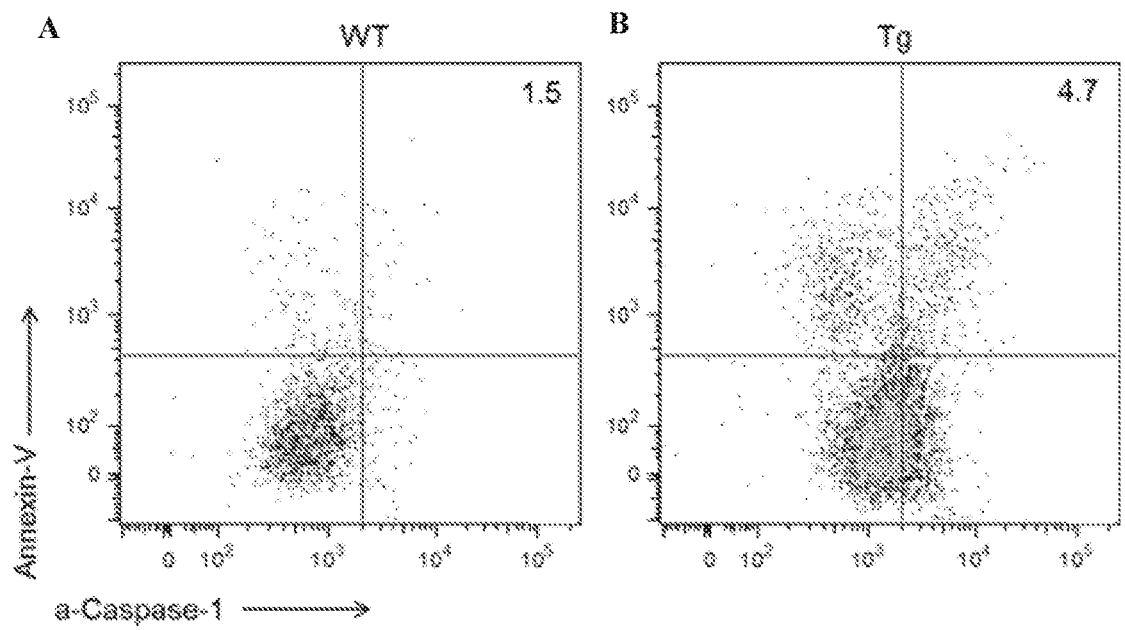
Figure 29:
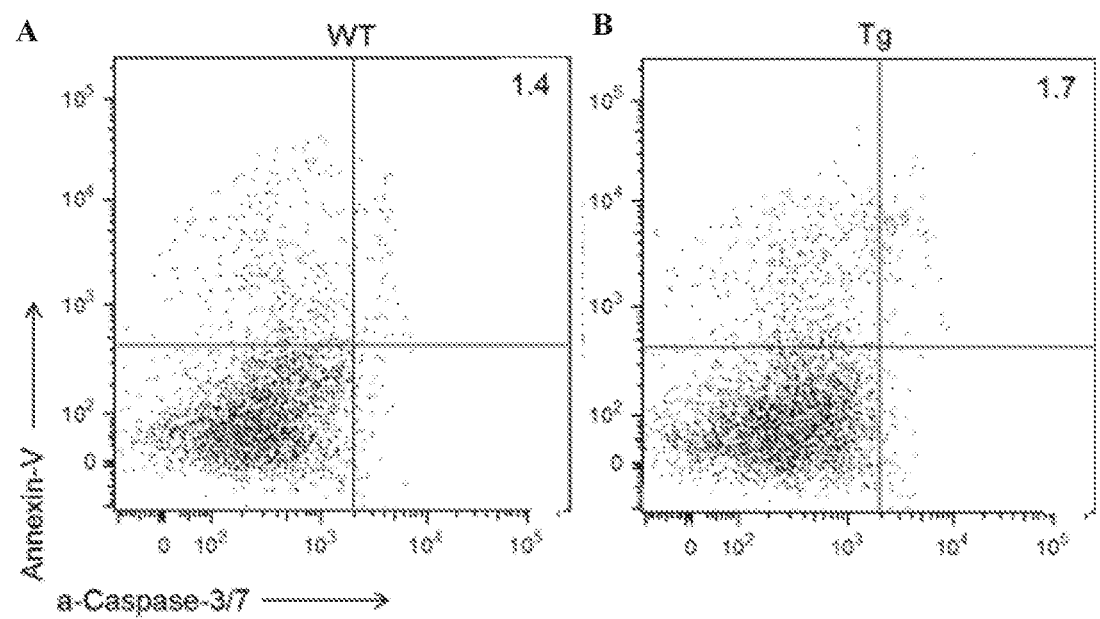
Figure 30:
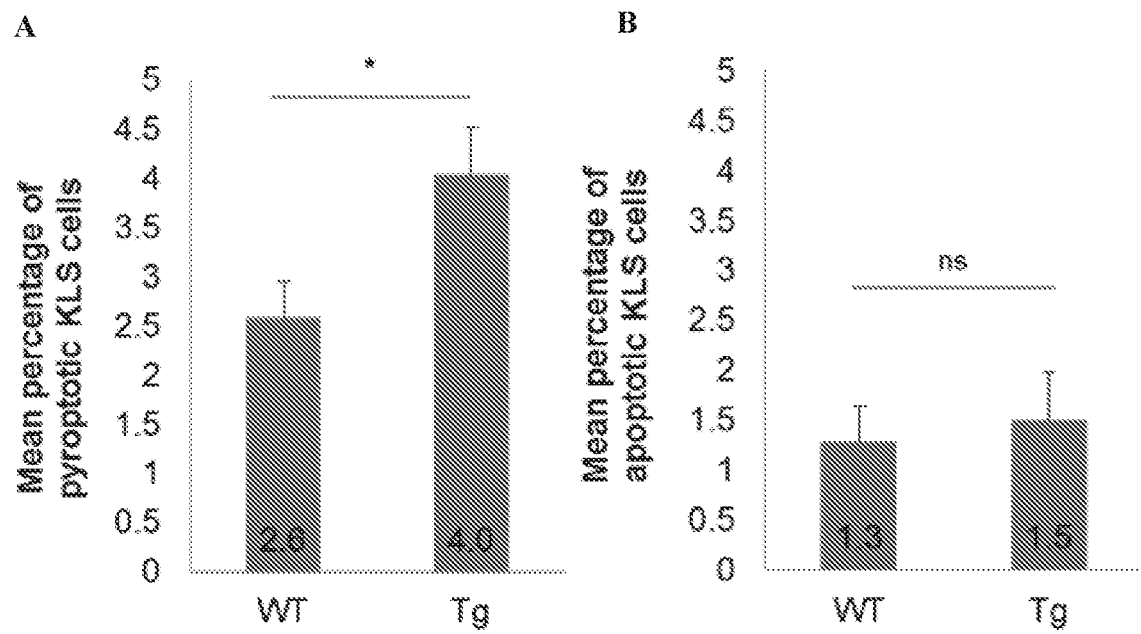
Figure 31:
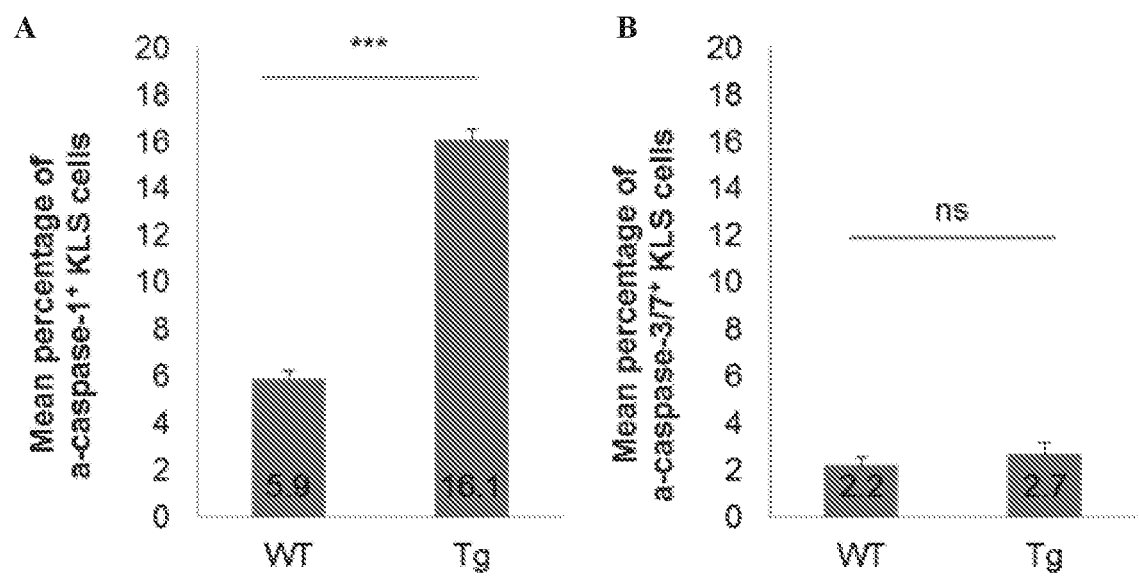
Figure 106:
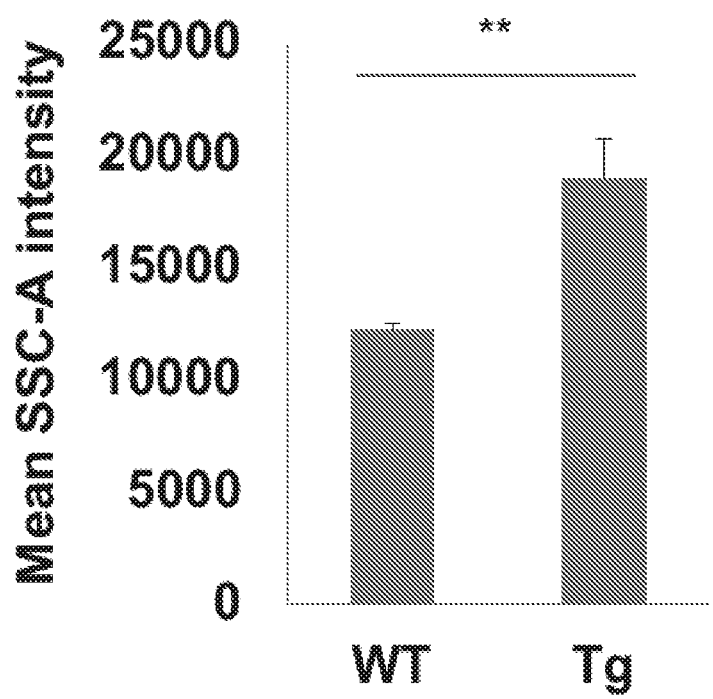
FIG. 106. Flow cytometric analysis of mean SSC-A intensity of BM cells isolated from WT (n=6) and S100A9Tg mice (n=6) (p=1.0×10$^{-2}$).

To test if S100A9 triggers pyroptosis in mouse hematopoietic cells, BM cells isolated from WT mice were treated with 5 µg/mL rhS100A9 and inflammasome formation was assessed by confocal microscopy (FIG. 26, 27). As predicted, MFI of a-caspase-1 and NLRP3 were both significantly increased after rhS100A9 treatment (n=2) versus controls (n=2) (p=7.5×10$^{-3}$ and 0.017, respectively). Notably, MFI values from rhS100A9 treated BM cells of WT mice were comparable to those manifest in the BM cells of S100A9 transgenic mice (n=13) (FIG. 27), and rhS100A9 treatment of WT BM cells was associated with a marked induction of inflammasome complexes (p=0.023). To assess the extent of pyroptosis versus apoptosis in the corresponding mice, BM cells were isolated from 7 month old WT (n=6) and 9 month old S100A9Tg mice (n=6). Active caspase-1 and a-caspases-3/7 were assessed by flow cytometry in the KLS (c-Kit$^+$Lin$^-$Sca-1$^+$) hematopoietic stem and progenitor cell population (FIG. 28, 29). The mean percentage of pyroptotic KLS cells was significantly increased in the S100A9Tg animals versus WT mice (p=0.038), whereas there were no significant differences in the mean percentage of apoptotic cells (FIG. 30). Additionally, the total percentage of a-caspase-1$^+$ KLS cells was increased 2.7-fold in the S100A9Tg mice compared to WT mice (p=2.75×10$^{-4}$), with no change in the total a-caspase-3/7$^+$ KLS population (FIG. 31). S100A9Tg BM cells also demonstrated a significant increase in mean cell area, as assessed by SSC-A intensity measurements (FIG. 106).

Figure 32:
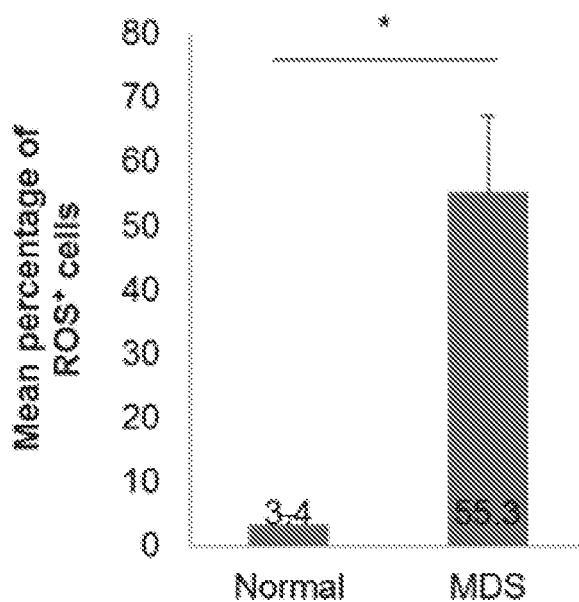
Figure 33:
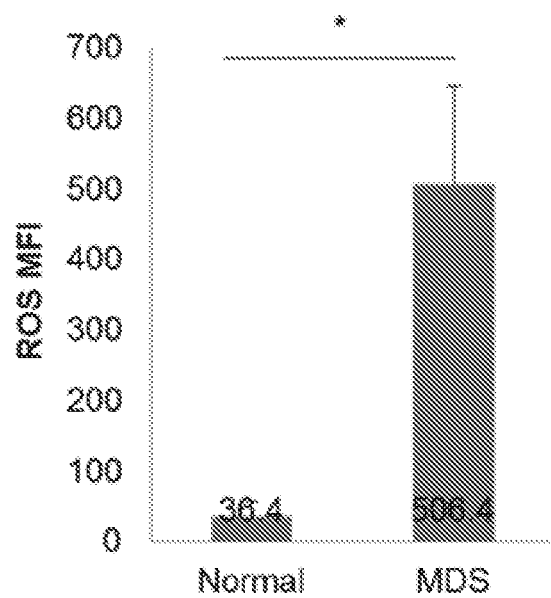
Figure 34:
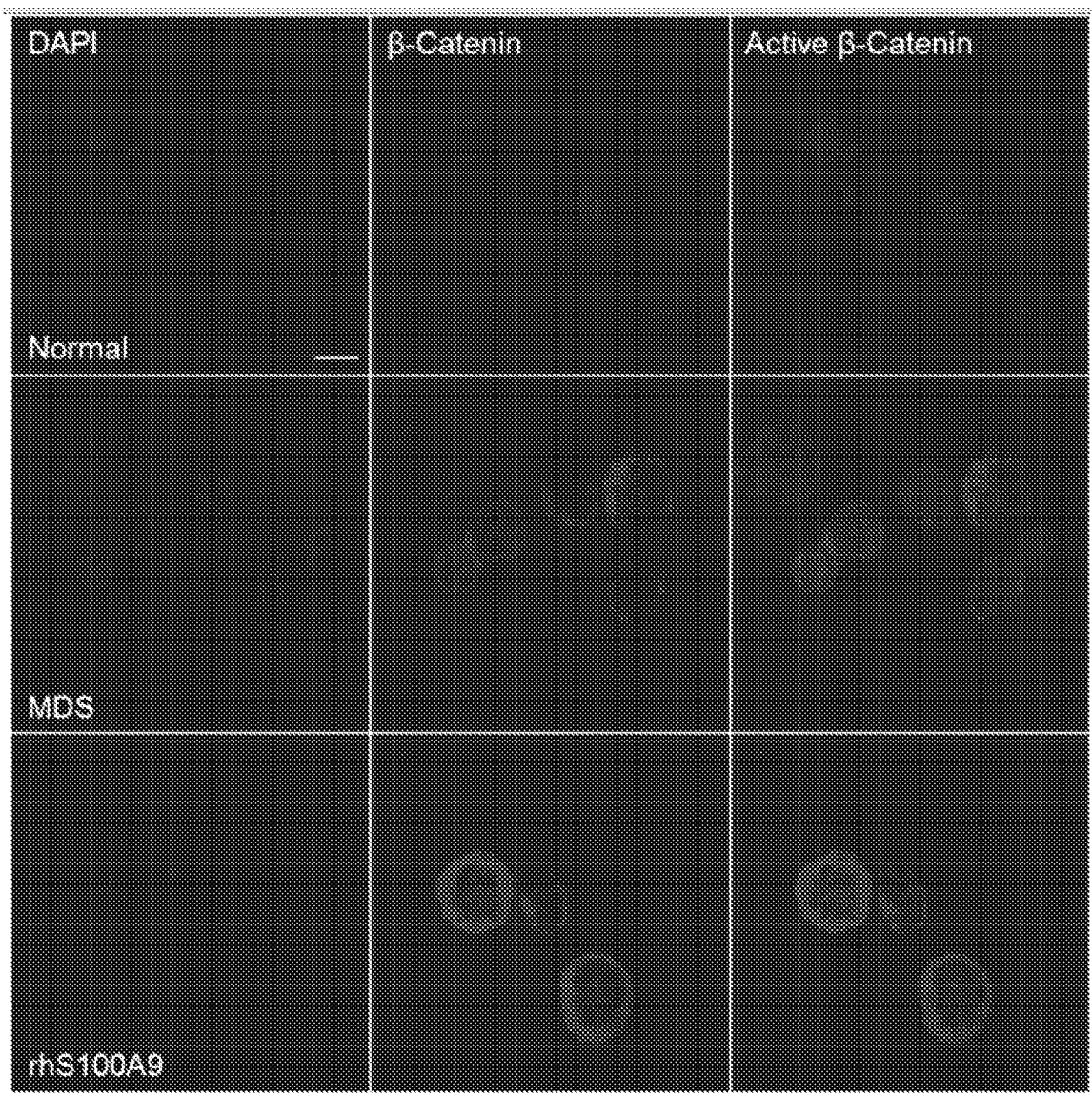
Figure 35:
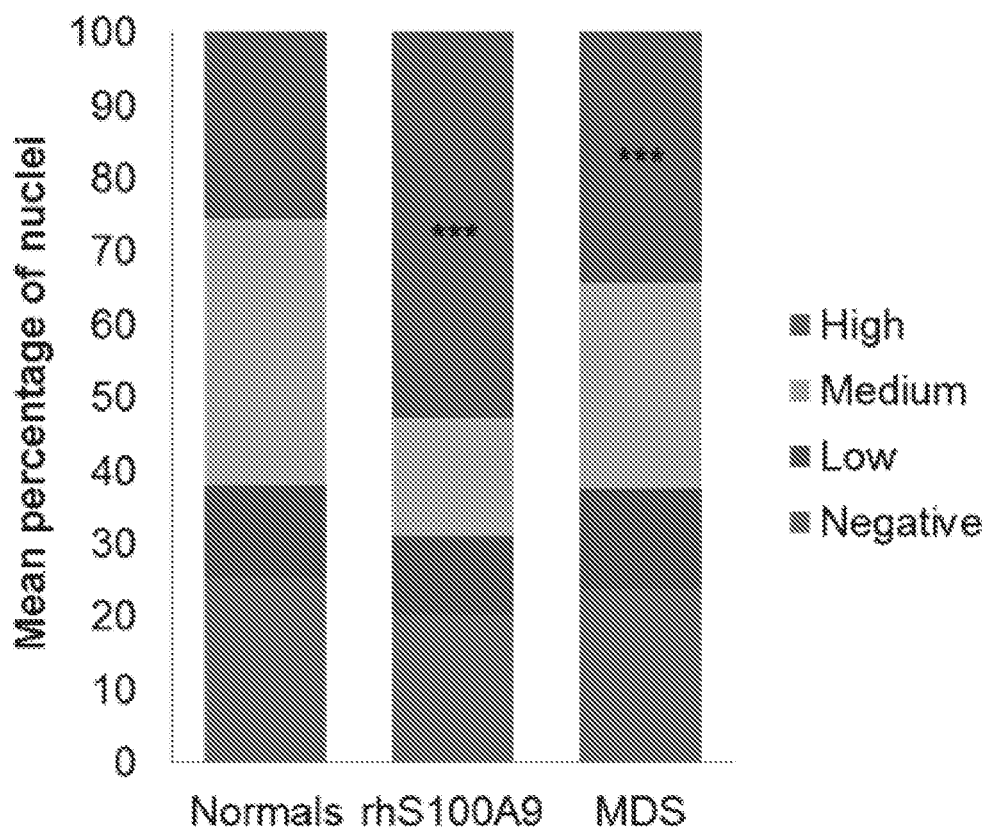
Figure 53:
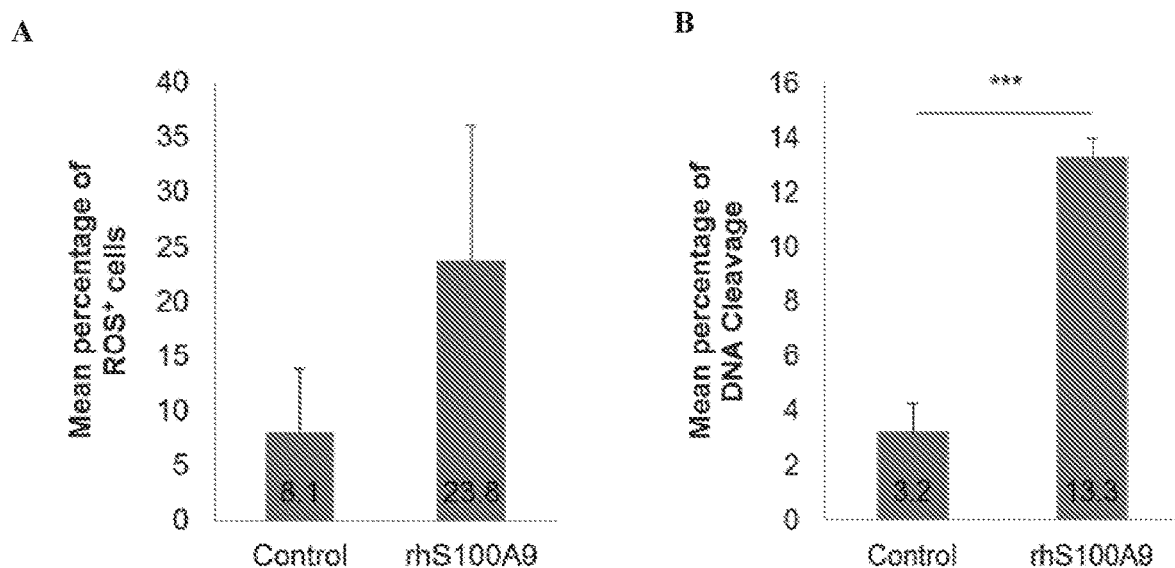
FIG. 53. Recombinant human S100A9 is sufficient to induce ROS and β-catenin activation in monocytic cells. U937 cells were treated with 5 µg/mL rhS100A9 for 24 hours. Subsequently, (A) the percentage of ROS positive cells was assessed by flow cytometry and (B) DNA damage assessed by comet assay.
Figure 54:
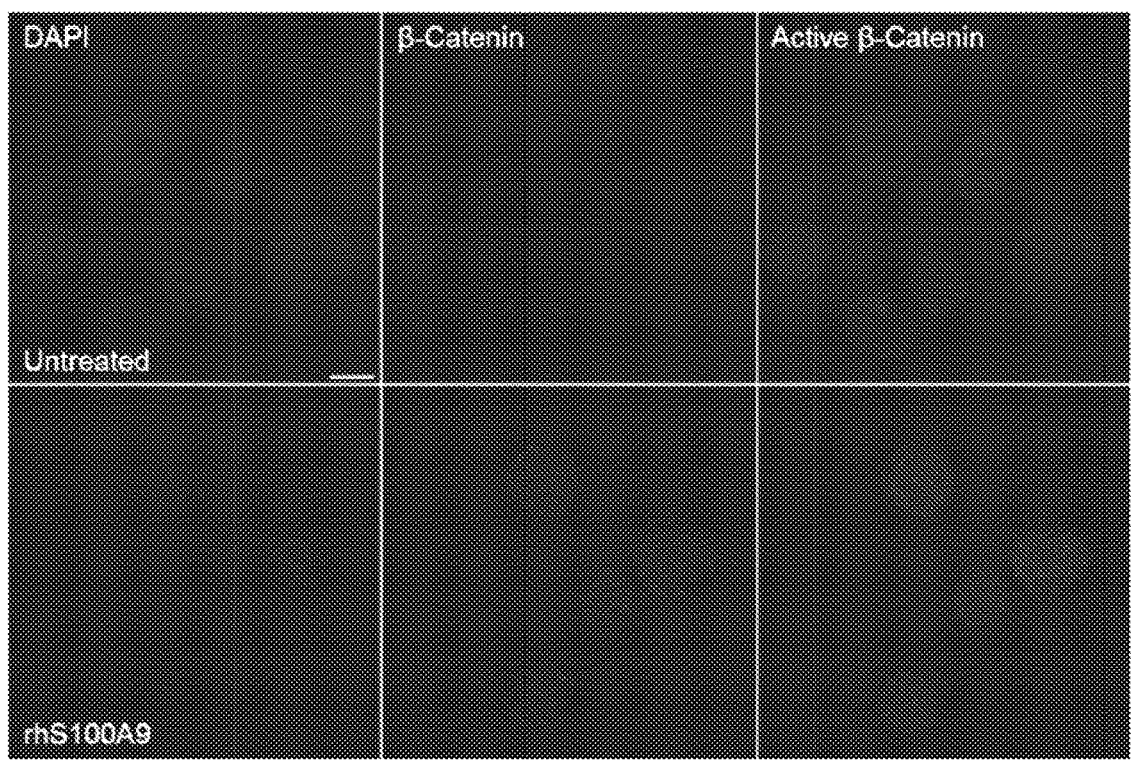
FIG. 54. Representative micrograph of β-catenin (1890× magnification, 10 µm scale) in untreated and treated cells by confocal microscopy. DAPI (first column), β-catenin (second column); merged image shows nuclear localization of β-catenin (third column), reflecting its active form.
Figure 55:
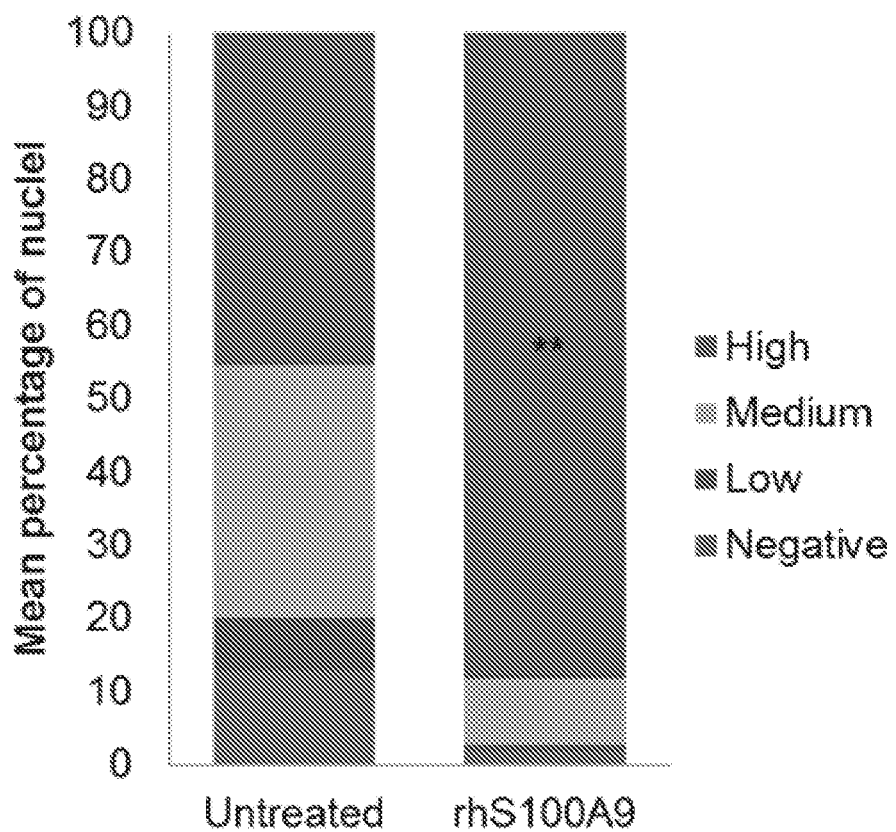
FIG. 55. β-catenin confocal images were quantified and scored based on the presence of no, low, medium, or high expression of nuclear β-catenin. Cells were pooled for analysis. There is a statistically significant increase in high nuclear β-catenin expression following treatment with rhS100A9 ($p=2.4\times10^{-3}$). Error bars: SE, $p<0.01$ and *$p<0.001$. Data are representative of three independent experiments.
Figure 56:
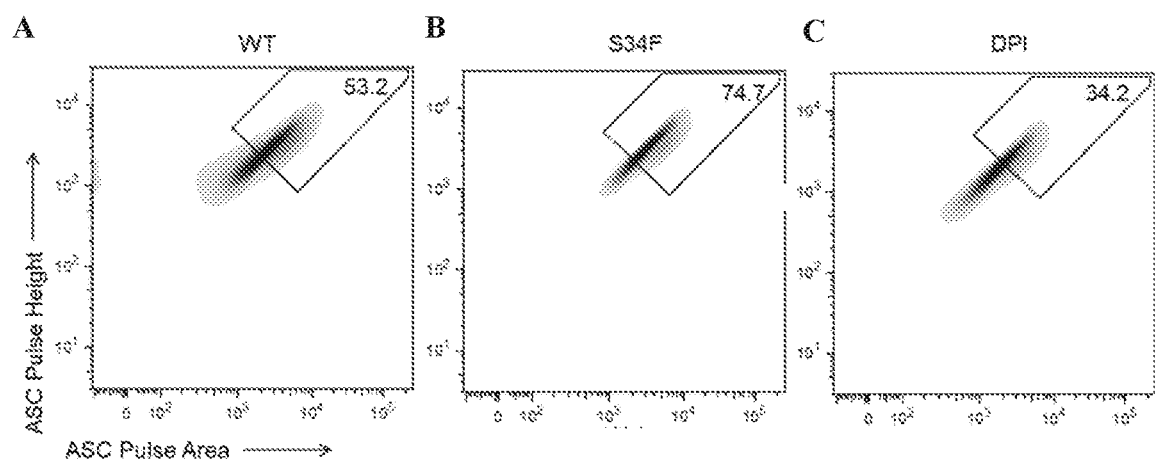
FIGS. 56-63 show that U2AF1 mutations manifest in MDS provoke pyroptosis. The ability of U2AF1 mutations to induce pyroptosis was assessed in S34F mutant cell lines. Error bars: SE, *$p<0.05$, $p<0.01$, and *$p<0.001$. Data are representative of three independent experiments.
Figure 57:
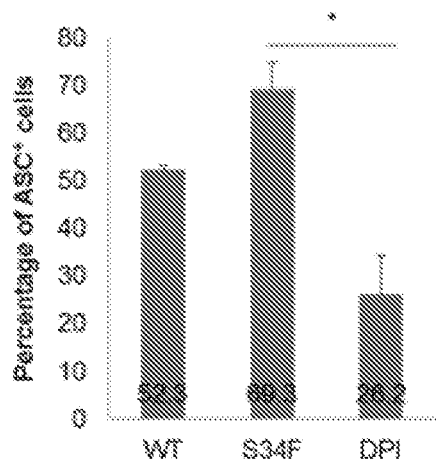
Figure 58:
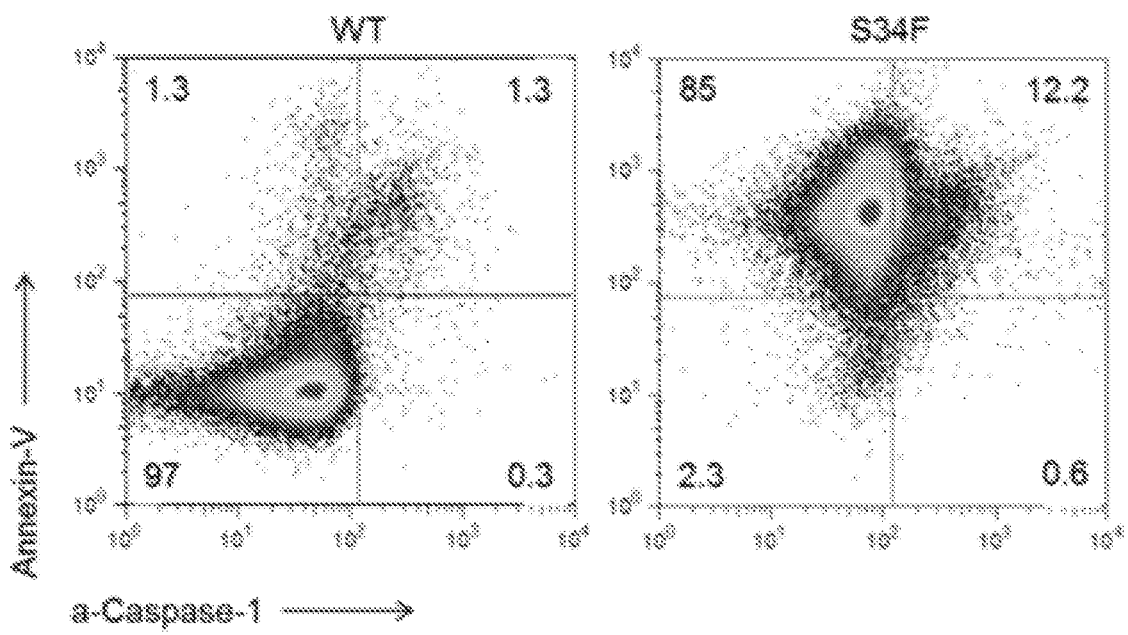
Figure 59:
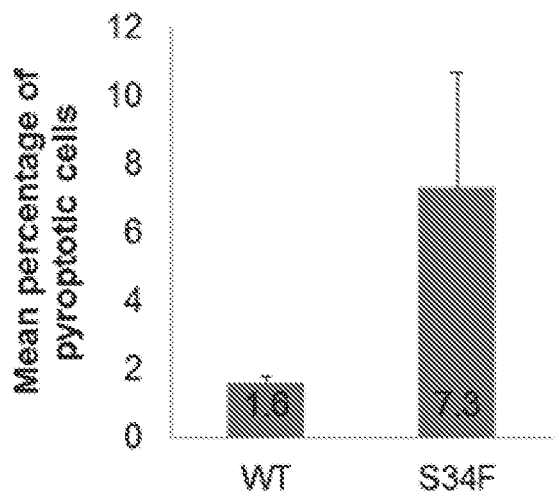
Figure 60:
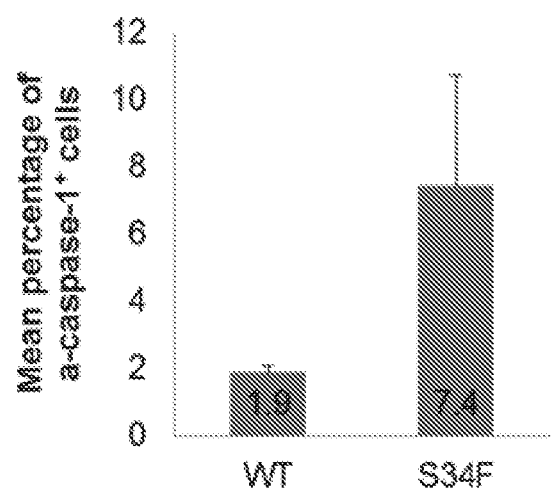
Figure 61:
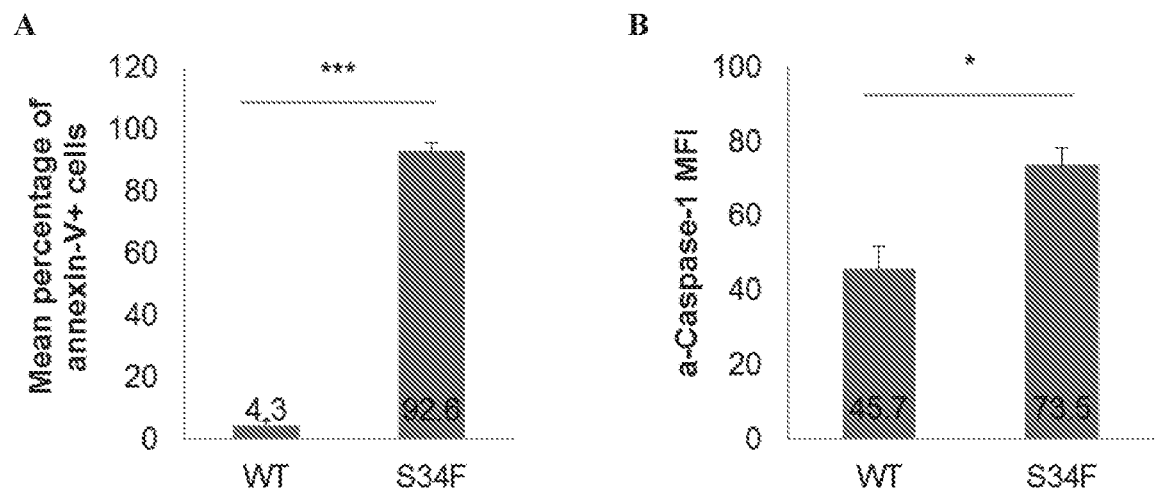
Figure 62:
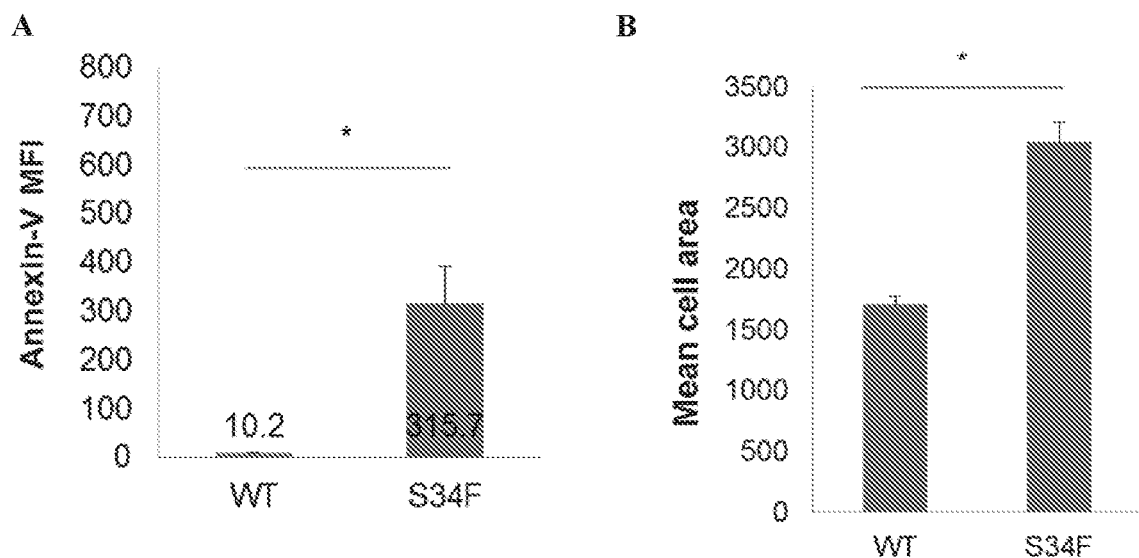

S100A 9 and MADS Gene Mutations Trigger Pyroptosis and β-Catenin Activation Via ROS ROS act as DAMP intermediates that activate the Wnt/β-catenin axis (Rharass T, et al. J Biol Chem. 2014 289(40): 27937-51; Kajla S, et al. FASEB J. 2012 26(5):2049-59). Thus, ROS generated by either S100A9 or somatic gene mutations that are manifest in MDS may contribute to self-renewal and clonal expansion via activation of β-catenin. Monocytic U937 cells treated with 5 µg/mL rhS100A9 for 24 hours displayed a 2.9-fold increase in the mean percentage of ROS-positive cells and a 4.1-fold increase in DNA damage (p=1.5×10$^{-9}$), compared to untreated cells (FIG. 53A, 53B). Accordingly, mean percentage of ROS positive cells was increased in MDS BM-MNC (n=5) 16.5-fold compared to normal controls (n=2) (p=0.011) (FIG. 32), with a corresponding significant increase in ROS MFI (p=0.028) (FIG. 33). Further, confocal fluorescence microscopy analyses demonstrated marked increases in the levels of nuclear (activated) β-catenin in rhS100A9 treated U937 cells compared to untreated cells ($p=2.4 \times 10^{-3}$) (FIG. 54, 55), and elevated levels of nuclear β-catenin were manifest in patient BM-MNC (n=6) compared to normal donors (n=3), as well as in normal BM-MNC treated with 5 μg/mL rhS100A9 for 24 hours compared to controls (p=0.043 and $p=6.38 \times 10^{-7}$, respectively) (FIG. 34, 35). Finally, β-catenin gene expression was increased 9.5-fold in the BM cells of S100A9Tg mice versus WT BM cells, with corresponding up-regulation of Wnt/β-catenin target genes (FIG. 107).

Figure 36:
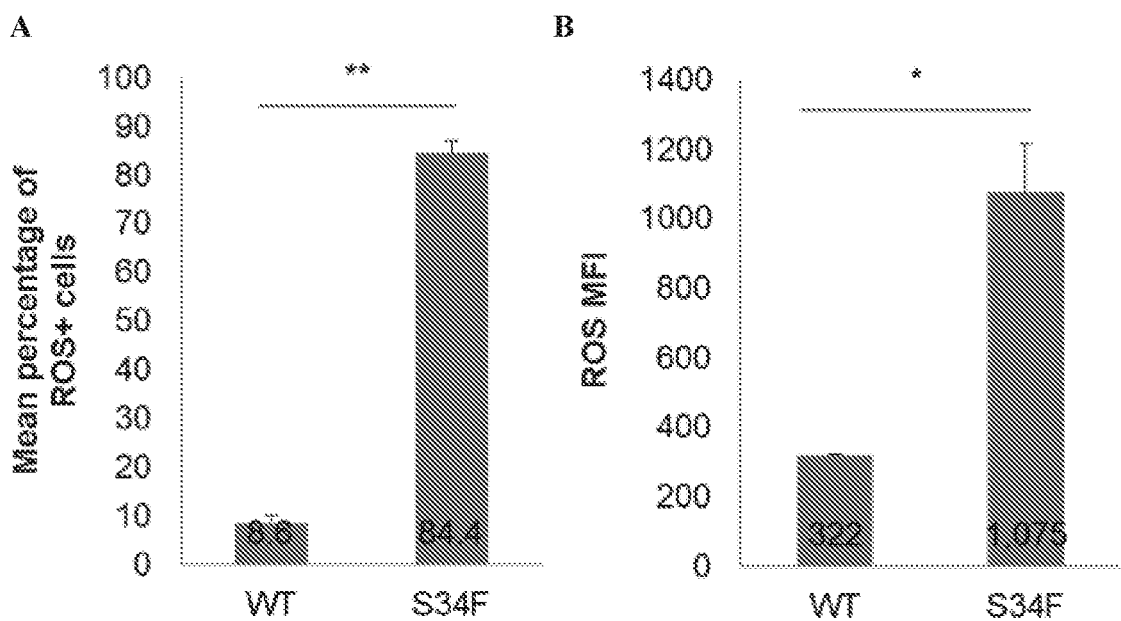
Figure 37:
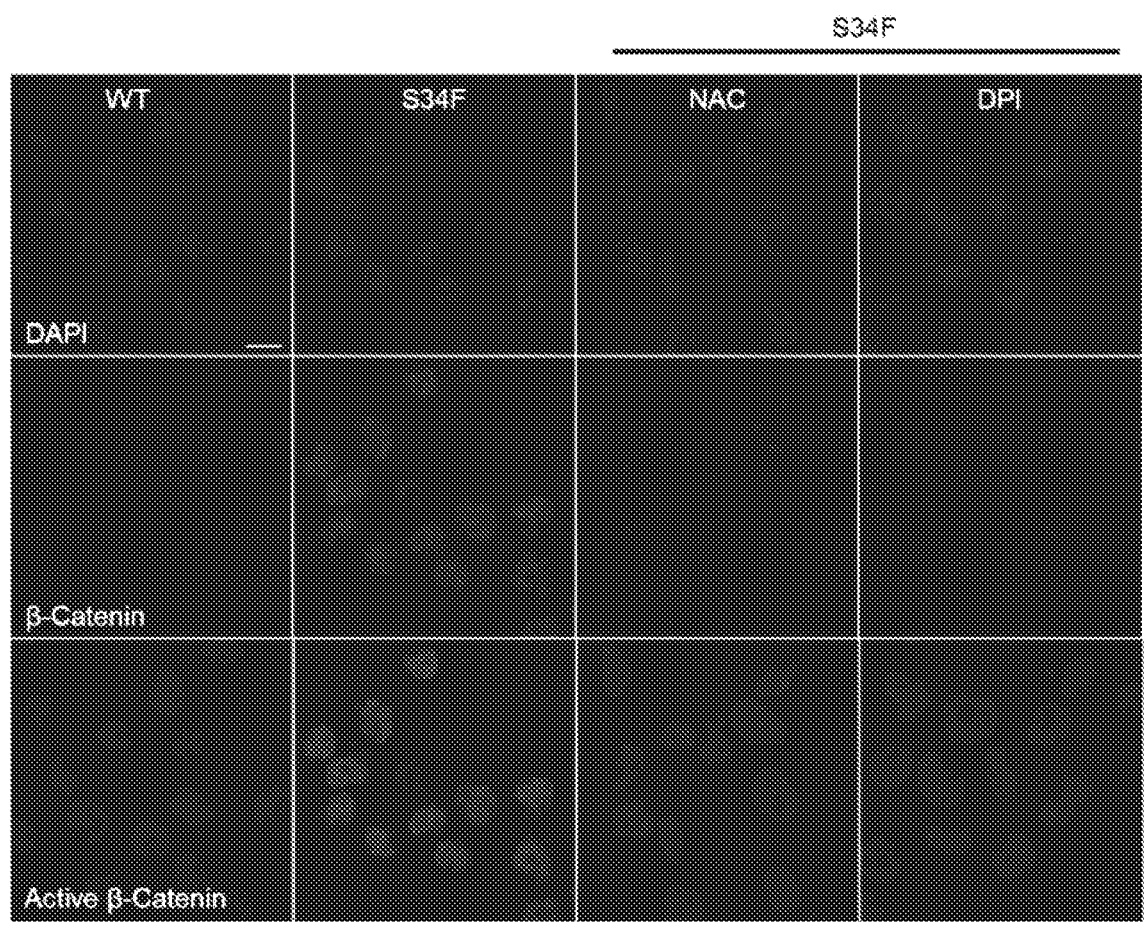
Figure 38:
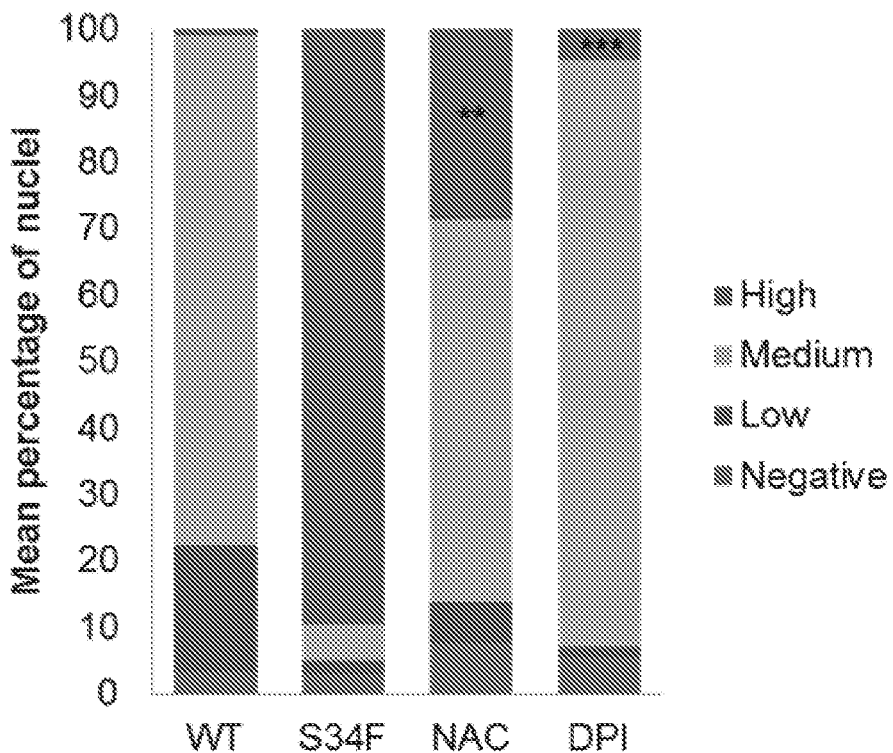
Figure 63:
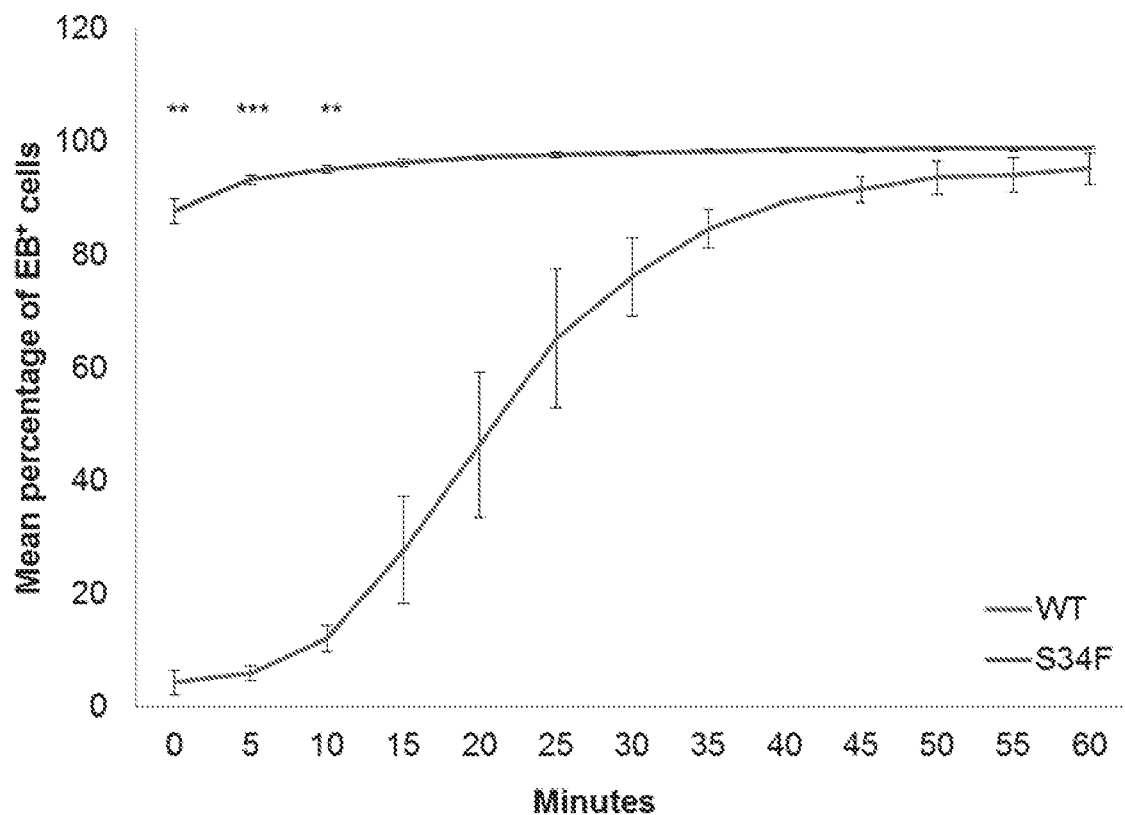

To test if somatic gene mutations manifest in MDS trigger pyroptosis and enhance self-renewal via activation of β-catenin, this circuit was first investigated in cells engineered to express MDS-associated mutants of the U2AF1 splicing factors (Yoshida K, et al. Nature. 2011 478(7367): 64-9). The percentage of pyroptotic cells was increased 4.6-fold in S34F U2AF1 mutant-versus WT U2AF1-expressing cells, accompanied by increased levels of a-caspase-1 (p=0.044) and annexin-V (p=0.021) (FIGS. 56-62). U2AF1-S34F-expressing cells also displayed significant increases in mean cell area (p=0.035) and ethidium bromide influx (FIG. 62B, 63), the mean percentage of ROS⁺ cells ($p=1.5 \times 10^{-3}$), ROS MFI (p=0.032) (FIG. 36A, 36B) and nuclear localization of β-catenin (FIG. 37, 38). Notably, treatment of U2AF1-S34F mutant cells with the anti-oxidant N-acetylcysteine (NAC) or the NADPH oxidase (NOX) inhibitor DPI effectively reduced β-catenin activation in mutant cells ($p=3.8 \times 10^{-3}$ and $p=2.5 \times 10^{-6}$, respectively) (FIG. 37, 38), indicating that β-catenin activation is initiated by NOX-derived ROS generation.

Figure 64:
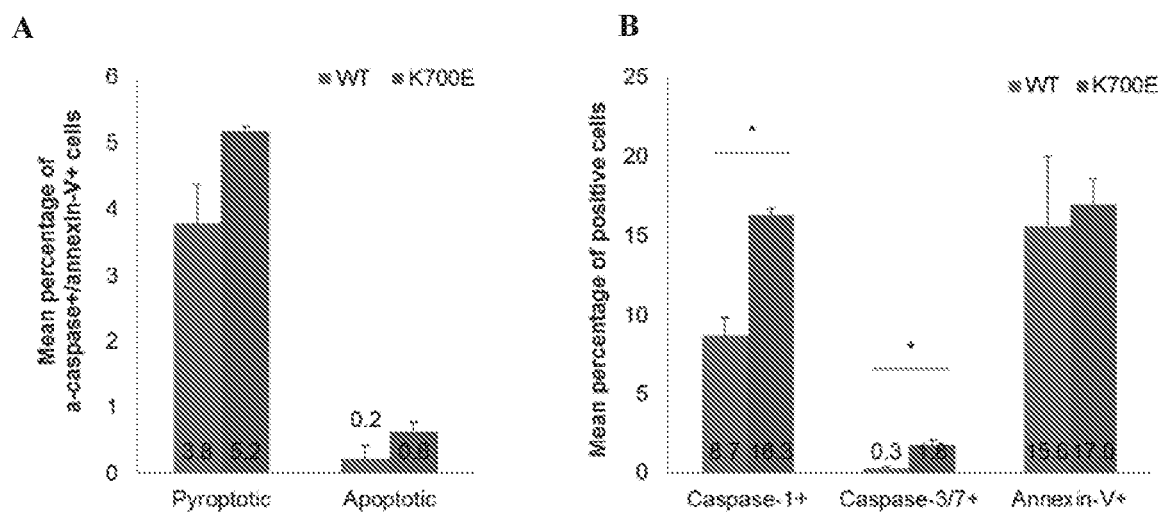
FIG. 64. SF3B1 K700E induces pyroptosis. The ability of the SF3B1 K700E conditional knock-in mutation to induce pyroptosis was assessed in BM cells harvested from WT (n=3) and mutant (n=3) mice. (A) Quantitation of the percentage of pyroptotic versus apoptotic cells. (B) Mean percentage of total a-caspase-1$^+$, a-caspase-3/7$^+$, and annexin-V$^+$ cells.
Figure 65:
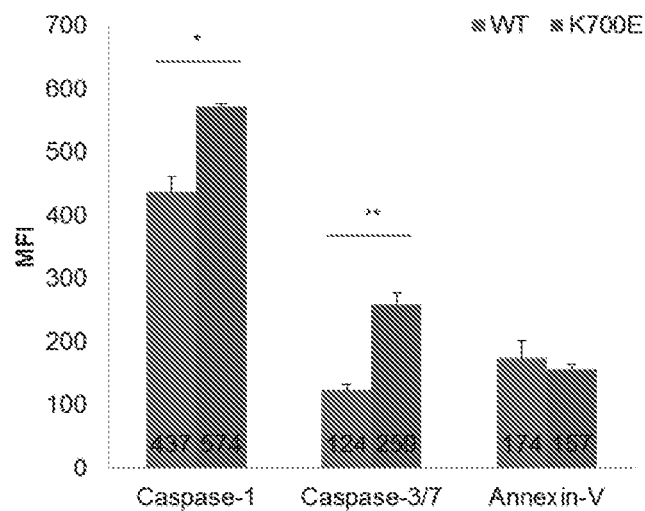
FIG. 65. MFI values for a-caspase-1, a-caspase-3/7, and annexin-V in the mutant and WT cells.
Figure 66:
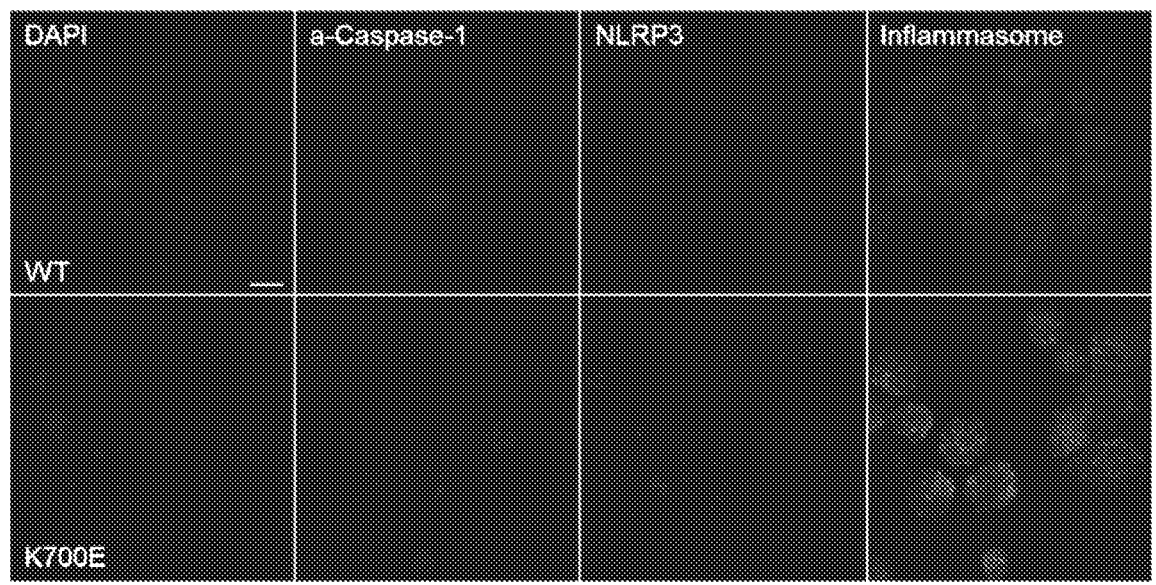
FIG. 66. Representative micrograph (2520× magnification, 7.5 µm scale) depicting inflammasome formation in the WT and K700E mutant cells. DAPI (first column), a-caspase-1 (second column), NLRP3 (third column); merged image shows inflammasome formation (fourth column).
Figure 67:
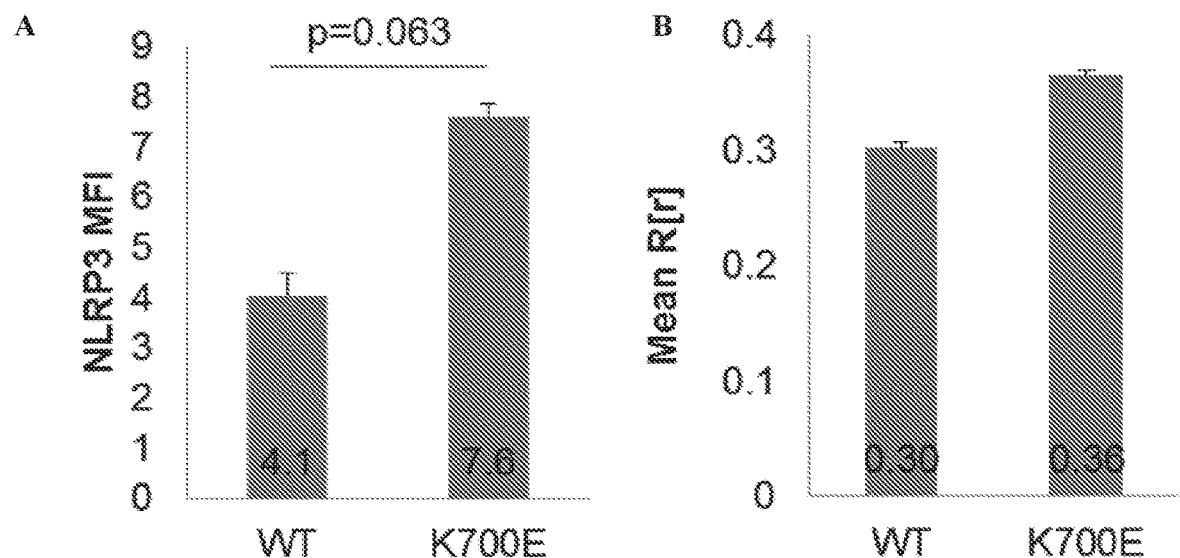
FIG. 67. Quantitative analysis of a-caspase-1/NLRP3 confocal images showing (A) NLRP3 and (B) colocalization.
Figure 68:
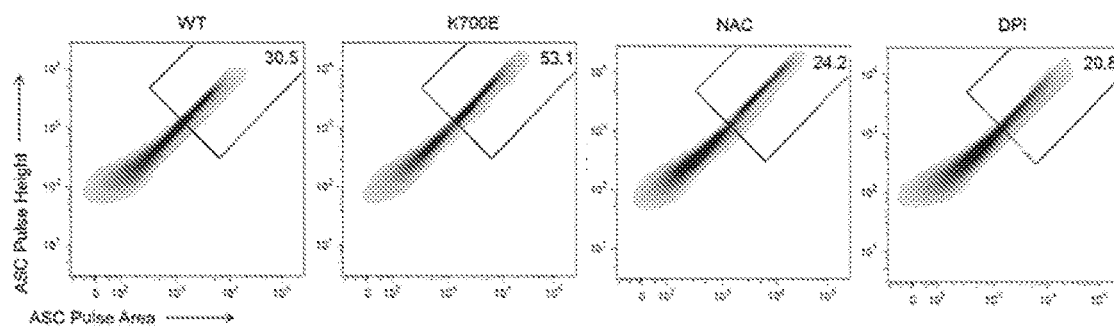
FIG. 68. Representative density plot of inflammasome formation based on the detection of fluorescence pulse differences in ASC.
Figure 69:
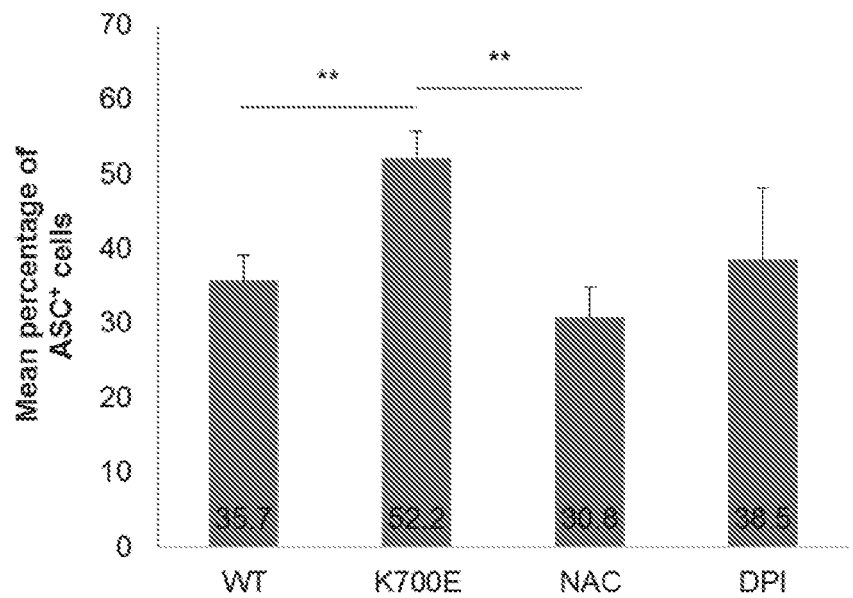
FIG. 69. Quantitation of ASC in WT (n=6), K700E (n=6), and K700E cells treated with NAC (n=6) or DPI (n=3) for 24 hours.
Figure 70:
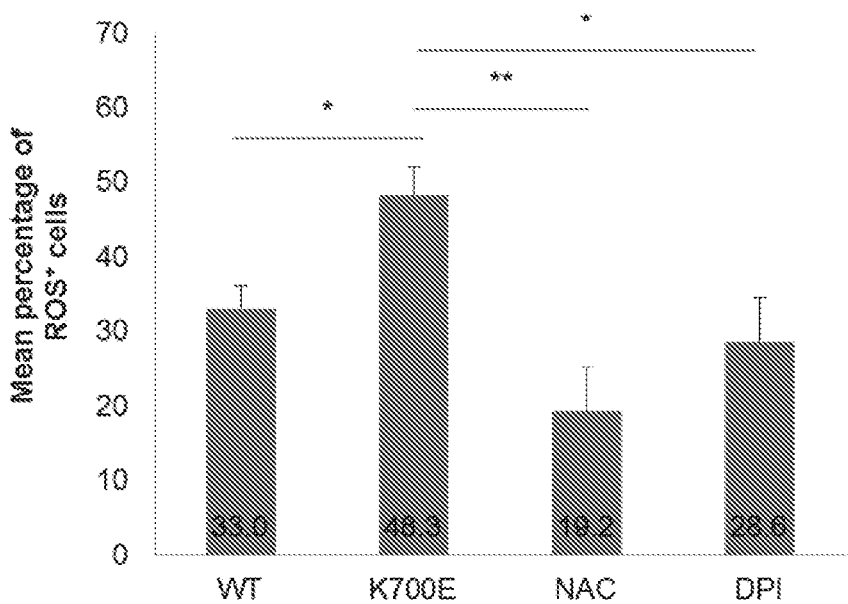
FIGS. 70-73 show that SF3B1 K700E supports self-renewal through β-catenin activation. The ability of the SF3B1 K700E conditional knock-in mutation to support self-renewal through activation of β-catenin was assessed in BM cells harvested from WT (n=6) and mutant (n=6) mice. Error bars: SE, *$p<0.05$ and **$p<0.01$.
Figure 71:
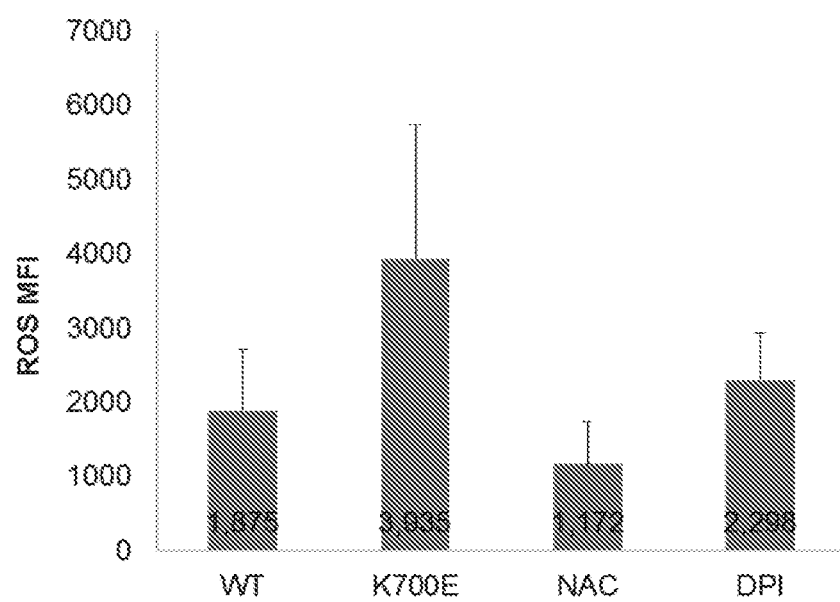
Figure 72:
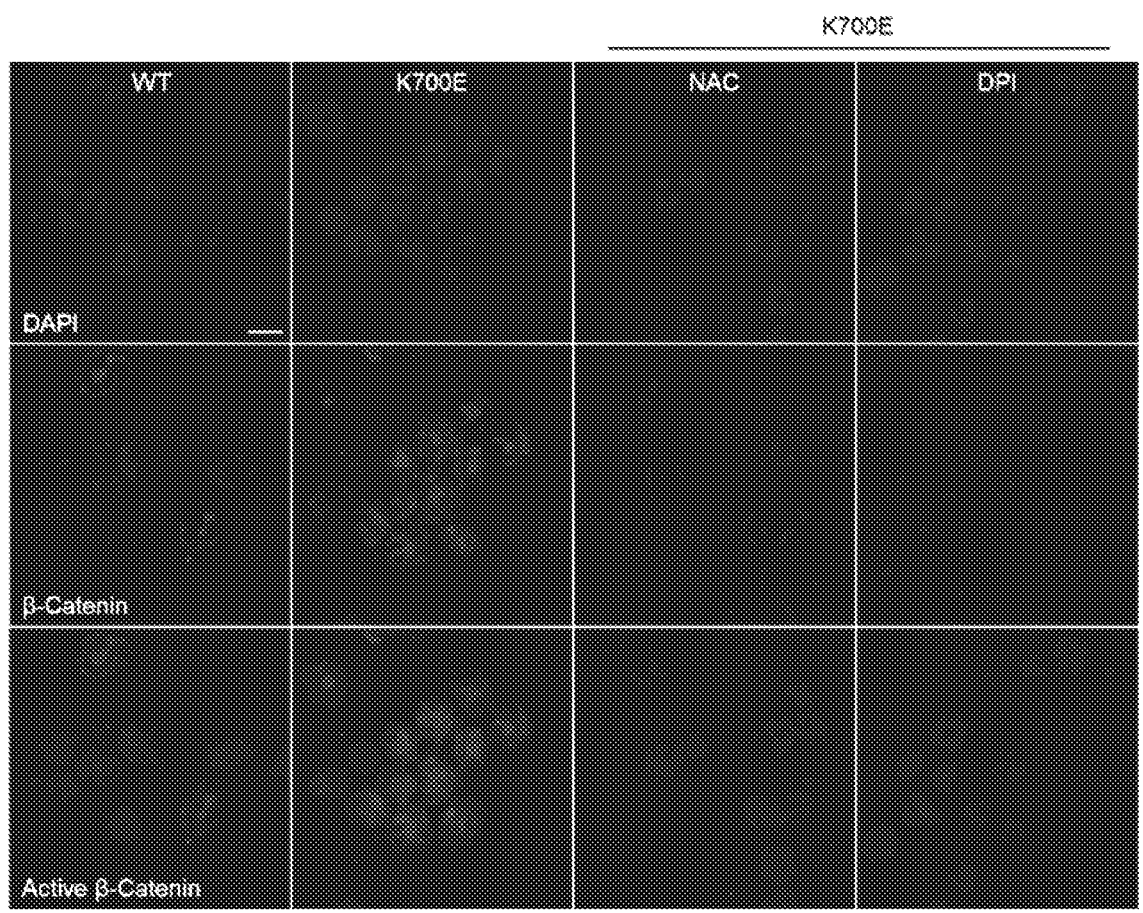
Figure 73:
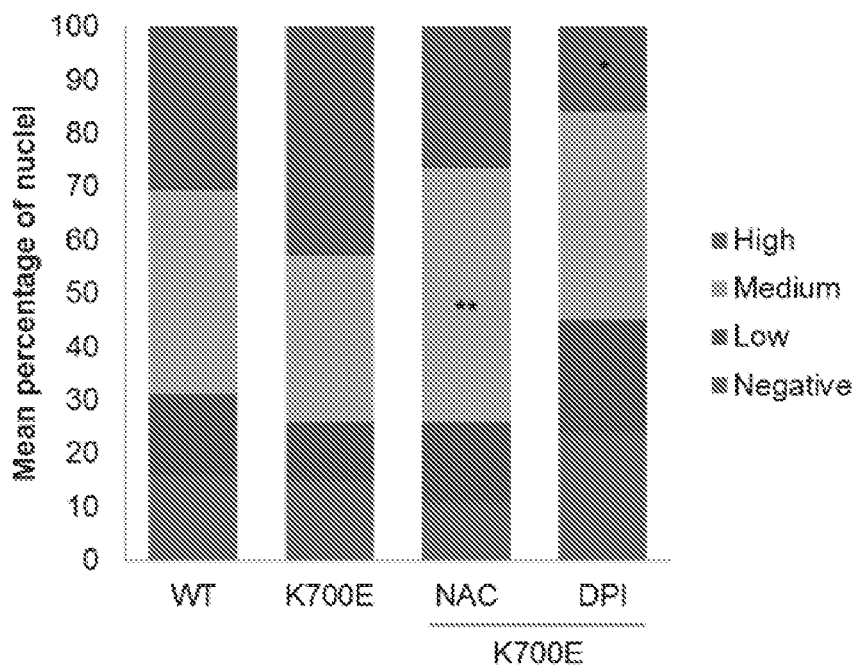
Figure 74:
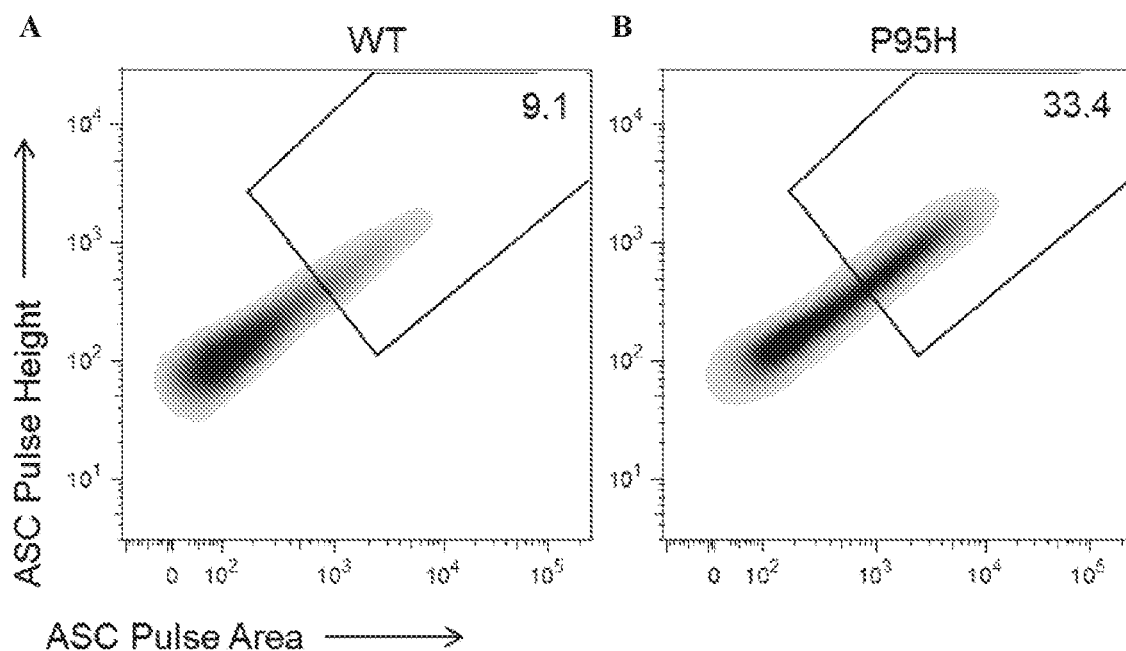
FIGS. 74-80 show that SRSF2 mutants induce pyroptosis and support self-renewal through β-catenin. HEK293T cells were transiently transfected with WT and P95H mutant SRSF2. Data are representative of three independent experiments, and of the GFP$^+$ transfected population.
Figure 75:
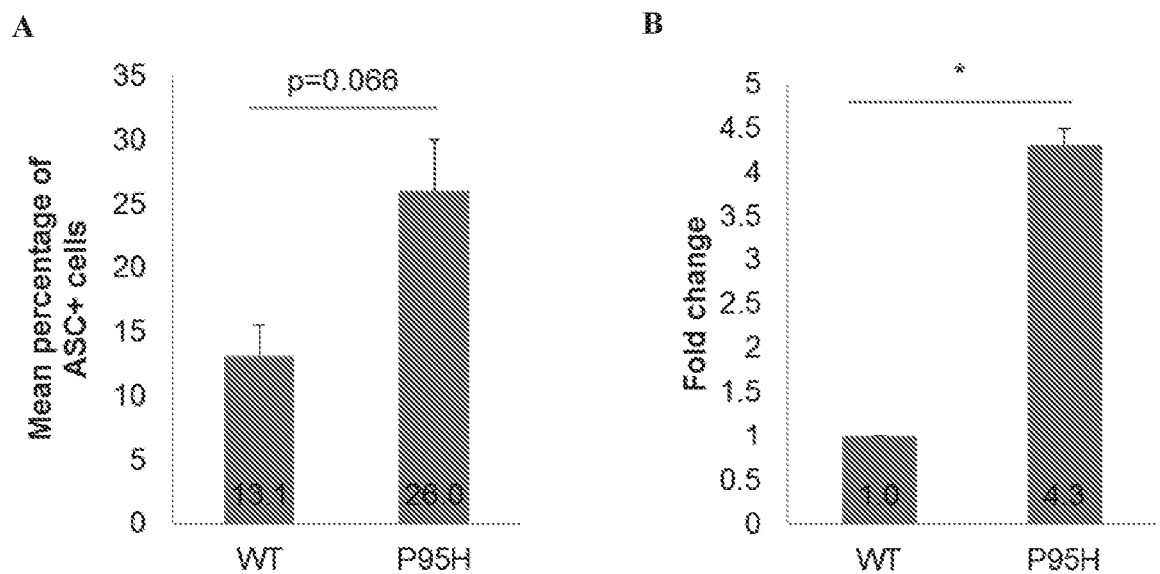
Figure 76:
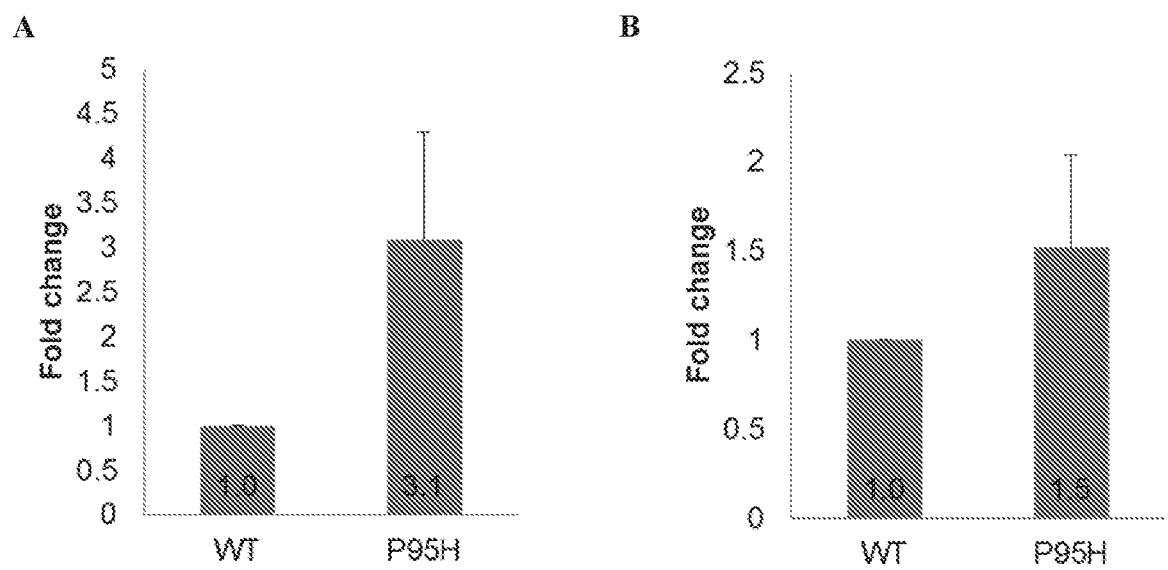
Figure 77:
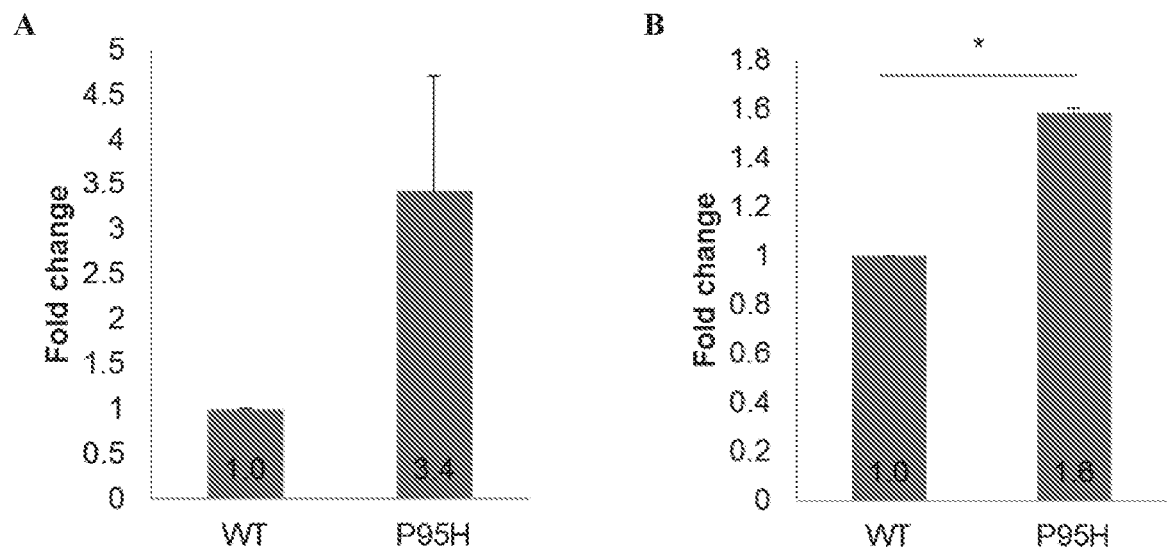
Figure 78:
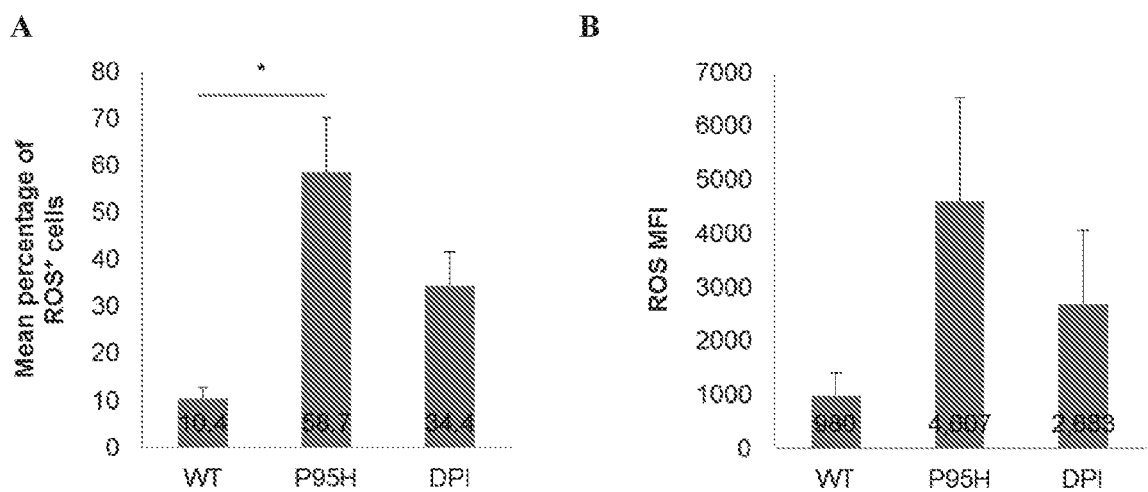
Figure 79:
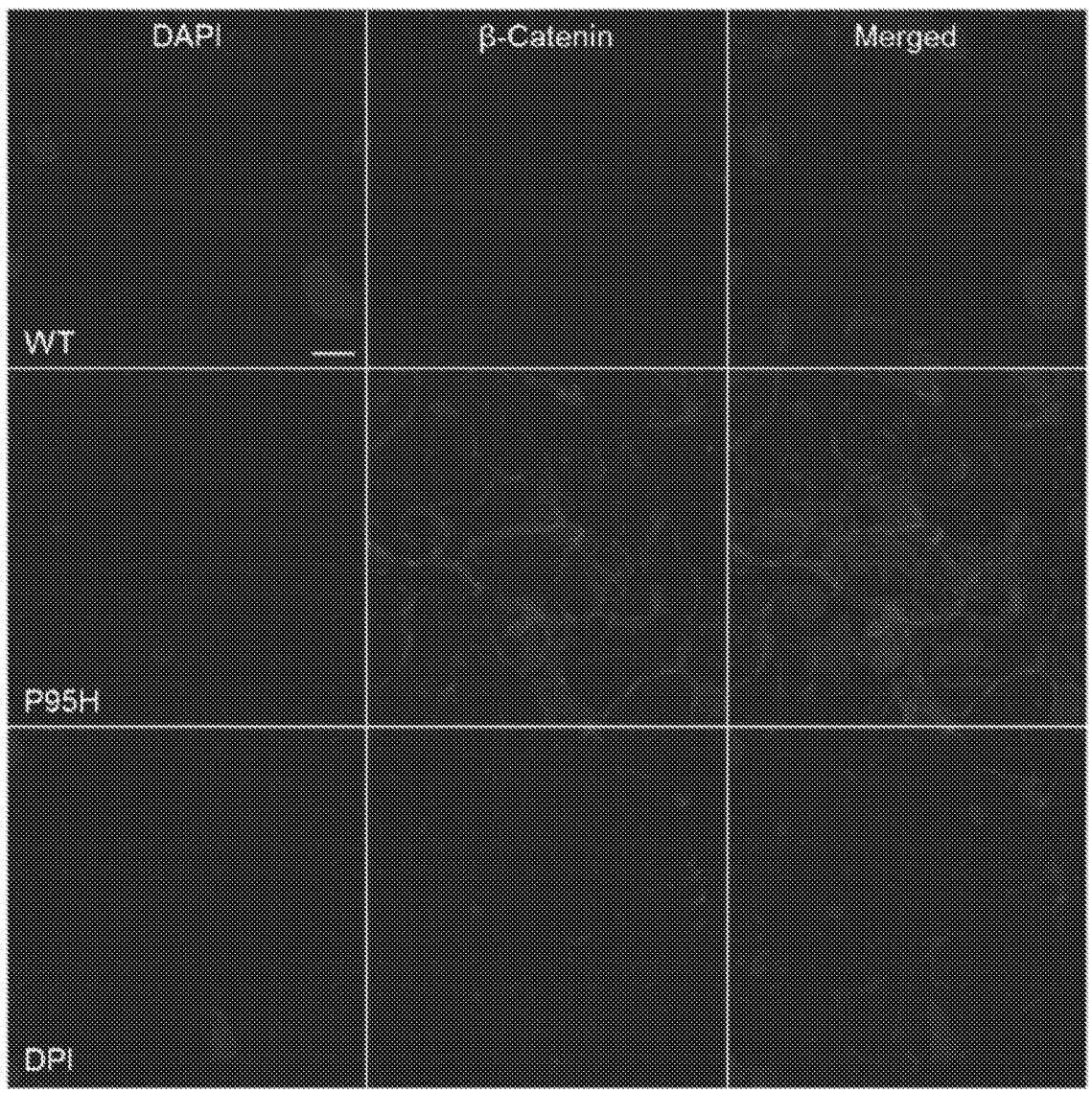
Figure 80:
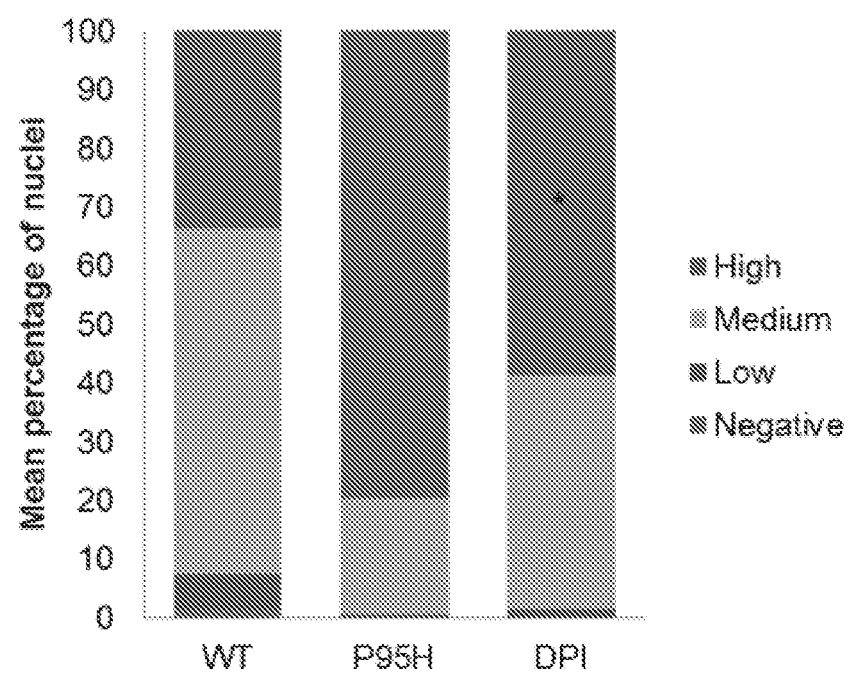
Figure 81:
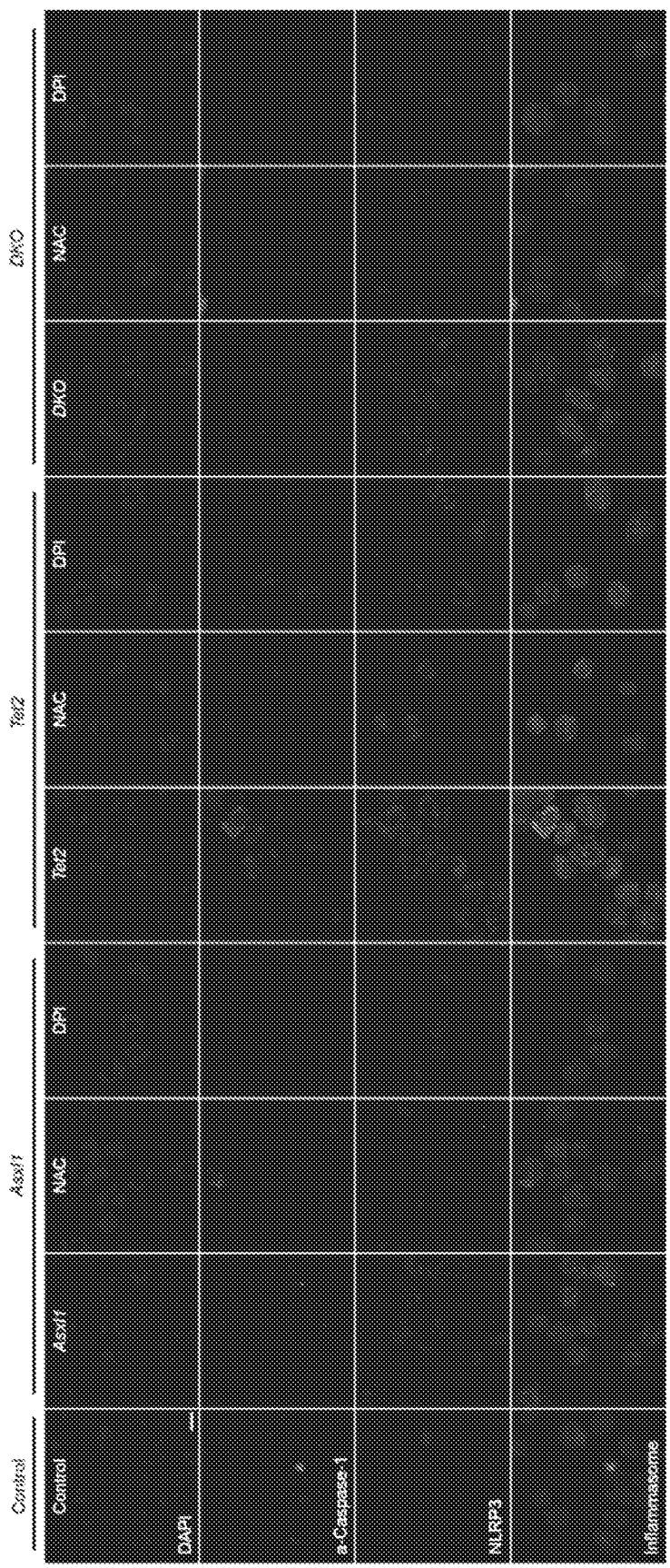
FIGS. 81-88 show that Asxl1 and Tet2 deletions are sufficient to induce pyroptosis. The ability of deletions in Asxl1 and Tet2 to induce pyroptosis was assessed in BM cells isolated from Asxl1 KO, Tet2 KO, and DKO cells, compared to control cells. Error bars: SE, *$p<0.05$, $p<0.01$, and *$p<0.001$.
Figure 82:
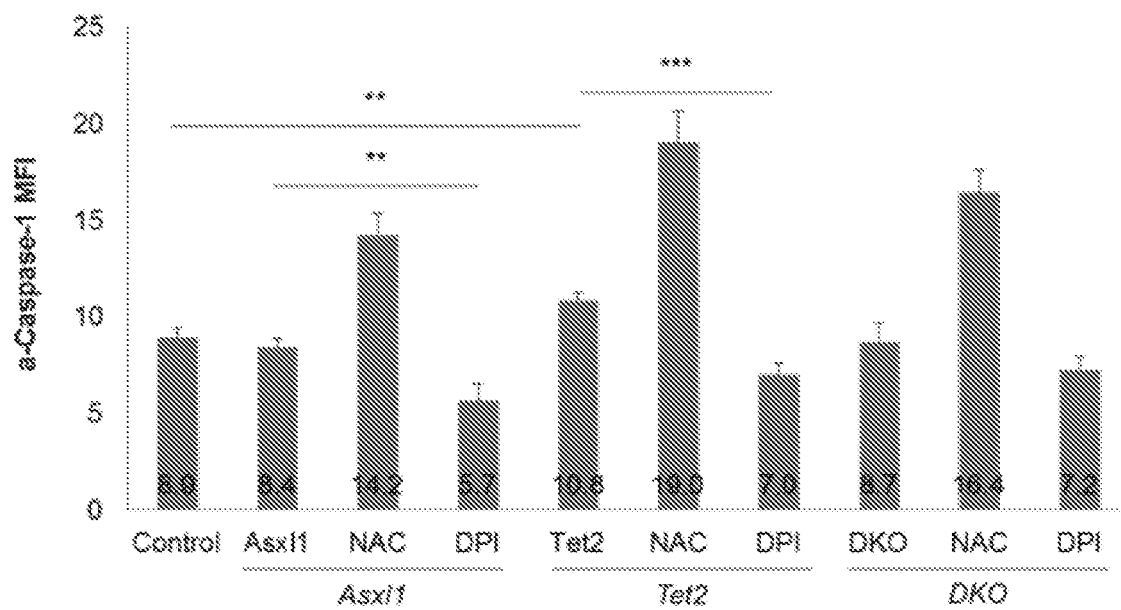
Figure 83:
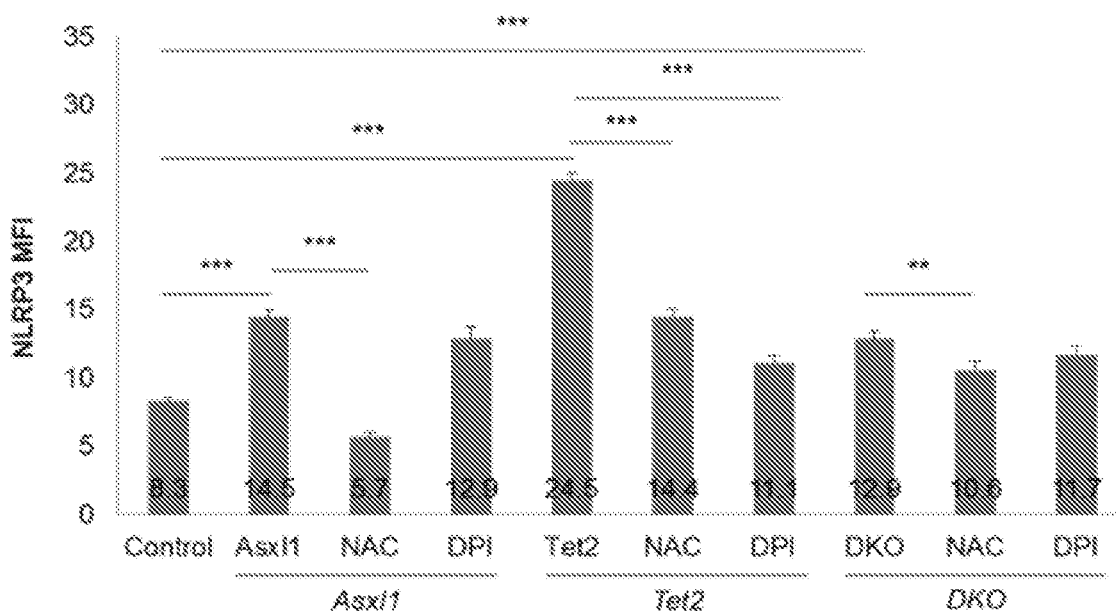
Figure 84:
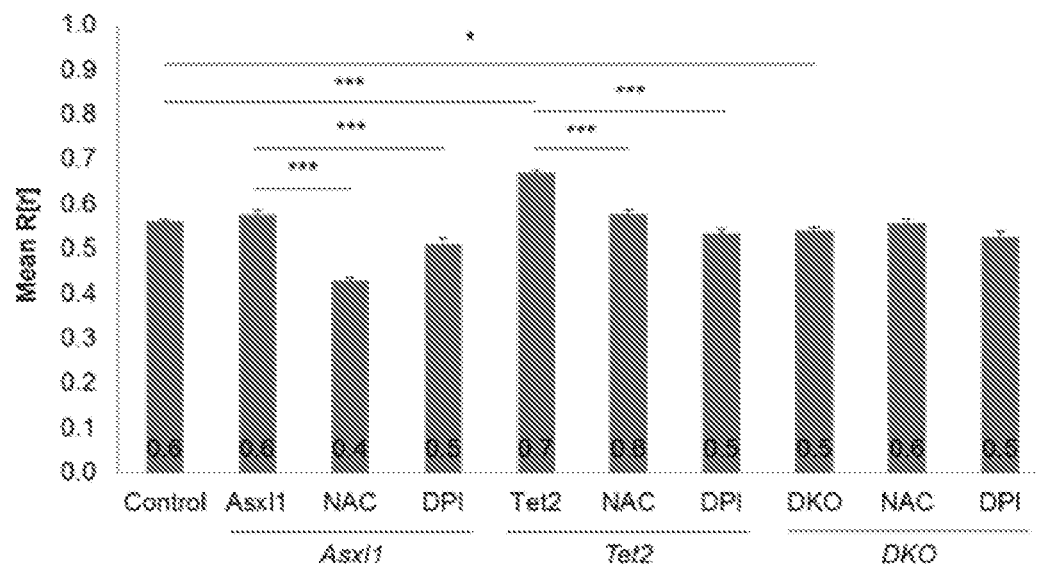
Figure 85:
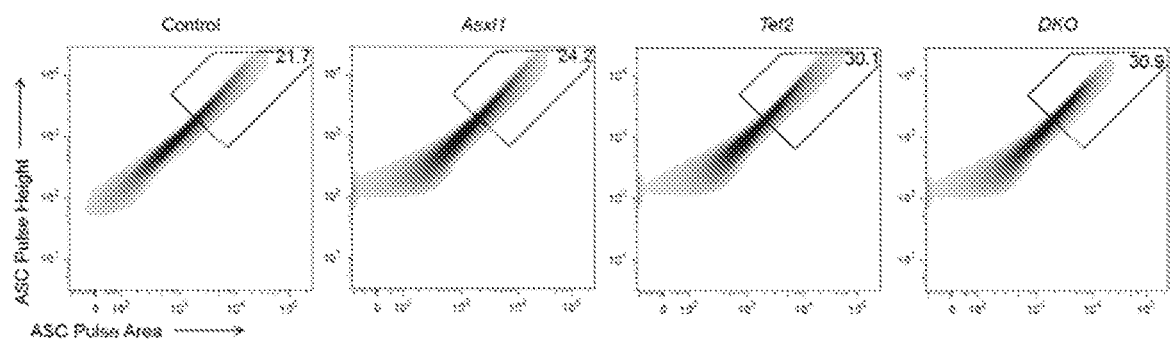
Figure 86:
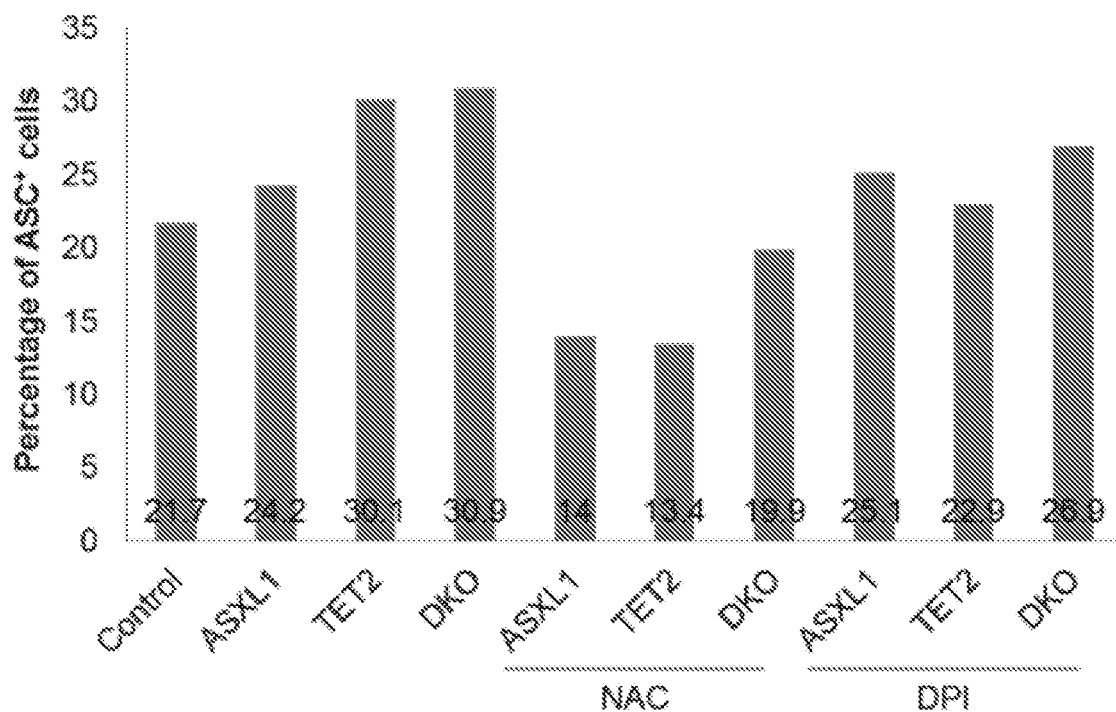
Figure 87:
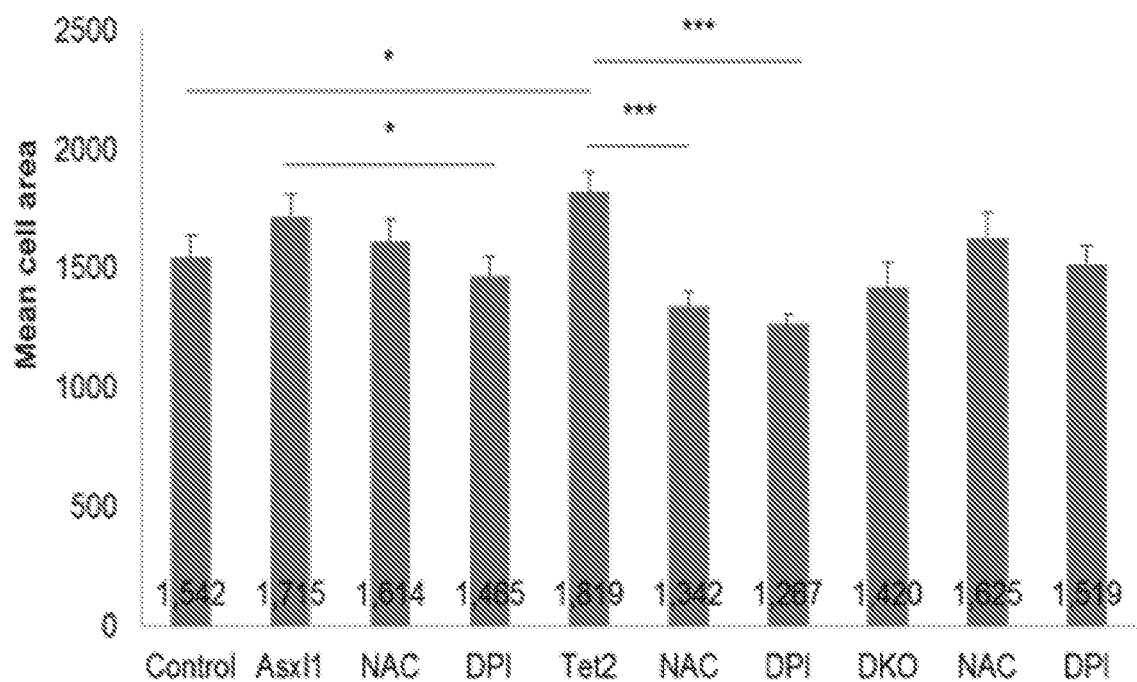
Figure 88:
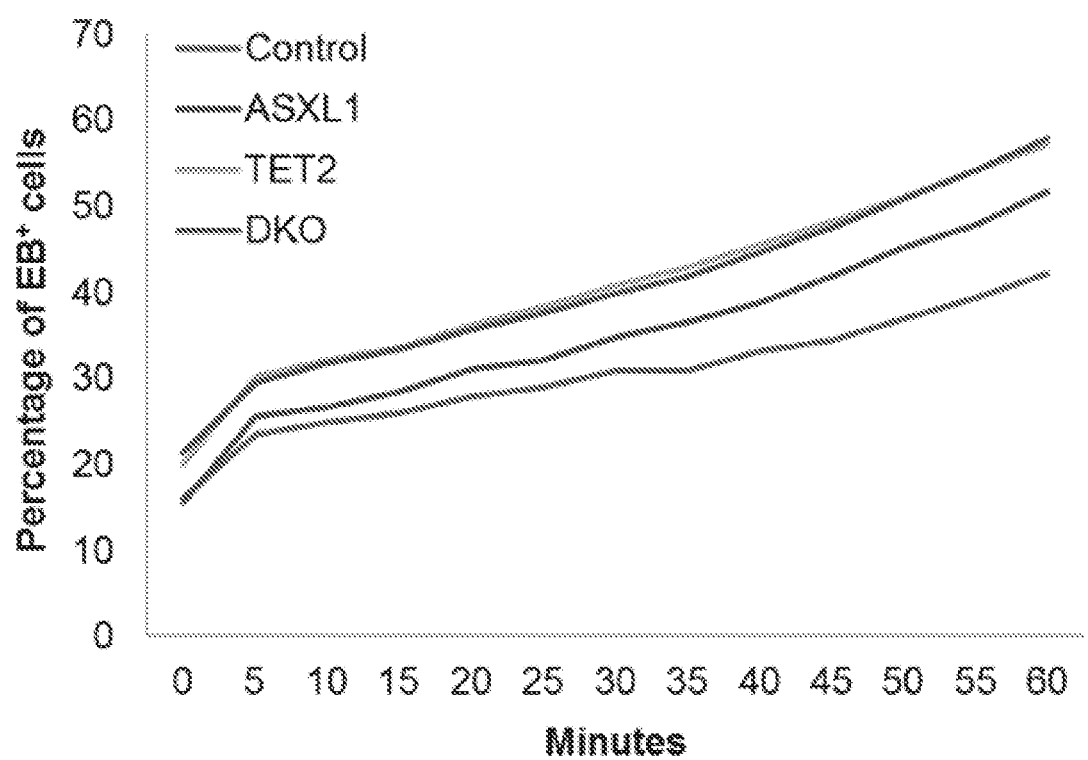
Figure 89:
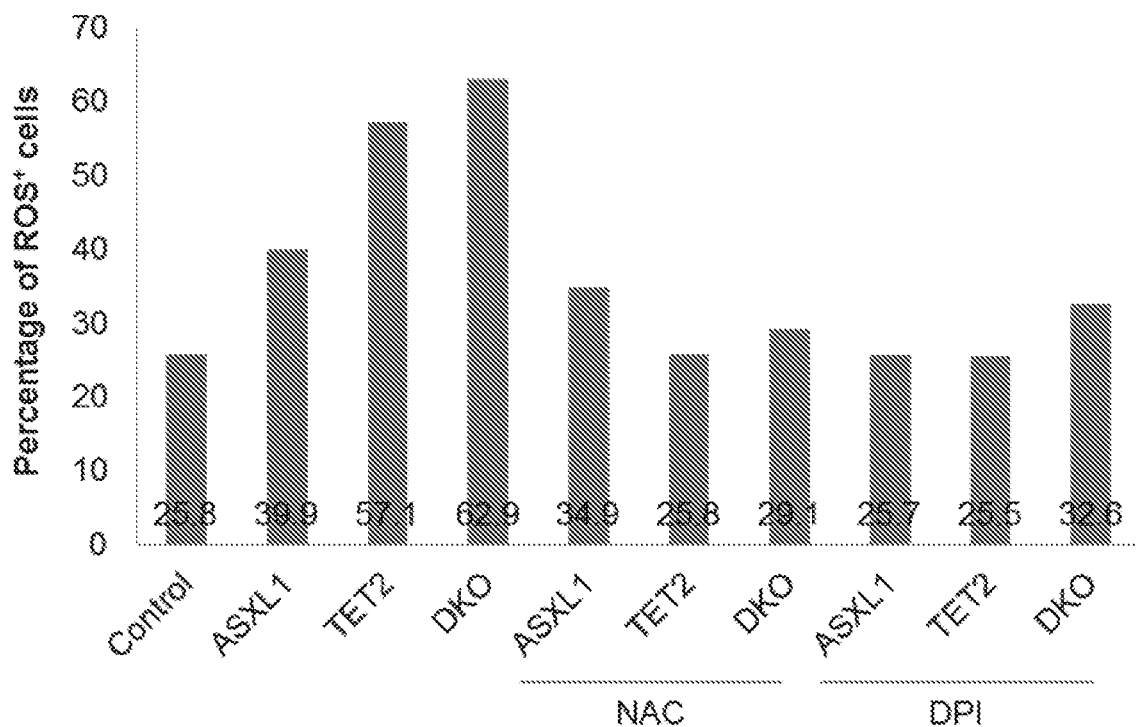
FIGS. 89-92 show that Asxl1 and Tet2 deletions are sufficient to drive self-renewal through β-catenin activation. The ability of deletions in Asxl1 and Tet2 to activate β-catenin was assessed in BM cells isolated from Asxl1 KO, Tet2 KO, and DKO cells, compared to control cells.
Figure 90:
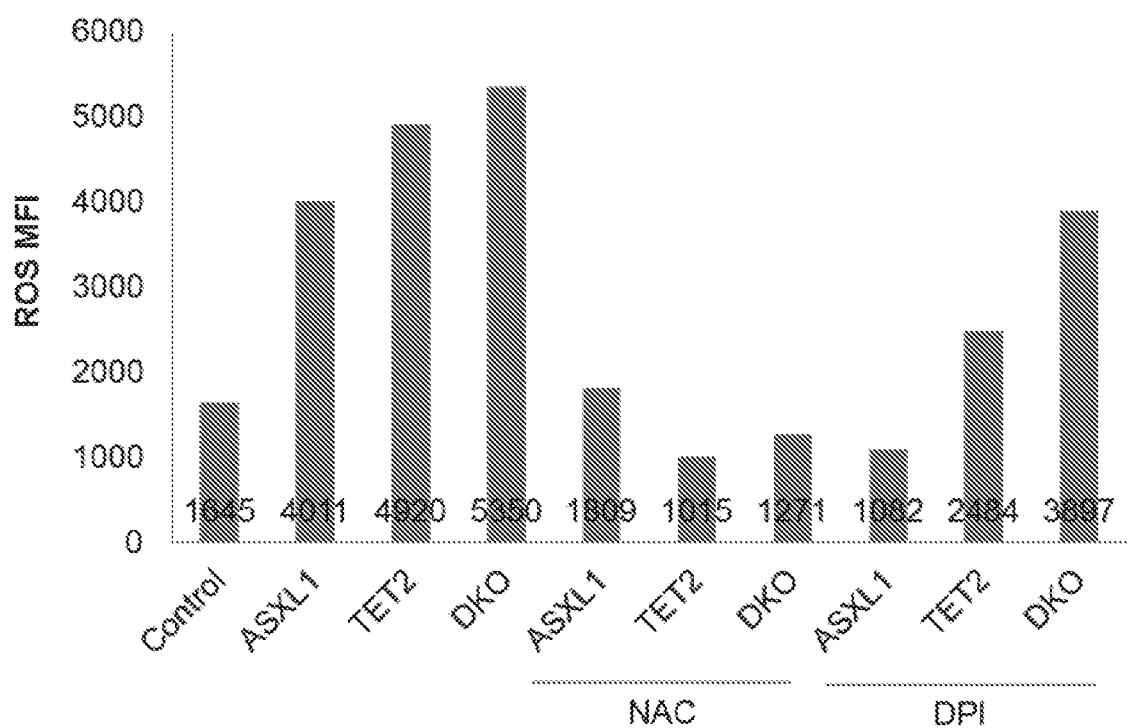
Figure 91:
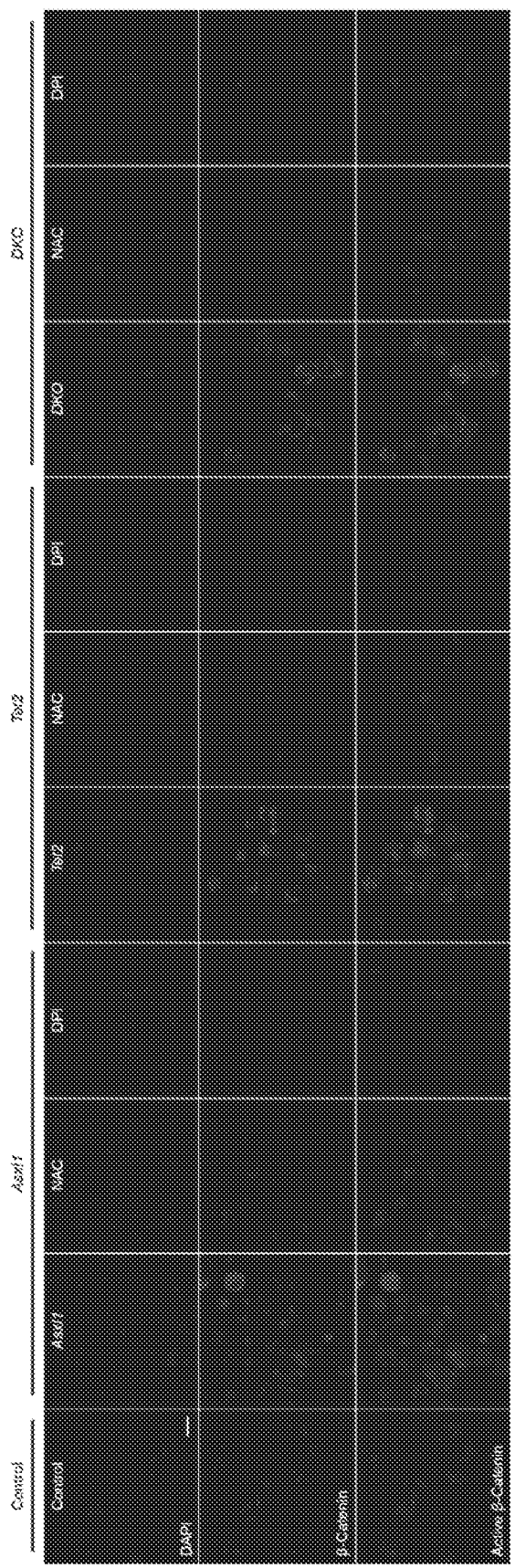
Figure 92:
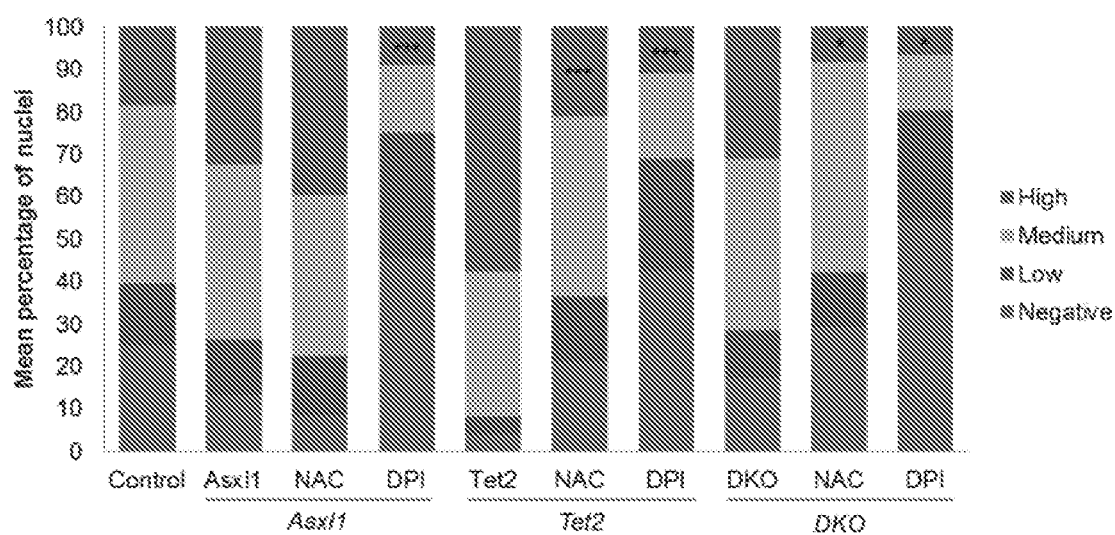

BM cells harvested from SF3B1-K700E conditional knock-in mice (n=3), which also display a MDS phenotype (Obeng E. A, et al. Blood. 2014 124(6):828-30), displayed similar increases in the percentage of pyroptotic versus apoptotic cells, with significant increases in total a-caspase-1⁺ cells (p=0.014) versus WT controls (n=3) (FIG. 64A, 64B). Further, MFI of a-caspase-1⁺ and a-caspase-3 were both significantly increased in the SF3B1-K700E mutant BM cells (p=0.030 and $p=6.92 \times 10^{-3}$, respectively) (FIG. 65), which displayed inflammasome assembly (FIG. 66). Accordingly, NLRP3 protein expression was increased 1.9-fold in the SF3B1-K700E cells (p=0.063), as NLRP3 inflammasome formation was increased 1.2-fold (FIG. 67). Inflammasome formation was also assessed by flow cytometry based on the detection of the inflammasome adaptor protein ASC oligomerization, whose incorporation into inflammasome complexes can be detected by changes in fluorescence pulse height and area (Sester D. P, et al. J Immunol. 2015 194(1):455-62). SF3B1-K700E mutant-expressing BM cells (n=6) had marked increases in inflammasome formation versus WT controls (n=6, $p=8.4 \times 10^{-3}$), which was significantly reduced upon treatment with NAC (n=6, $p=2.68 \times 10^{-3}$) or DPI (n=3) (FIG. 68, 69). Moreover, mean percentage of ROS⁺ cells and ROS MFI were both markedly increased in SF3B1-K700E-expressing mutant BM cells, which was extinguished below the level of WT controls by NAC or DPI treatment (FIG. 70, 71). Finally, SF3B1-K700E mutant-expressing BM cells demonstrated a statistically significant increase in the percentage of cells with elevated levels of nuclear β-catenin compared to WT controls (p=0.40), which was significantly reduced upon treatment with NAC ($p=2.0 \times 10^{-3}$) or DPI ($p=1.8 \times 10^{-2}$) (FIG. 72, 73). Similar findings were observed in mutant versus WT SRSF2-expressing HEK293T cells (FIGS. 74-80), as well as with epigenetic regulatory gene mutations (ASXL1, TET2) (FIGS. 81-92). Notably, in MDS BM specimens, BM plasma concentration of S100A9 positively correlated with NLRP3 MFI, as did the presence of spliceosome gene mutations and variant allele frequency (VAF) (FIG. 117). Finally, the percentage of pyroptotic erythroid precursors significantly increased in parallel with splicing gene mutation VAF along with the number of spliceosome mutations. Thus, MDS somatic gene mutations prime cells to undergo pyroptosis, which promotes self-renewal and contributes to an inflammatory microenvironment that is driven by ROS.

MDS HSPCs are Primed for NLRP3 Inflammasome Activation

Given the increased oxidative stress in MDS, the contribution of redox-proteins in mediating NLRP3 inflammasome activation was investigated. ROS oxidize thioredoxin (TRX) triggering its dissociation from thioredoxin-interacting protein (TXNIP). Recent studies suggest that liberated TXNIP serves as a redox sensitive ligand that binds NLRP3 and activates inflammasome complex assembly. TANIP gene expression was increased 9.6-fold in lower-risk MDS BM-MNC (n=9) compared to normal donors (n=4), and increased 3.4-fold in U2AF1-S34F-expressing cells compared to WT U2AF1-expressing cells (FIG. 109). Further, there was increased binding of TXNIP to NLRP3 in MDS and S34F-expressing cells, compared to normal donors and WT cells, respectively (FIGS. 110 and 111). Notably, increased NLRP3 oligomerization and activation was confirmed through binding of NLRP3:ASC (FIGS. 110 and 111). Moreover, mRNA and protein levels of the pyrin domain-only protein (POP)-1, a key negative regulator of NLRP3 inflammasome activation that functions as a dominant-negative ASC antagonist blocking ASC oligomerization, was profoundly reduced in both lower-risk MDS BM-MNC (n=9) and U2AF-S34F-expressing cells (FIGS. 112 and 113). To determine if NLRP3 inflammasome activation is reinforced in MDS by reduced expression of POP-1, U2AF1-S34F cells were transfected with POP-1 expression vectors. Significant increases in POP-1 expression were associated with a 40% reduction in NLRP3 activation, as measured by ASC oligomerization (FIG. 114). Collectively, these findings indicate that MDS HSPCs are primed for NLRP3 inflammasome activation as a result of decreased expression of the POP1 pyrin domain antagonist.

Ineffective hematopoiesis in MDS has been attributed to high fractions of proliferating BM progenitors with a propensity to undergo apoptotic cell death within an unexplained inflammatory microenvironment (Span L. F, et al. Leuk Res. 2007 31(12):1659-67; Raza A, et al. Blood. 1995 86(1):268-76). Nearly two decades ago it was reported that MDS HSPC generate IL-1β in short term cultures, which directly correlated with the extent of apoptosis as measured by DNA fragmentation (Mundle S. D, et al. Blood. 1996 88(7):2640-7). Evidence is disclosed that these and other biological features of MDS are explained by the activation of the NLRP3 pattern recognition receptor by S100A9 and by ROS DAMP intermediates that induce inflammasome assembly, β-catenin nuclear translocation and pyroptotic cell death. Notably, pyroptotic-associated gene transcripts and inflammasome assembly are up-regulated in MDS independent of genotype. Moreover, pyroptotic but not apoptotic cells are markedly increased in MDS stem cells, progenitors, and erythroid precursors. Accordingly, knockdown of caspase-1, but not caspase-3, in MDS BM-MNC, significantly reduced the pyroptotic cell fraction. Similarly, neutralization of S100A9 in MDS BM plasma, or pharmacologic inhibition of inflammasome assembly, suppressed pyroptosis and restored effective hematopoiesis in vitro and in a murine MDS model. Thus, pyroptosis, a caspase-1-dependent inflammatory cell death, impairs HSPC survival in MDS.

S100A8/S100A9 activate both NF-κB and NLRP3 inflammasome assembly via an NADPH oxidase (NOX)/ROS-dependent mechanism (Simard J. C, et al. PLoS One. 2013 8(8):e721381; Liao P. C, et al. Inflamm Res. 2013 62(1):89-96; Heid M. E, et al. J Immunol. 2013 191(10): 5230-8: Bauernfeind F. et al. J Immunol. 2011 187(2):613-7). S100A8/9 heterodimers serve as a scaffold for the membrane assembly and activation of the NOX complex (Doussiere J, et al. Eur J Biochem. 2002 269(13):3246-55; Kerkhoff C, et al. FASEB J. 2005 19(3):467-9), which generates ROS via transfer of electrons across membranes to generate superoxide (Bedard K, et al. Physiol Rev. 2007 87(1):245-313). NOX activity regulates both priming and activation of NLRP3 inflammasomes, as NOX inhibition suppresses the activation of caspase-1 and IL-1β secretion (Liao P. C, et al. Inflamm Res. 2013 62(1):89-96). Moreover, transcription and nuclear localization of β-catenin are redox- and NOX1-dependent (Coant N, et al. Mol Cell Biol. 2010 30(11):2636-50; Wu X, et al. Cell. 2008 133(2):340-53). Although MDSC are a key paracrine source of S100A9 in the MDS BM-microenvironment (Chen X, et al. J Clin Invest. 2013 123(11):4595-611), here it is shown that MDS HSPC also express high intracellular levels of S100A9 (FIG. 49-51), suggesting that inflammasome activation may be sustained by intracrine DAMP stimulation, and upon cell lysis, promote BM expansion of MDSC. Importantly, NOX inhibition suppressed inflammasome and β-catenin activation in both patient-derived BM-MNC and cells harboring varied classes and types of MDS founder gene mutations. Thus, S100A9 induces NOX activity to drive ROS-dependent inflammasome assembly and pyroptosis, accompanied by β-catenin nuclear translocation.

A hallmark of MDS BM precursors is their enlarged cell size or macrocytosis. It is shown that activation of pattern recognition receptors triggers expansion in size of MDS progenitors via influx of cations mediated by the transient receptor potential melastatin 2 (TRMP2) cation channel, a plasma membrane calcium-permeable channel in hematopoietic cells (Zhang W, et al. Am J Physiol Cell Physiol. 2006 290(4):C1146-59). Further, TRPM2 channels are activated by NOX-derived ROS via oxidation of a single channel methionine residue, Met-214, which is indispensable for NLRP3 inflammasome activation (Kashio M, et al. Proc Natl Acad Sci USA. 2012 109(17):6745-50; Zhong Z, et al. Nat Commun. 2013 4:1611; Yamamoto S, et al. Nat Med. 2008 14(7):738-47). Activation of TRPM2 then directs calcium influx that then leads to corresponding increases in cell volume (Kuhn F, et al. Pflugers Arch. 2005 451(1):212-9). The disclosed data show that MDS BM-MNC display increased influx of the TRPM2 channel substrate ethidium bromide, confirming inflammasome-initiated pore formation. Additionally, quantifying BM cell size according to lineage and stage of maturation confirmed the larger size of MDS BM precursors versus normal controls. The disclosed findings indicate that S100A9-mediated NOX activation and subsequent inflammasome initiated pyroptosis can explain the characteristic larger cell size, proliferation and inflammatory cell death manifest in MDS.

NOX-derived ROS enhance mitogenic response to receptor-tyrosine kinases through oxidative inactivation of protein tyrosine phosphatases (Block K & Gorin Y. Nat Rev Cancer. 2012 12(9):627-37). Somatic gene mutations found in MDS are known to trigger Rac1/NOX-dependent ROS generation (Sallmyr A, et al. Cancer Lett. 2008 270(1):1-9; Rassool F, et al. Cancer Res. 2007 67(18):8762-71). As ROS serve as DAMP intermediates that activate both inflammasomes and β-catenin, ROS generated by either S100A9 or MDS somatic gene mutations may drive pyroptosis, self-renewal and propagation of the MDS clone. Mechanistically, NOX-derived ROS stabilizes and activates β-catenin by oxidation and dissociation of nucleoredoxin (NRX) from disheveled (Dvl), which in turn inactivates the β-catenin destruction complex (Funato Y, et al. Nat Cell Biol. 2006 8(5):501-8). It is shown herein that ROS and nuclear β-catenin localization are increased in MDS HSPC. Further, S100A9 treatment of normal BM-MNC is sufficient to trigger nuclear translocation of β-catenin that is abolished by the anti-oxidant NAC or NADPH-oxidase inhibition. Similarly, BM-MNC from S100A9-Tg mice displayed marked increases in the expression and nuclear localization of 3-catenin, with corresponding up-regulation of Pβ-catenin target genes (data not shown). Of particular importance, varied RNA splicing gene mutations (U2AF1, SF3B1, SRSF2) and epigenetic regulatory gene mutations (ASXL1, TET2) found in MDS triggered pyroptosis, pore formation, cell volume expansion and β-catenin activation, which was extinguished by treatment with NAC or NOX-inhibition. Thus, both S100A9-induced NOX activation and MDS gene mutations initiate pyroptosis through superoxide generation to drive β-catenin activation and afford a proliferative advantage to the MDS clone. Accordingly, these findings explain how such diverse somatic gene mutations give rise to an MDS phenotype.

Figure 93:
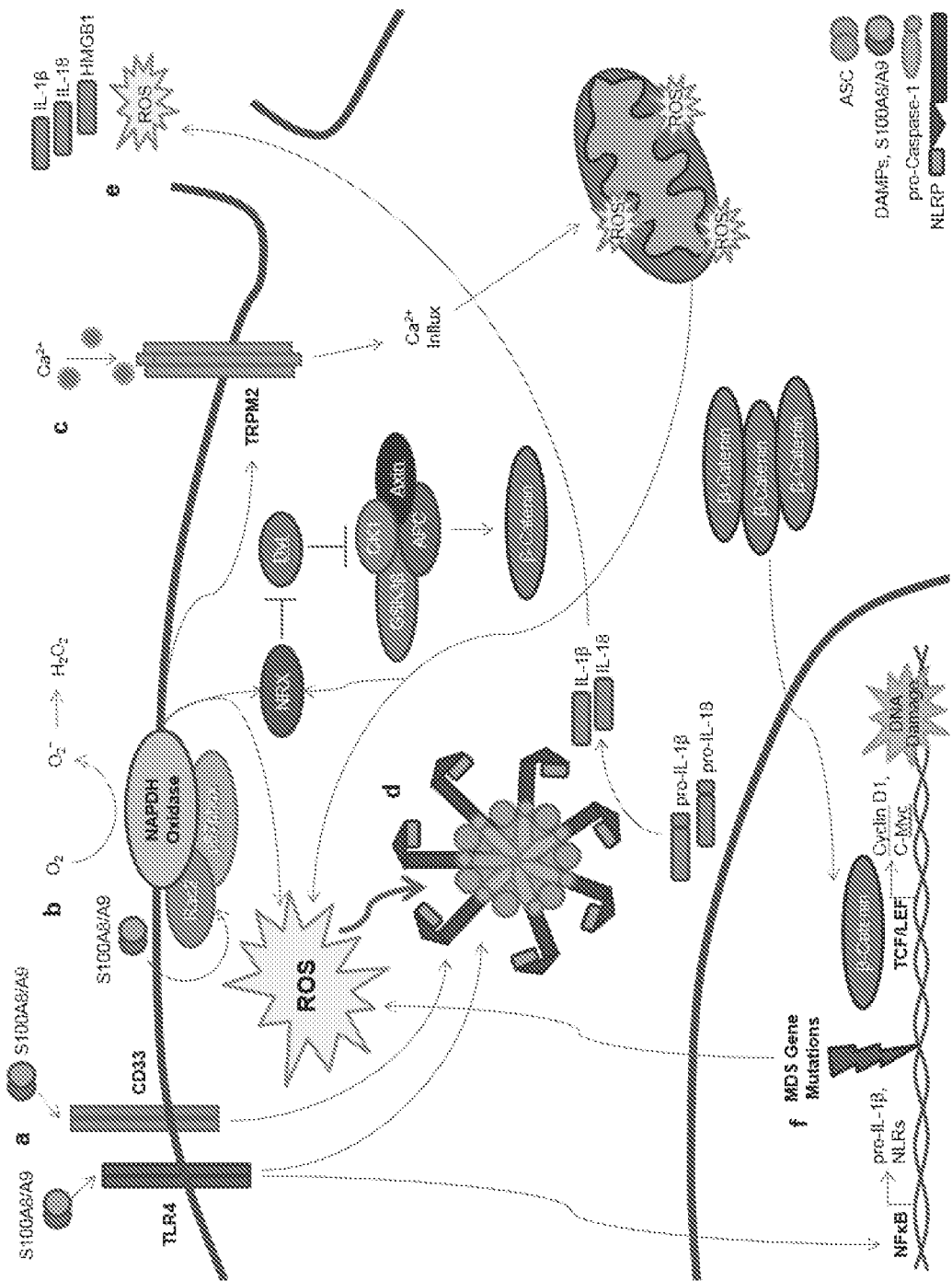
FIG. 93. A S100A9-pyroptosis circuit provokes phenotypes manifest in MDS. a, S100A8/A9 binds both CD33 and TLR4, resulting in inflammasome assembly. Ligation of S100A8/A9 to TLR4 results in NFκB-mediated transcription and subsequent production of proinflammatory cytokines such as pro-IL-1β and pro-IL-18, along with inflammasome components. b, Through interaction with Rac2 and p67phox, S100A8/A9 promotes activation of NOX, which results in a dual function. First, NOX proteins generate ROS, which serve to activate NLRs and inflammasome assembly. Second, NOX-derived ROS results in oxidation of NRX, leading to its dissociation from Dvl. Once dissociated, Dvl suppress the β-catenin destruction complex (GSKβ/CK1/APC/Axin), resulting in stabilization of β-catenin. This allows β-catenin to enter the nucleus and induce transcription of TCF/LEF controlled genes, including cyclin-D1 and c-Myc, which are essential to self-renewal. c, Transient receptor potential melastatin 2 (TRPM2), a calcium-permeable cation channel in hematopoietic cells, is activated by NOX-derived ROS via oxidation of a single channel methionine residue, Met$^{214}$. Upon activation, TRPM2 causes an influx of calcium leading to mitochondrial depolarization and further release of ROS, which activate the inflammasome complex. d, Formation of the inflammasome complex occurs as a consequence of ROS activation and DAMP signaling. Once activated, inflammasomes mediate conversion of pro-caspase-1 to its mature and catalytically active form. Active caspase-1 cleaves pro-IL-1β and pro-IL-18 to their mature forms. e, Pyroptosis ensues with loss of membrane integrity resulting in release of pro-inflammatory cytokines and other intracellular contents into the extracellular milieu. f, MDS-related gene mutations activate NF-κB and NLRP3 via NOX-generated ROS (Sallmyr A, et al. Cancer Lett. 2008 270(1): 1-9, Rassool F, et al. Cancer Res. 2007 67(18):8762-71).

Despite genetic heterogeneity, inflammasome activation underlies the biological phenotype in MDS, whereby DAMP signals and MDS gene mutations license a common redox-sensitive inflammasome platform to drive pyroptotic death, elaborate inflammatory cytokines, activate cation influx, and support propagation of the MDS clone through β-catenin activation (FIG. 93).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for treating a myelodysplastic syndromes (MDS) in a subject, comprising administering to the subject a therapeutically effective amount of an inflammasome inhibitor, wherein the MDS in the subject is non-del(5q) MDS or del(5q) MDS.

2. The method of claim 1, wherein the inflammasome inhibitor comprises a NLRP3 inflammasome inhibitor.

3. The method of claim 2, wherein the inflammasome inhibitor has the following structure:

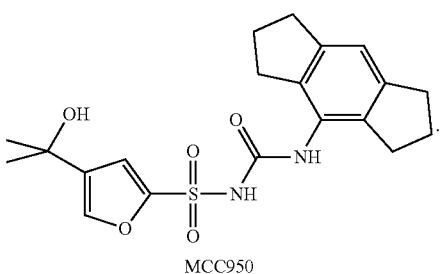 [SMILES: CC(C)(O)c1coc(S(=O)(=O)NC(=O)Nc2c3c(cc4c2CCC4)CCC3)c1]

MCC950

4. The method of claim 2, wherein the inflammasome inhibitor is selected from the group consisting of comprises glybenclamide (glyburide), 5-chloro-2-methoxy-N-[2-(4-sulfamoylphenyl)ethyl]benzamide, and isoliquiritigenin.

5. The method of claim 1, wherein the inflammasome inhibitor comprises a caspase-1 inhibitor or a pan-caspase inhibitor.

6. The method of claim 1, wherein the MDS in the subject is non-del(5q) MDS.

7. The method of claim 1, wherein the MDS in the subject is del(5q) MDS.

8. The method of claim 1, wherein the inflammasome inhibitor comprises an S100A9 inhibitor.

9. The method of claim 8, wherein the S100A9 inhibitor is an S100A9 high-affinity chimeric (CD33-IgG$_1$) decoy receptor.

10. The method of claim 5, wherein the caspase-1 inhibitor is a shRNA targeting CASP1.

11. The method of claim 1, further comprising administering to the subject a therapeutically effective amount of lenalidomide (LEN).

* * * * *

SEQUENCE LISTING

<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Synthetic Construct

<400> SEQUENCE: 1
tgagcagcca gatggtagag c                                              21

<210> SEQ ID NO 2
<211> LENGTH: 24
<212> TYPE: DNA
<213> ORGANISM: Artificial Sequence
<220> FEATURE:
<223> OTHER INFORMATION: Synthetic Construct

<400> SEQUENCE: 2
gtgaggcggt tgtagaagag tttc                                           24

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
ctcttcgagg cacaaggcac                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
actgcctgga cagtcagcaa                                                20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
tctacgttgg ccacttggga                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
caatggggag gagaaggcgt                                                20

<210> SEQ ID NO 7
<211> LENGTH: 21
<212> TYPE: DNA

```
<213> ORGANISM: Artificial Sequence
<220> FEATURE:
<223> OTHER INFORMATION: Synthetic Construct

<400> SEQUENCE: 7
ctcggctttg acagagtgca a                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
ccctcccaaa ggggagacaa a                                              21

<210> SEQ ID NO 9
<211> LENGTH: 18
<212> TYPE: DNA
<213> ORGANISM: Artificial Sequence
<220> FEATURE:
<223> OTHER INFORMATION: Synthetic Construct

<400> SEQUENCE: 9
gaaggtgaag gtcggact                                                  18

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
tcacttcctg cccacagaca t                                              21

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
tgagcagggc tcgctaactc                                                20

<210> SEQ ID NO 12
<211> LENGTH: 23
<212> TYPE: DNA
<213> ORGANISM: Artificial Sequence
<220> FEATURE:
<223> OTHER INFORMATION: Synthetic Construct
```

<400> SEQUENCE: 12
caagtcatcc tcattgccac tgt                                                  23

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

<400> SEQUENCE: 13
gcagccatct ttattcctga ga                                                   22

<210> SEQ ID NO 14
<211> LENGTH: 22
<212> TYPE: DNA
<213> ORGANISM: Artificial Sequence
<220> FEATURE:
<223> OTHER INFORMATION: Synthetic Construct

<400> SEQUENCE: 14
agaggtgaag gtacggctat gc                                                   22

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
tctgaacccc acttcggctc                                                      20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
ctggttcagg gtgtctgggt                                                      20

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
agaggaagaa ggccgaagga g                                                    21

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
gaagatggtg atgggatttc                                                      20